United States Patent
Brondyk et al.

(10) Patent No.: US 11,434,276 B2
(45) Date of Patent: Sep. 6, 2022

(54) POLYPEPTIDES WITH ALTERED BINDING TO NEONATAL FC RECEPTOR (FCRN) AND METHODS OF USE

(71) Applicant: Invetx, Inc., Boston, MA (US)

(72) Inventors: William Brondyk, Mansfield, MA (US); Brett Chevalier, Melrose, MA (US); Juergen Horn, Marblehead, MA (US); Madhusudan Natarajan, Waban, MA (US)

(73) Assignee: Invetx, Inc., Boston, MA (US)

( * ) Notice: Subject to any disclaimer, the term of this patent is extended or adjusted under 35 U.S.C. 154(b) by 0 days.

(21) Appl. No.: 17/317,782

(22) Filed: May 11, 2021

(65) Prior Publication Data

US 2021/0347854 A1   Nov. 11, 2021

Related U.S. Application Data

(60) Provisional application No. 63/122,417, filed on Dec. 7, 2020, provisional application No. 63/023,083, filed on May 11, 2020.

(51) Int. Cl.
| | | |
|---|---|---|
| *A61K 38/00* | (2006.01) | |
| *C07K 16/00* | (2006.01) | |
| *C07K 14/52* | (2006.01) | |
| *C07K 14/705* | (2006.01) | |
| *C07K 14/71* | (2006.01) | |
| *C07K 14/715* | (2006.01) | |

(52) U.S. Cl.
CPC .............. *C07K 16/00* (2013.01); *C07K 14/52* (2013.01); *C07K 14/70521* (2013.01); *C07K 14/70528* (2013.01); *C07K 14/71* (2013.01); *C07K 14/7155* (2013.01); *C07K 2317/524* (2013.01); *C07K 2317/526* (2013.01); *C07K 2317/569* (2013.01); *C07K 2317/92* (2013.01); *C07K 2317/94* (2013.01); *C07K 2319/30* (2013.01)

(58) Field of Classification Search
CPC ........ C07K 2317/524; C07K 2317/526; C07K 2317/94; C07K 2319/30
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | DeCant et al. | |
| 4,447,233 A | 5/1984 | Mayfield | |
| 4,487,603 A | 12/1984 | Harris | |
| 4,634,665 A | 1/1987 | Axel et al. | |
| 5,179,017 A | 1/1993 | Axel et al. | |
| 5,292,658 A | 3/1994 | Cormier et al. | |
| 5,418,155 A | 5/1995 | Cormier et al. | |
| 5,683,888 A | 11/1997 | Campbell | |
| 5,741,668 A | 4/1998 | Ward et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,876,995 A | 3/1999 | Bryan | |
| 5,925,558 A | 7/1999 | Tsien et al. | |
| 8,790,651 B2 | 7/2014 | Bammert et al. | |
| 10,982,002 B2 | 4/2021 | Steiniger et al. | |
| 2006/0067930 A1 | 3/2006 | Adams et al. | |
| 2007/0148164 A1 | 6/2007 | Farrington et al. | |
| 2008/0181887 A1 | 7/2008 | Dall-Acqua et al. | |
| 2013/0129727 A1 | 5/2013 | Zhang et al. | |
| 2018/0009869 A1 | 1/2018 | Lu et al. | |
| 2020/0216536 A1 | 7/2020 | Brondyk et al. | |
| 2020/0362034 A1 | 11/2020 | Zhan et al. | |
| 2020/0362035 A1 | 11/2020 | Brondyk et al. | |
| 2021/0388053 A1 | 12/2021 | Zhan et al. | |
| 2022/0009994 A1 | 1/2022 | Brondyk et al. | |
| 2022/0048981 A1 | 2/2022 | Nakao et al. | |
| 2022/0064263 A1 | 3/2022 | Zhan et al. | |

FOREIGN PATENT DOCUMENTS

| | | |
|---|---|---|
| EP | 3668536 | 6/2020 |
| EP | 3866842 | 8/2021 |
| EP | 3892632 | 10/2021 |
| EP | 3902564 | 11/2021 |
| WO | WO 92/15673 | 9/1992 |
| WO | WO 95/07463 | 3/1995 |
| WO | WO 98/14605 | 4/1998 |
| WO | WO 98/26277 | 6/1998 |
| WO | WO 99/49019 | 9/1999 |
| WO | WO 2010/110838 | 9/2010 |
| WO | WO 2010/117448 | 10/2010 |
| WO | WO 2017/186928 | 11/2017 |
| WO | WO 2018/073185 | 4/2018 |
| WO | WO 2019/035010 | 2/2019 |
| WO | WO 2020/056393 | 3/2020 |
| WO | WO 2020/082048 | 4/2020 |
| WO | WO 2020/116560 | 6/2020 |
| WO | WO 2020/142625 | 7/2020 |

(Continued)

OTHER PUBLICATIONS

US Third-Party Submission in U.S. Appl. No. 16/733,105, mailed Jul. 22, 2021, 14 pages.

(Continued)

*Primary Examiner* — Dong Jiang
(74) *Attorney, Agent, or Firm* — Clark & Elbing LLP

(57) ABSTRACT

Provided are compositions for increasing the half-life of a polypeptide or polypeptides in a canine and methods of their use. The compositions involve variant canine IgG Fc regions.

13 Claims, 63 Drawing Sheets
(32 of 63 Drawing Sheet(s) Filed in Color)
Specification includes a Sequence Listing.

(56) References Cited

FOREIGN PATENT DOCUMENTS

| WO | WO 2021/165417 | 8/2021 |
| WO | WO 2021/212081 | 10/2021 |
| WO | WO 2021/212084 | 10/2021 |

OTHER PUBLICATIONS

Dong et al., "Quantitative Prediction of Human Pharmacokinetics for Monoclonal Antibodies," Clin Pharmacokinet, Feb. 2011, 50(2):131-142.

Gearing et al., "In Vitro and In Vivo Characterization of a Fully Felinized Therapeutic Anti-Nerve Growth Factor Monoclonal Antibody for the Treatment of Pain in Cats," J Vet Intern Med, Jun. 2016, 30(4):1129-1137.

GenBank Accession No. AF198257.1, "Felis catus immunoglobulin kappa light chain mRNA, complete cds," Nov. 21, 1999, 2 pages.

GenBank Accession No. AY829266.1, "Felis catus beta-2 microglobulin mRNA, complete cds," Dec. 13, 2004, 1 page.

GenBank Accession No. BAA32229.1, "IgG1 heavy chain, partial [Felis catus]," Jul. 25, 2016, 2 pages.

GenBank Accession No. BAA32230.1, "IgG1 heavy chain, partial [Felis catus]," Jul. 25, 2016, 2 pages.

GenBank Accession No. E07339.1, "DNA sequence of C lambda gene in the constant region of feline antibody gene," Nov. 4, 2005, 1 page.

GenBank Accession No. KF773786.1, "Felis catus FcRn mRNA, partial cds," Mar. 28, 2014, 2 pages.

GenBank Accession No. KF811175.1, "Felis catus immunoglobulin G2 heavy chain constant region mRNA, partial cds," Mar. 28, 2014.

Kanai et al., "Identification of two allelic IgG1 Ch coding regions (Cγ1) of cat," Vet. Immunol. Immunopathol., Jan. 2000, 73(1):53-62.

Strietzel et al., "In Vitro functional characterization of feline IgGs," Vet. Immunol. Immunopathol., Apr. 2014, 158(3-4):214-223.

PCT International Search Report and Written Opinion in International Appln. No. PCT/US2021/031826, dated Sep. 1, 2021, 15 pages.

Abdiche et al., "The neonatal Fc receptor (FcRn) binds independently to both sites of the IgG homodimer with identical affinity," mAbs, Mar. 2015, 7(2):331-343, 14 pages.

Beniaminovitz et al., "Prevention of rejection in cardiac transplantation by blockade of the interleukin-2 receptor with a monoclonal antibody," New Engl. J. Med., Mar. 2000, 342(9):613-619.

Bergeron et al., "Comparative functional characterization of canine IgG subclasses," Veterinary Immunology and Immunopathology, 2014, 157(1-2):31-41.

Better et al., "*Escherichia coli* secretion of an active chimeric antibody fragment," Science, May 1998, 240(4855):1041-1043.

Booth et al., "Extending human IgG half-life using structure-guided design," MAbs, Oct. 2018, 10(7):1098-1110.

Borrok et al., "pH-dependent binding engineering reveals an FcRn affinity threshold that governs IgG recycling," J. Biol. Chem., Feb. 2015, 290(7):4282-4290, 10 pages.

Chalfie et al., "Green fluorescent protein as a marker for gene expression," Science, Feb. 1994, 263(5148):802-805.

Dall'Acqua et al., "Increasing the affinity of a human IgG1 for the neonatal Fc receptor: biological consequences," J. Immunol., Nov. 2002, 169(9):5171-5180, 11 pages.

Deng et al., "Pharmacokinetics of humanized monoclonal anti-tumor necrosis factor-{alpha} antibody and its neonatal Fc receptor variants in mice and cynomolgus monkeys," Drug Metab. Dispos., Apr. 2010, 38(4):600-605.

Gearing et al., "A fully caninised anti-NGF monoclonal antibody for pain relief in dogs," BMC Veterinary Research, Nov. 2013, 9:226, 12 pages.

GenBank Accession No. AAL35301.1, "immunoglobulin gamma heavy chain A [Canis lupus familiaris]," Nov. 26, 2001, 2 pages.

GenBank Accession No. AAL35302.1, "immunoglobulin gamma heavy chain B [Canis lupus familiaris]," dated Nov. 26, 2001, 2 pages.

GenBank Accession No. AAL35303.1, "immunoglobulin gamma heavy chain C [Canis lupus familiaris]," Nov. 26, 2001, 2 pages.

GenBank Accession No. AAL35304.1, "immunoglobulin gamma heavy chain D [Canis lupus familiaris]," Nov. 26, 2001, 2 pages.

GenBank Accession No. ABY55569.1, "immunoglobulin lambda light chain variable region, partial [Canis lupus familiaris]," Jul. 26, 2016, 2 pages.

GenBank Accession No. ABY57289.1, "immunoglobulin kappa light chain variable region, partial [Canis lupus familiaris]," Jul. 26, 2016, 1 page.

GenBank Accession No. U55762, "Cloning vector pEGFP-N1, complete sequence, enhanced green fluorescent protein (egfp) and neomycin phosphotransferase genes, complete cds," Aug. 22, 2003, 3 pages.

Ghosh et al., "Natalizumab for active Crohn's disease," New Engl. J. Med., Jan. 2003, 348(1):24-32.

Heim et al., "Engineering green fluorescent protein for improved brightness, longer wavelengths and fluorescence resonance energy transfer," Curr. Biol., Feb. 1996, 6(2):178-182.

Hinton et al., "Engineered human IgG antibodies with longer serum half-lives in primates," J. Biol. Chem., Feb. 2004, 279(8):6213-6216, 5 pages.

Hogrefe et al., "Creating randomized amino acid libraries with the QuikChange Multi Site-Directed Mutagenesis Kit," Biotechniques., Nov. 2002, 33(5):1158-1165.

Ichiki et al., "Regulation of the expression of human C epsilon germline transcript. Identification of a novel IL-4 responsive element," J. Immunol., Jun. 1993, 150(12):5408-5417.

Kaufman et al., "Amplification and expression of sequences cotransfected with a modular dihydrofolate reductase complementary dna gene," Mol. Biol., Aug. 1982, 159(4):601-621.

Lei et al., "Characterization of the Erwinia carotovora peIB gene and its product pectate lyase," J. Bacteriol., Sep. 1987, 169(9):4379-4383.

Lipsky et al., "Infliximab and methotrexate in the treatment of rheumatoid arthritis. Anti-Tumor Necrosis Factor Trial in Rheumatoid Arthritis with Concomitant Therapy Study Group," New Engl. J. Med., Nov. 2000, 343(22):1594-1602.

Milgrom et al., "Treatment of allergic asthma with monoclonal anti-IgE antibody. rhuMAb-E25 Study Group," New Engl. J. Med., Dec. 1999, 341(26):1966-1973.

Mizushima et al., "pEF-BOS, a powerful mammalian expression vector," Nucleic Acids Res., Sep. 1990, 18(17):5322.

Monnet et al., "Combined glyco- and protein-Fc engineering simultaneously enhance cytotoxicity and half-life of a therapeutic antibody," Mabs, Mar. 2014, 6(2):422-436, 16 pages.

Morrison et al., "Combinatorial alanine-scanning," Curr. Opin. Chem. Biol., Jun. 2001, 5(3):302-307.

Mulligan et al., "Synthesis of rabbit beta-globin in cultured monkey kidney cells following infection with a SV40 beta-globin recombinant genome," Nature, Jan. 1979, 277(5692):108-114.

Nolan et al., "Fluorescence-activated cell analysis and sorting of viable mammalian cells based on beta-D-galactosidase activity after transduction of *Escherichia coli* lacZ," Proc. Natl. Acad. Sci. U.S.A., Apr. 1988, 85(8):2603-2607.

Petkova et al., "Enhanced half-life of genetically engineered human IgG1 antibodies in a humanized FcRn mouse model: potential application in humorally mediated autoimmune disease," Int. Immunol., Dec. 2006, 18(12):1759-1769.

Powers et al., "Expression of single-chain Fv-Fc fusions in Pichia pastoris," J Immunol Methods., May 2001, 251(1-2):123-135.

Robbie et al., "A novel investigational Fc-modified humanized monoclonal antibody, motavizumab-YTE, has an extended half-life in healthy adults," Antimicrob. Agents Chemother., Dec. 2013, 57(12):6147-6153.

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol, Chem., Mar. 2001, 276(9):6591-6604, 15 pages.

(56) References Cited

OTHER PUBLICATIONS

Slamon et al., "Use of chemotherapy plus a monoclonal antibody against HER2 for metastatic breast cancer that overexpresses HER2," New Engl. J. Med., Mar. 2001, 344(11):783-792.

Stauber et al., "Development and applications of enhanced green fluorescent protein mutants," Biotechniques, Mar. 1998, 24(3):462-471.

Tang et al., "Cloning and characterization of cDNAs encoding four different canine immunoglobulin gamma chains," Vet. Immunol. Immunopathol., Aug. 2001, 80(3-4):259-270.

Urlaub et al., "Isolation of Chinese hamster cell mutants deficient in dihydrofolate reductase activity," Proc. Natl. Acad. Sci. USA, Jul. 1980, 77(7):4216-4220.

Ward et al., "Binding activities of a repertoire of single immunoglobulin variable domains secreted from *Escherichia coli*," Nature, Oct. 1989, 341(6242):544-546.

Yeung et al., "Engineering human IgG1 affinity to human neonatal Fc receptor: impact of affinity improvement on pharmacokinetics in primates," J. Immunol., Jun. 2009, 182(12):7663-7671, 10 pages.

Zalevsky et al., "Enhanced antibody half-life improves in vivo activity," Nat. Biotechnol., Feb. 2010, 28(2):157-159.

Zhang et al., "PKSolver: An add-in program for pharmacokinetic and pharmacodynamic data analysis in Microsoft Excel," Comput. Methods Programs Biomed., Sep. 2010, 99(3):306-314.

US Third-Party Submission in U.S. Appl. No. 16/733,105, mailed May 28, 2021, 19 pages.

US Third-Party Submission in U.S. Appl. No. 16/861,077, mailed May 25, 2021, 19 pages.

imgt.org [online], "IMGT Scientific chart," 2016, retrieved from URL <http://www.imgt.org/IMGTScientificChart/Numbering/Hu_IGHGnber.html>, 7 pages.

FIG. 1

```
                       ▼─ V_H                               *
CaIgG-A   MESVFCWVFL  VVILKGVQGE  VQLVESGGDL  VKPGSSLRLS  CVASGFTFSS   50
CaIgG-B   ----LF----  -T--------  -R------T-  ----K--     -------RR    50
CaIgG-C   ----LY----  -A-------D  ----------  ----------  ----------   50
CaIgG-D   ----L-----  -S--------  ----------  ----------  ---------D   50

CaIgG-A   YMHWIRQAP   GKGLQRVAHI  RGDGRTTHYA  DAMKGRFTIS  RDNAKNTLY   100
CaIgG-B   -S-D-V---   -S---W--G-  N---TG-S-S  QTV---      ----------  100
CaIgG-C   CA-S-V--S   --P-W---T-  -Y--SDIY--  ------S--   -------V-   100
CaIgG-D   -G-S-V--S   ----W---AV  SNR- D-Y--  ----------  ----------  100
                 *                                ▼─ C_H1
CaIgG-A   QMNSLTVET   IIYGVKDI    YYGVG D     YWGQGTLVTV  SSASTTAPSV  150
CaIgG-B   -I----RA-S  N--A-S W    SRNG   DL-  ----------  ----------  150
CaIgG-C   -----RA--   V--A-A P    PYDS-HY-M-  ----P--SLF-  ----------  150
CaIgG-D   --S--KA--   IH-VTGVM    PRH---M  -  H--N--SLF-  ----------  150
                          *
CaIgG-A   FPLAPSCGST  SGSTVALACL  VSGYFPEPVT  VSWNSGSLTS  GVHTFPSVLQ  200
CaIgG-B   ----------  ----------  ----------  ----------  ----------  200
CaIgG-C   ---------Q  ----------  -----I----  ------V---  ----------  200
CaIgG-D   ----------  ----------  ----------  ----------  ----------  200
                                         *           ▼─ hinge
CaIgG-A   SSGLHSLSSM  VTVPSSRWPS  ETFTCNVVHP  ASNTKVDKPV  PNECRCTDT   250
CaIgG-B   -----Y----  ----------  -------A--  P-K-------  PKEENGRVPR  250
CaIgG-C   -----Y----  ----------  -------A--  -T--------  AK--E-KC N  250
CaIgG-D   -----Y----T ----------  ----------  ----------  PK-ST-KCI   250
              ▼─ C_H2                                *
CaIgG-A        PPCPVP  EPLGGPSVLI  FPPKPKDILR  ITRTPEVTCV  VLDLGREDPE  300
CaIgG-B   PPDC-K--A-  -M------F-  -------TLL  -A--------  -V--DP----  300
CaIgG-C   CNNC- --GC  GL------F-  ---------V  TA---T----  -V--DP-N--  300
CaIgG-D   SP----      ES------F-  ----------  -------I--  ----------  300
                                                                 *
CaIgG-A   VQISWFVDGK  EVHTAKTQSR  EQQFNGTYRV  VSVLPIEHQD  WLTGKEFKCR  350
CaIgG-B   ----------  QMQ-----P-  -E-----     -------G--  --K--Q-T-K  350
CaIgG-C   --------S-  Q-Q--N--P-  -E-S---     -------G--  --S--Q---K  350
CaIgG-D   ----------  --------P-  ----S--     ----------  ----------  350
                       ▼─ C_H3
CaIgG-A   VNHIDLPSPI  ERTISKARGR  AHKPSVYVLP  PSPKELSSSD  TVSITCLIKD  400
CaIgG-B   --NKA-----  ---------Q  --Q-------  --RE---K N  ---L------  400
CaIgG-C   --NKA-----  -EI---TP-Q  --Q-N-----  --RD-M-K N  --TL----V-  400
CaIgG-D   ----G-----  ---------Q  --Q-------  ----------  --TL------  400

CaIgG-A   FYPFDIDVEW  QSNGQQEPER  KHRMTPPQLD  EDGSYFLYSK  LSVDKSRWQQ  450
CaIgG-B   -F--------  ---------S  -Y-T------  ----------  ---------R  450
CaIgG-C   -F--E-----  ---------S  -Y-M------  ----------  ---------R  450
CaIgG-D   -F--E-----  ------P--S  -YHT-A----  ----------  ----------  450
              *
CaIgG-A   GDPFTCAVMH  ETLQNHYTDL  SLSHSPGK                            500
CaIgG-B   ---T-I----  -A-H----QE  --------                            500
CaIgG-C   ---T-I----  -A-H----QI  --------                            500
CaIgG-D   ---T------  -A--------  --------                            500
```

FIG. 2

```
Canine.IgG.A    GPSVLIFPPKPKDILRITRTPEVTCVVLDLGREDPEVQISWFVDGKEVHT
Canine.IgG.D    GPSVFIFPPKPKDILRITRTPEITCVVLDLGREDPEVQISWFVDGKEVHT
Canine.IgG.B    GPSVFIFPPKPKDTLLIARTPEVTCVVVDLPEDPEVQISWFVDGKQMQT
canine.IgG.C    GPSVFIFPPKPKDILVTARTPTVTCVVVDLDPENPEVQISWFVDSKQVQT
                ****:*******   :*** ;**** :**;**, *:*********.*::.*

Canine.IgG.A    AKTQSREQQFNGTYRVVSVLPIEHQDWLTGKEFKCRVNHIDLPSPIERTISKAR
Canine.IgG.D    AKTQPREQQFNSTYRVVSVLPIEHQDWLTGKEFKCRVNHIGLPSPIERTISKAR
Canine.IgG.B    AKTQPREEQFNGTYRVVSVLPIGHQDWLKGKQFTCKVNNKALPSPIERTISKAR
Canine.IgG.C    ANTQPREEQSNGTYRVVSVLPIGHQDWLSGKQFKCKVNNKALPSPIEEIISKTP
                *;:**.**:;* *.***********  ******. *.* :.*;***;  ***;
```

FIG. 3

```
Canine.IgG.A    KPSVYVLPPSPKELSSSDTVSITCLIKDFYPPDIDVEWQSNGQQEPERKHRMTPPQLDED
Canine.IgG.D    QPSVYVLPPSPKELSSSDTVTLTCLIKDFFPPEIDVEWQSNGQQEPESKYHTTAPQLDED
Canine.IgG.B    QPSVYVLPPSREEL-SKNTVSLTCLIKDFFPPDIDVEWQSNGQQEPESKYRTTPPQLDED
Canine.IgG.C    QPNVYVLPPSRDEM-SKNTVTLTCLVKDFFPPEIDVEWQSNGQQEPESKYRMTPPQLDED
                 :********* :: : ****:*******:*****************:: *.******

Canine.IgG.A    GSYFLYSKLSVDKSRWQQGDPFTCAVMHETLQNHYTDLSLSHSPGK
Canine.IgG.D    GSYFLYSKLSVDKSRWQQGDTFTCAVMHEALQNHYTDLSLSHSPGK
Canine.IgG.B    GSYFLYSKLSVDKSRWQRGDTFICAVMHEALHNHYTQESLSHSPGK
Canine.IgG.C    GSYFLYSKLSVDKSRWQRGDTFICAVMHEALHNHYTQISLSHSPGK
                ***************::***.*.******:*:****..:******
```

FIG. 4

```
Canine.IgG.A    VPEPLGGPSVLIFPPKPKDILRITRTPEVTCVVLDLGREDPEVQISWFVDGKEVHT
Canine.IgG.D    VPESLGGPSVFIFPPKPKDILRITRTPEITCVVLDLGREDPEVQISWFVDGKEVHT
Canine.IgG.B    APEMLGGPSVFIFPPKPKDTLLIARTPEVTCVVVDLDPEDPEVQISWFVDGKQMQT
Canine.IgG.C    GCGLLGGPSVFIFPPKPKDILVTARTPTVTCVVVDLDPENPEVQISWFVDSKQVQT
                  ******:**:*****:*** ::**** ***:**:**:** ********.*:.*

Canine.IgG.A    AKTQSREQQFNGTYRVVSVLPIEHQDWLTGKEFKCRVNHIDLPSPIERTTISKARGRAHKP
Canine.IgG.D    AKTQPREQQFNSTYRVVSVLPIEHQDWLLTGKEFKCRVNHIGLPSPIERTISKARGQAHQP
Canine.IgG.B    AKTQPREEQFNGTYRVVSVLPIGHQDWLKGKQFTCKVNNKALPSPIERTISKARGQAHQP
Canine.IgG.C    ANTQPREEQSNGTYRVVSVLPIGHQDWLSGKQFKCKVNNKALPSIEELISKTPGQAHQP
                *:**.**:*.*.**********.*****.**:* *:**:. **. **:****  .:*:*

Canine.IgG.A    SVYYLPPSPKELSSSDTVSITCLIKDFYPPDIDVEWQSNGQQEPERKHRMTPPQLDEDGS
Canine.IgG.D    SVYVLPPSPKELSSSDTVTLTCLIKDFFPPEIDVEWQSNGQPEPESKYHTTAPQLDEDGS
Canine.IgG.B    SVYVLPPSREEL-SKNTVSLTCLIKDFFPPDIDVEWQSNGQPEPESKYRTTPPQLDEDGS
Canine.IgG.C    NVYVLPPSRDEM--SKNTVTLTCLVKDFFPPEIDVEWQSNGQQEPESKYRMTPPQLDEDGS
                 ***:***  .:   ***:******* *:****:* ****::.*:  *. ********

Canine.IgG.A    YFLYSKLSVDKSRWQQGDPFTCAVMHETLQNHYTDLSLSHSPGK
Canine.IgG.D    YFLYSKLSVDKSRWQQGDTFTCAVMHEALQNHYTDLSLSHSPGK
Canine.IgG.B    YFLYSKLSVDKSRWQRGDTFTCAVMHEALHNHYTQESLSHSPGK
Canine.IgG.C    YFLYSKLSVDKSRWQRGDTFTCAVMHEALHNHYTQISLSHSPGK
                ***************:**.********:*:****: .******
```

FIG. 5

| | | CH2 DOMAIN | | | | | |
|---|---|---|---|---|---|---|---|
| | EU | hIgG1 | cIgG.A | cIgG.B | cIgG.C | cIgG.D | SM |
| A-strand | 237 | G | G | G | G | G | |
| | 238 | P | P | P | P | P | |
| | 239 | S | S | S | S | S | |
| | 240 | V | V | V | V | V | |
| | 241 | F | L | F | F | F | |
| | 242 | L | I | I | I | I | |
| | 243 | F | F | F | F | F | |
| | 244 | P | P | P | P | P | |
| | 245 | P | P | P | P | P | |
| | 246 | K | K | K | K | K | |
| | 247 | P | P | P | P | P | |
| | 248 | K | K | K | K | K | |
| | 249 | D | D | D | D | D | |
| | 250 | T | I | T | I | I | E or Q |
| | 251 | L | L | L | L | L | D or E |
| AB-turn | 252 | M | R | L | V | R | Y |
| | 253 | I | I | I | T | I | |
| B-strand | 254 | S | T | A | A | T | T |
| | 255 | R | R | R | R | R | |
| | 256 | T | T | T | T | T | D, E, or F |
| | 257 | P | P | P | P | P | |
| | 258 | E | E | E | T | E | |
| | 259 | V | V | V | V | I | |
| | 260 | T | T | T | T | T | |
| | 261 | C | C | C | C | C | |
| | 262 | V | V | V | V | V | |
| | 263 | V | V | V | V | V | |
| | 264 | V | L | V | V | L | |
| BC-loop | 265 | D | D | D | D | D | |
| | 266 | V | L | L | L | L | |
| | 267 | S | G | D | D | G | |
| | 268 | H | R | P | P | R | |
| | 269 | E | E | E | E | E | |
| | 270 | D | D | D | N | D | |
| | 271 | P | P | P | P | P | |
| | 272 | E | E | E | E | E | |
| | 273 | V | V | V | V | V | |

FIG. 5 Continued

|  | | | | | | | |
|---|---|---|---|---|---|---|---|
| | 274 | K | Q | Q | Q | Q | |
| C-strand | 275 | F | I | I | I | I | |
| | 276 | N | S | S | S | S | |
| | 277 | W | W | W | W | W | |
| | 278 | Y | F | F | F | F | |
| | 279 | V | V | V | V | V | |
| | 280 | D | D | D | D | D | |
| | 281 | G | G | G | S | G | |
| CD-loop | 282 | V | K | K | K | K | |
| | 283 | E | E | Q | Q | E | |
| | 284 | V | V | M | V | V | |
| | 285 | H | H | Q | Q | H | N,D |
| | - | - | - | - | - | - | |
| | - | - | - | - | - | - | |
| D-strand | 286 | N | T | T | T | T | D |
| | 287 | A | A | A | A | A | |
| | 288 | K | K | K | N | K | |
| | 289 | T | T | T | T | T | |
| | 290 | K | Q | Q | Q | Q | |
| | 291 | P | S | P | P | P | |
| | 292 | R | R | R | R | R | |
| | 293 | E | E | E | E | E | |
| DE-turn | 294 | E | Q | E | E | Q | |
| | 295 | Q | Q | Q | Q | Q | |
| | 296 | Y | F | F | S | F | |
| | 297 | N | N | N | N | N | |
| | 298 | S | G | G | G | S | |
| | 299 | T | T | T | T | T | |
| | 300 | Y | Y | Y | Y | Y | |
| | 301 | R | R | R | R | R | |
| E-strand | 302 | V | V | V | V | V | |
| | 303 | V | V | V | V | V | |
| | 304 | S | S | S | S | S | |
| | 305 | V | V | V | V | V | |
| | 306 | L | L | L | L | L | |
| | 307 | T | P | P | P | P | R,Q,A |
| | 308 | V | I | I | I | I | P |
| | 309 | L | E | G | G | E | P |
| | 310 | H | H | H | H | H | |
| | 311 | Q | Q | Q | Q | Q | V |

FIG. 5 Continued

| | | hIgG1 | cIgGA | cIgGB | cIgGC | cIgGD | SM |
|---|---|---|---|---|---|---|---|
| | 312 | D | D | D | D | D | |
| | 313 | W | W | W | W | W | |
| EF-turn | | - | - | - | - | - | |
| | | - | - | - | - | - | |
| F-strand | 314 | L | L | L | L | L | |
| | 315 | N | T | K | S | T | D |
| | 316 | G | G | G | G | G | |
| | 317 | K | K | K | K | K | |
| | 318 | E | E | Q | Q | E | |
| | 319 | Y | F | F | F | F | |
| | 320 | K | K | T | K | K | |
| | 321 | C | C | C | C | C | |
| FG-loop | 322 | K | R | K | K | R | |
| | 323 | V | V | V | V | V | |
| | 324 | S | N | N | N | N | |
| | 325 | N | H | N | N | H | |
| | 326 | K | I | K | K | I | |
| | 327 | A | D | A | A | G | |
| | | - | - | - | - | - | |
| | 328 | L | L | L | L | L | |
| | 329 | P | P | P | P | P | |
| | 330 | A | S | S | S | S | |
| | 331 | P | P | P | P | P | |
| | 332 | I | I | I | I | I | |
| G-strand | 333 | E | E | E | E | E | |
| | 334 | K | R | R | E | R | |
| | 335 | T | T | T | I | T | |
| | 336 | I | I | I | I | I | |
| | 337 | S | S | S | S | S | |
| | 338 | K | K | K | K | K | |
| | 339 | A | A | A | T | A | |
| | 340 | K | R | R | P | R | | hIgG1 = human IgG1; cIgGA = canine IgG.A; cIgGB = canine IgG.B; cIgGC = canine IgG.C; cIgGD = canine IgG.D; SM= mutations that can extent antibody half-life

FIG. 6

| | | CH3 DOMAIN | | | | | |
|---|---|---|---|---|---|---|---|
| | EU | hIgG1 | cIgG.A | cIgG.B | cIgG.C | cIgG.D | SM |
| A-strand | 345 | E | K | Q | Q | Q | |
| | 346 | P | P | P | P | P | |
| | 347 | Q | S | S | N | S | |
| | 348 | V | V | V | V | V | |
| | 349 | Y | Y | Y | Y | Y | |
| | 350 | T | V | V | V | V | |
| | 351 | L | L | L | L | L | |
| | 352 | P | P | P | P | P | |
| | 353 | P | P | P | P | P | |
| | 354 | S | S | S | S | S | |
| | 355 | R | P | R | R | P | |
| | 356 | D | K | E | D | K | |
| | 357 | E | E | E | E | E | |
| | 358 | L | L | L | M | L | |
| | 359 | T | S | S | S | S | |
| AB-turn | - | - | - | - | - | - | |
| | - | - | S | - | - | S | |
| B-strand | 360 | K | S | K | K | S | |
| | 361 | N | D | N | N | D | |
| | 362 | Q | T | T | T | T | |
| | 363 | V | V | V | V | V | |
| | 364 | S | S | S | T | T | |
| | 365 | L | I | L | L | L | |
| | 366 | T | T | T | T | T | |
| | 367 | C | C | C | C | C | |
| | 368 | L | L | L | L | L | |
| | 369 | V | I | I | V | I | |
| | 370 | K | K | K | K | K | |
| BC-loop | 371 | G | D | D | D | D | |
| | 372 | F | F | F | F | F | |
| | 373 | Y | Y | F | F | F | |
| | 374 | P | P | P | P | P | |
| | - | - | - | - | - | - | |
| | - | - | - | - | - | - | |
| | 375 | S | P | P | P | P | |
| | 376 | D | D | D | E | E | |
| | 377 | I | I | I | I | I | |

FIG. 6 Continued

|  | | | | | | | |
|---|---|---|---|---|---|---|---|
|  | 378 | A | D | D | D | D | V |
| C-strand | 379 | V | V | V | V | V | |
|  | 380 | E | E | E | E | E | A |
|  | 381 | W | W | W | W | W | |
|  | 382 | E | Q | Q | Q | Q | |
|  | 383 | S | S | S | S | S | |
|  | 384 | N | N | N | N | N | |
|  | 385 | G | G | G | G | G | |
| CD-loop | 386 | Q | Q | Q | Q | Q | |
|  | 387 | P | Q | Q | Q | P | |
|  | 388 | E | E | E | E | E | |
|  | 389 | N | P | P | P | P | |
|  | - | - | E | E | E | E | |
|  | - | - | R | S | S | S | |
| D-strand | 390 | N | K | K | K | K | |
|  | 391 | Y | H | Y | Y | Y | |
|  | 392 | K | R | R | R | H | |
|  | 393 | T | M | T | M | T | |
|  | 394 | T | T | T | T | T | |
|  | 395 | P | P | P | P | A | |
|  | 396 | P | P | P | P | P | |
|  | 397 | V | Q | Q | Q | Q | |
| DE-turn | 398 | L | L | L | L | L | |
|  | 399 | D | D | D | D | D | |
|  | 400 | S | E | E | E | E | |
|  | 401 | D | D | D | D | D | |
|  | 402 | G | G | G | G | G | |
|  | 403 | S | S | S | S | S | |
|  | 404 | F | Y | Y | Y | Y | |
|  | 405 | F | F | F | F | F | |
| E-strand | 406 | L | L | L | L | L | |
|  | 407 | Y | Y | Y | Y | Y | |
|  | 408 | S | S | S | S | S | |
|  | 409 | K | K | K | K | K | |
|  | 410 | L | L | L | L | L | |
|  | 411 | T | S | S | S | S | |
|  | 412 | V | V | V | V | V | |
|  | 413 | D | D | D | D | D | |
|  | 414 | K | K | K | K | K | |
|  | 415 | S | S | S | S | S | |

FIG. 6 Continued

|  | | hIgG1 | cIgGA | cIgGB | cIgGC | cIgGD | SM |
|---|---|---|---|---|---|---|---|
|  | 416 | R | R | R | R | R | |
|  | 417 | W | W | W | W | W | |
| EF-turn | | - | - | - | - | - | |
|  | | - | - | - | - | - | |
| F-strand | 418 | Q | Q | Q | Q | Q | |
|  | 419 | Q | Q | R | R | Q | |
|  | 420 | G | G | G | G | G | |
|  | 421 | N | D | D | D | D | |
|  | 422 | V | P | T | T | T | |
|  | 423 | F | F | F | F | F | |
|  | 424 | S | T | I | I | T | |
|  | 425 | C | C | C | C | C | |
| FG-loop | 426 | S | A | A | A | A | |
|  | 427 | V | V | V | V | V | |
|  | 428 | M | M | M | M | M | L |
|  | 429 | H | H | H | H | H | |
|  | 430 | E | E | E | E | E | A, K |
|  | 431 | A | T | A | A | A | |
|  | 432 | L | L | L | L | L | |
|  | 433 | H | Q | H | H | Q | K |
|  | 434 | N | N | N | N | N | S, A, F |
|  | 435 | H | H | H | H | H | Y |
|  | 436 | Y | Y | Y | Y | Y | H |
|  | 437 | T | T | T | T | T | |
| G-strand | 438 | Q | D | Q | Q | D | |
|  | 439 | K | L | E | I | L | |
|  | 440 | S | S | S | S | S | |
|  | 441 | L | L | L | L | L | |
|  | 442 | S | S | S | S | S | |
|  | 443 | L | H | H | H | H | |
|  | 444 | S | S | S | S | S | |
|  | 445 | P | P | P | P | P | |
| tail | 446 | G | G | G | G | G | |
|  | 447 | K | K | K | K | K | | hIgG1 = human IgG1; cIgGA = canine IgG.A; cIgGB = canine IgG.B; cIgGC = canine IgG.C; cIgGD = canine IgG.D; SM= mutations that can extent antibody half-life Time - sec Time - sec Time - sec Time - sec Time - sec Time - sec Time - sec

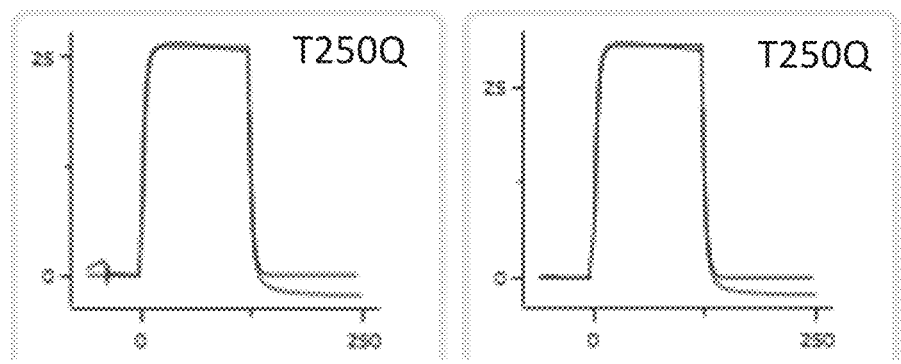
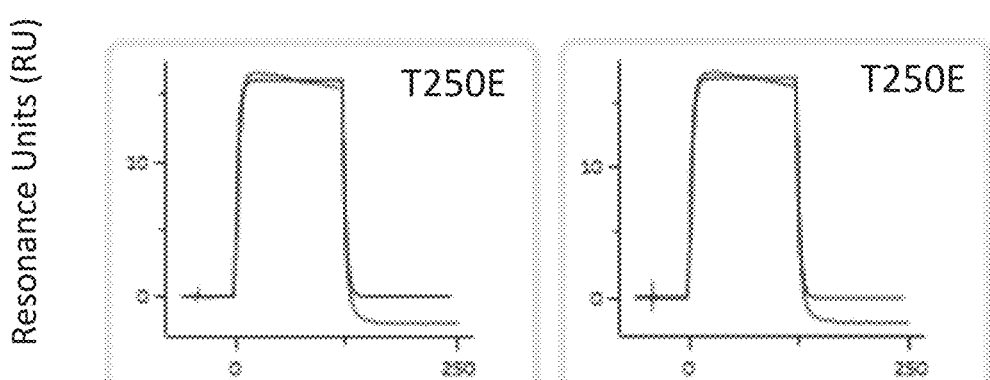
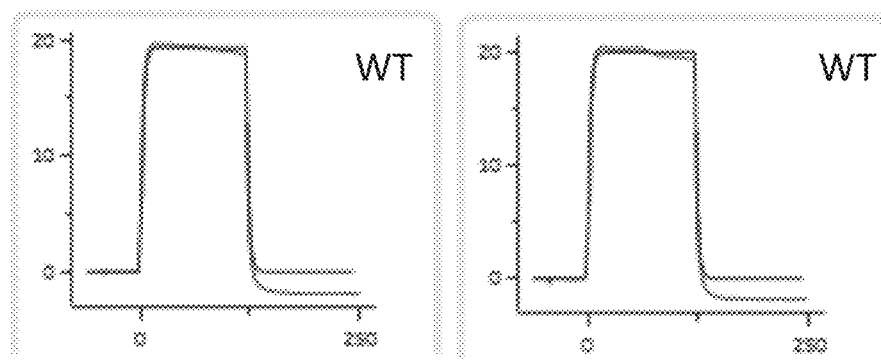
Time - sec

Time - sec

Time - sec

Time - sec

Time - sec

Time - sec

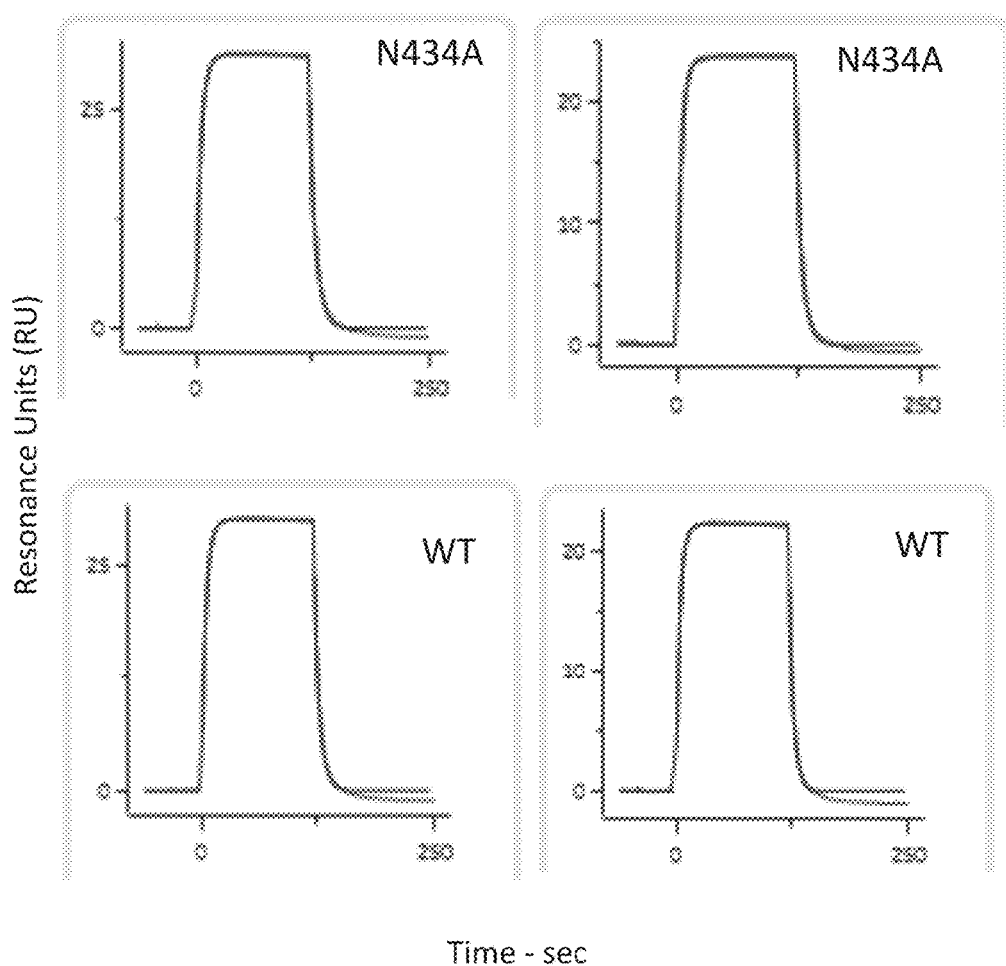

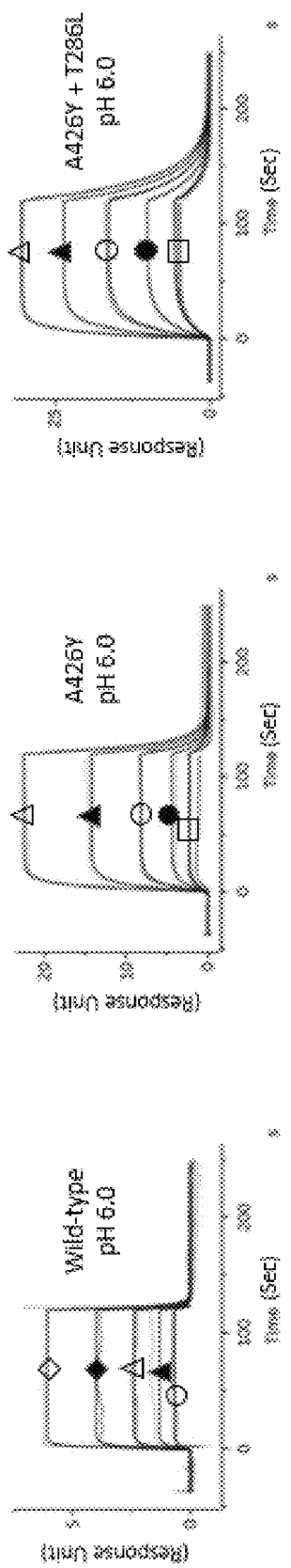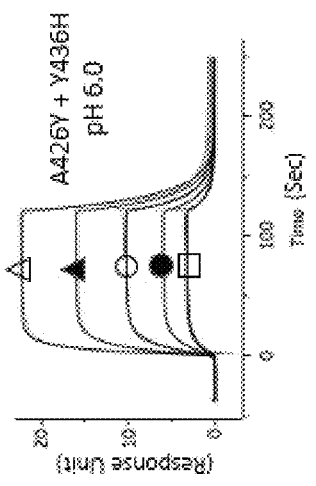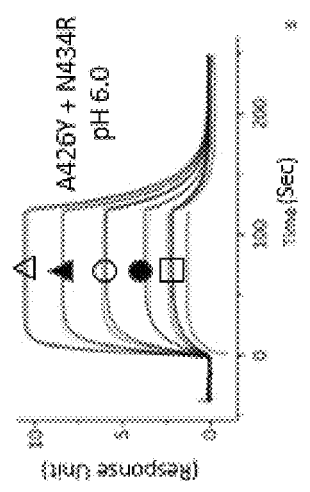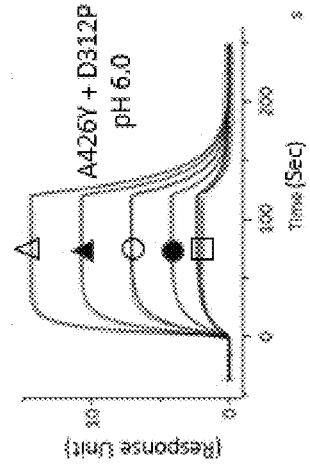
FIG. 20A  FIG. 20B  FIG. 20C  FIG. 20D  FIG. 20E  FIG. 20F

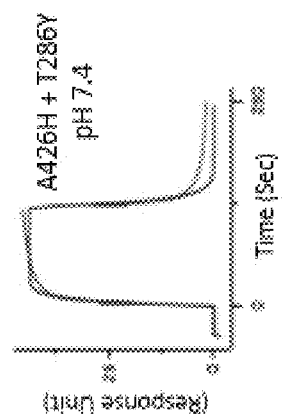
FIG. 25A
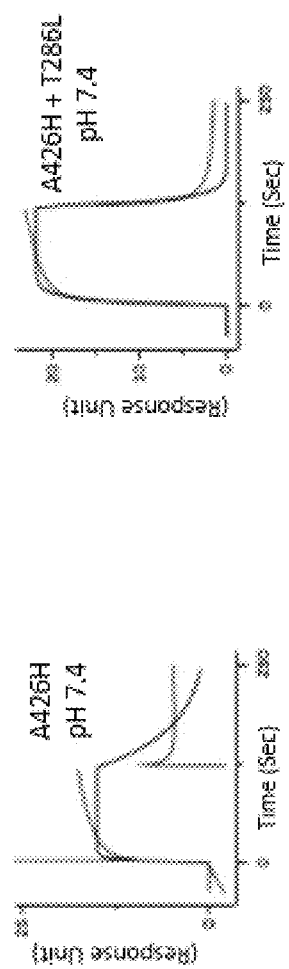
FIG. 25B
FIG. 25C
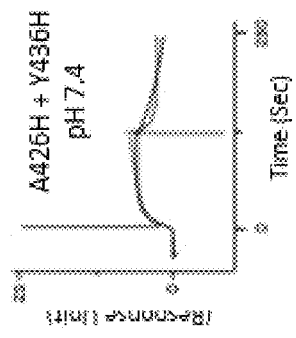
FIG. 25D
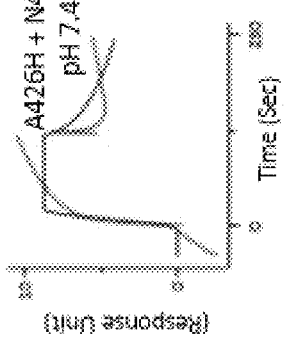
FIG. 25E
FIG. 25F

```
Canine IgGB       VFIFPPKPKD TLLIARTPEV TCVVVDLDPE DPEVQISWFV DGKQMQTAKT QPREEQFNGT YRVVSVLPIG
Human IgG1        VFLFPPKPKD TLMISRTPEV TCVVVDVSHE DPEVKFNWYV DGVEVHNAKT KPREEQYNST YRVVSVLTVL
                  240        250        260        270        280        290        300

Canine IgGB       HQDWLKGKQF TCKVNNKALP SPIERTISKA RGQAHQPSVY VLPPSREELS KNTVSLTCLI KDFFPPDIDV
Human IgG1        HQDWLNGKEY KCKVSNKALP APIEKTISKA KGQPREPQVY TLPPSREEMT KNQVSLTCLV KGFYPSDIAV
                  310        320        330        340        350        360        370

389a
                                 389b
                                 389c
                                 390
Canine IgGB       EWQSNGQQEP ESKYRTTPPQLD EDGSYFLYSK LSVDKSRWQR GDTFICAVMH EALHNHYTQE
Human IgG1        EWESNGQPEN   NYKTTPPVLD SDGSFFLYSK LTVDKSRWQQ GNVFSCSVMH EALHNHYTQK
                  380            400        410        420        430
```

FIG. 28

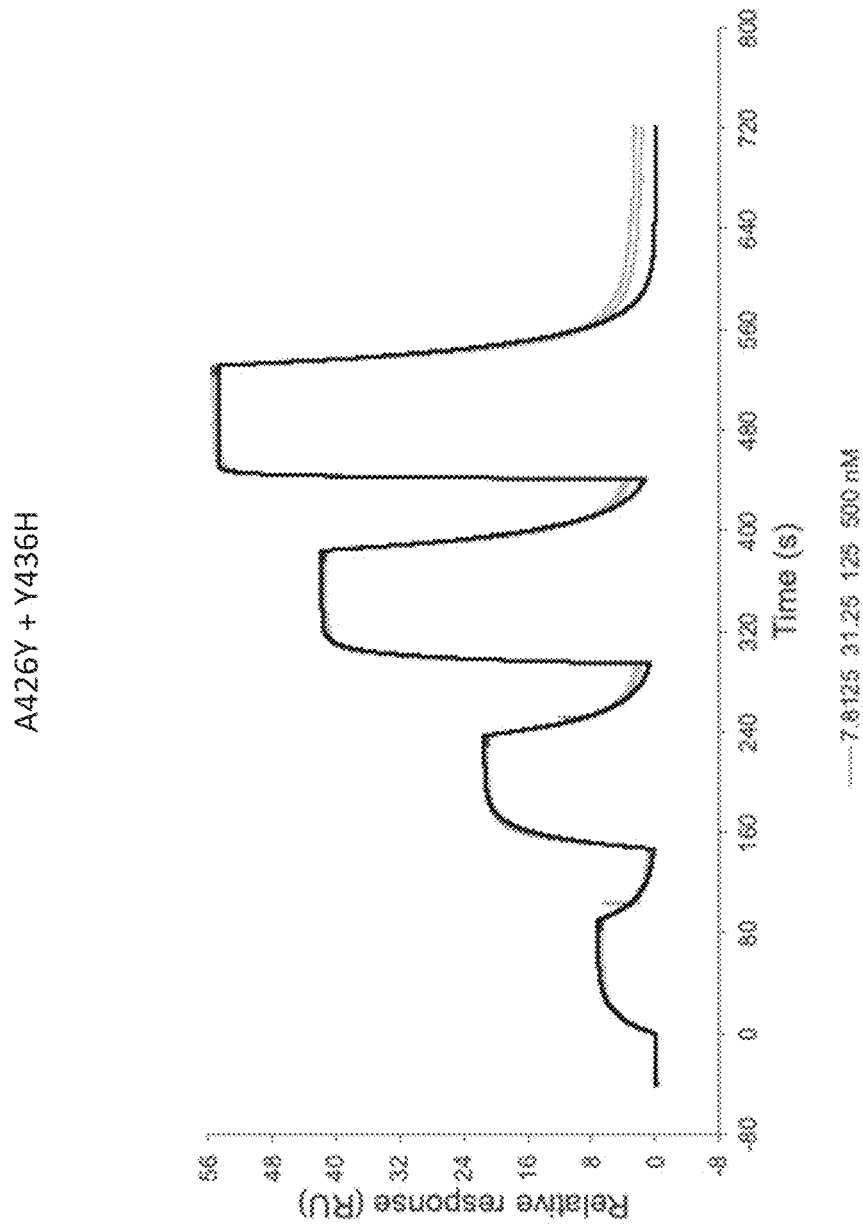

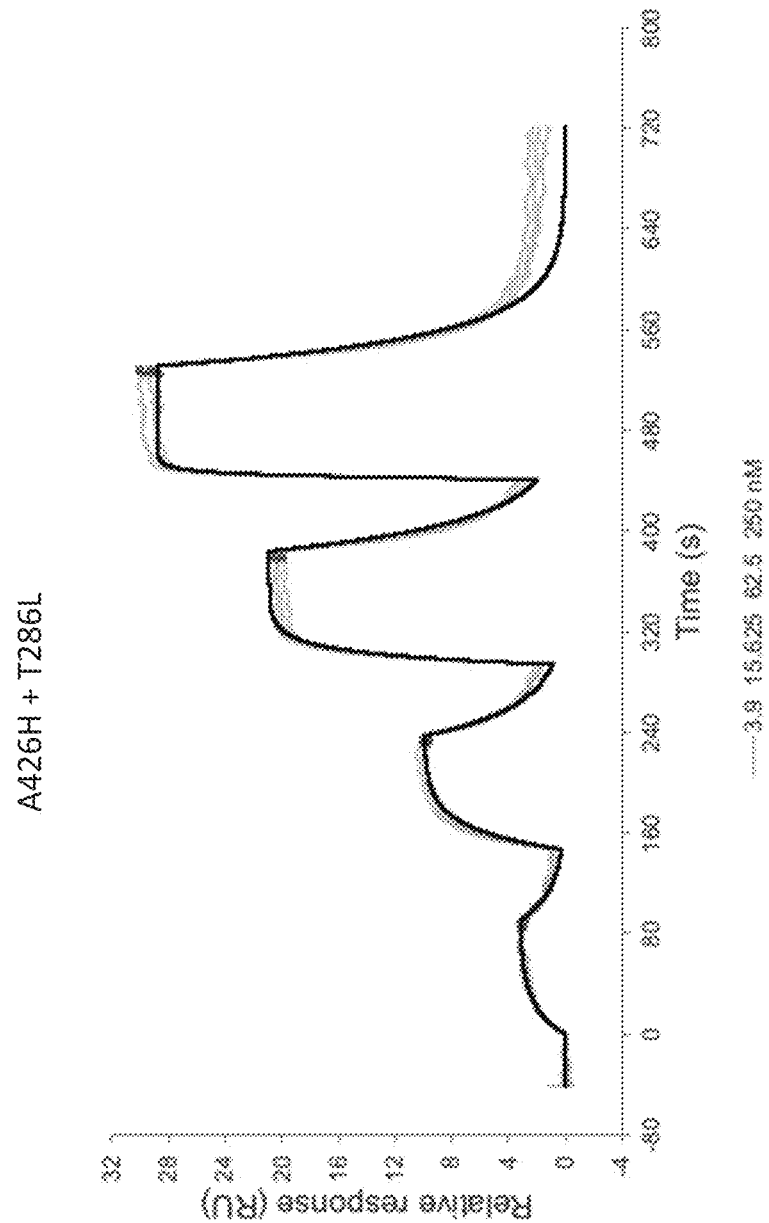

POLYPEPTIDES WITH ALTERED BINDING TO NEONATAL FC RECEPTOR (FCRN) AND METHODS OF USE

CROSS REFERENCE TO RELATED APPLICATIONS

This application claims priority to U.S. Provisional Application No. 63/023,083, filed May 11, 2020, and to U.S. Provisional Application No. 63/122,417, filed Dec. 7, 2020, the contents of each of which are incorporated by reference in their entireties.

FIELD

This disclosure relates generally to polypeptides (e.g., fusion polypeptides such as polypeptide-Fc region fusions; or binding molecules such as antibodies or ligand-binding portions of receptor-Fc fusions) that have increased half-life in canines compared to their wild type counterparts.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that is identified as follows:
File Name: 47406-0015001_Sequence_Listing.txt
Date of Creation: May 6, 2021
Size (bytes): 34,000 bytes

BACKGROUND

The Fc region of antibodies plays a number of functional roles, including, but not limited to, protecting the antibody from degradation through the lysosomal pathway and mediating antibody effector functions. With the increasing use of canine antibodies as therapeutic agents, there has been an enhanced focus on not just selecting an optimal Fab, but also combining it with an appropriate Fc for desired half-life and effector functions.

There is little guidance in the art relating to increasing half-life of polypeptide therapeutics (e.g., antibodies) for use in dogs. This disclosure remedies that failing by providing Fc region variants that improve the serum persistence of polypeptides (e.g., antibodies) in canines.

SUMMARY

Provided herein are canine Fc (e.g., canine IgG Fc region variant) or canine FcRn binding fragments thereof that are useful in therapeutic polypeptides. This disclosure features polypeptides that have increased binding to canine FcRn than control polypeptides (e.g., the wild type counterpart IgG canine Fc regions). In some instances, these polypeptides have increased binding to canine FcRn than control polypeptides at pH 5.5, pH 6.0 and/or pH 6.5. In some instances, these polypeptides can, e.g., bind to canine FcRn at a higher level at acidic pH (e.g., pH 5.5, pH 6.0 or pH 6.5) than at a neutral pH (e.g., pH 7.0, 7.1, 7.2, 7.3, 7.4, or 7.5). In some instances, these polypeptides bind to canine FcRn at a higher level at pH 5.5 and/or 6.0 than at pH 7.4. This disclosure relates, in part, to polypeptides that have increased half-life in canines than their wild type counterparts. For example, provided are binding molecules (e.g., antibodies or ligand-binding portions of receptors) with increased half-life relative to versions of these binding molecules not attached to the Fc regions or canine FcRn binding regions thereof disclosed herein. Also provided are enzyme-Fc region fusions, ligand-Fc region fusions, nanobody-Fc fusions, and peptide-Fc region fusions, wherein the fusions have increased half-life compared with their wild type counterparts. The Fc regions, in addition to having a substitution or substitutions (relative to the wild type canine Fc region) that increase half-life may also include other substitutions that, e.g., increase effector function, decrease effector function, increase binding to Protein A and/or decrease heterogeneity of the polypeptide (e.g., by removing one or more post-translational modifications in the Fc region). The canine Fc region sequences can be from any canine antibody. In some instances, the canine Fc region sequences are from a canine IgG (e.g., IgGA, IgGB, IgGC, or IgGD).

The disclosure features a recombinant protein comprising (1) a binding domain, or a fragment thereof, that specifically binds to a ligand, or an epitope of a protein, wherein the binding domain is attached to (2) a domain comprising an Fc region (CH2+CH3 region) or a canine FcRn binding region thereof, as disclosed herein. In some instances, the binding domain comprises (i) the six complementarity determining regions (CDRs) of a canine or human/humanized antibody; (ii) a nanobody; (iii) a soluble receptor-binding domain that binds a ligand, or a ligand-binding fragment thereof and (iv) an extracellular domain of a canine receptor protein.

The disclosure also provides a composition comprising: (1) a first polypeptide comprising a first Fc region (e.g., a CH2 region, a CH3 region, a CH2+CH3 region) comprising a canine IgG Fc region variant described herein; and (2) a second polypeptide comprising a second Fc region comprising a canine IgG Fc region variant described herein. The first and second polypeptide can be associated through the first and second Fc regions. In some instances, the amino acid sequences of the first and second Fc regions are the same. In other instances, the amino acid sequences of the first and second Fc regions are different (e.g., by 1, 2, 3, 4, 5, 6, 7, 8, 9, 10, 11, 12, 13, 14, 15, 16, 17, 18, 19, 20, 21, 22, 23, 24, or 25 amino acids). In some instances, the Fc region variant is a variant of a canine IgGB antibody Fc region. In some instances, the Fc region variant is a variant of a canine IgGA antibody Fc region. In some instances, the Fc region variant is a variant of a canine IgGC antibody Fc region. In some instances, the Fc region variant is a variant of a canine IgGD antibody Fc region.

Also disclosed is a fusion molecule comprising a canine IgG Fc region variant disclosed herein and a polypeptide. In some instances, the canine IgG Fc region variant is covalently attached to the polypeptide (e.g., through a hinge region or a linker). In some instances, the polypeptide is a ligand binding domain of a canine receptor protein, an extracellular domain of a canine receptor protein, or an antigen-binding domain. In some instances, the polypeptide is selected from the ligand binding domain or extracellular domain of canine IL-13Rα1, or IL-13Rα2, canine EPO, canine CTLA4, canine LFA3, canine VEGFR1/VEGFR3, canine IL-1R, canine GLP-1 receptor agonist, and canine Thrombopoietin binding peptide. In some instances, the polypeptide is a scFv, a nanobody, or single domain antibody. In some instances, the IgG Fc region variant is a variant of a canine IgGB antibody Fc region. In some instances, the IgG Fc region variant is a variant of a canine IgGA antibody Fc region. In some instances, the IgG Fc region variant is a variant of a canine IgGC antibody Fc region. In some instances, the IgG Fc region variant is a variant of a canine IgGD antibody Fc region.

In some aspects, the disclosure provides polypeptides comprising a canine IgG Fc region variant, or a canine FcRn-binding region thereof, wherein the polypeptide comprises at least one amino acid substitution at a position selected from the group consisting of:
a position that corresponds to amino acid position 286 of a wild type canine IgG; a position that corresponds to amino acid position 312 of a wild type canine IgG; a position that corresponds to amino acid position 426 of a wild type canine IgG; and a position that corresponds to amino acid position 436 of a wild type canine IgG; wherein the amino acid substitution that corresponds to amino acid position 286 of the wild type canine IgG is selected from the group consisting of Tyr, Phe, Leu and Trp, wherein the amino acid positions are based on EU numbering, and wherein the polypeptide has increased binding affinity to canine FcRn when compared to an Fc domain of the wild type canine IgG.

In some embodiments, the polypeptide comprises Pro at the amino acid position that corresponds to amino acid position 312 of the wild type canine IgG.

In some embodiments, the polypeptide comprises Tyr, His or Phe at the amino acid position that corresponds to amino acid position 426 of the wild type canine IgG.

In some embodiments, the polypeptide comprises His at the position that corresponds to amino acid position 436 of a wild type canine IgG.

In some embodiments, the polypeptide comprises at least one additional amino acid substitution at a position selected from the group consisting of:
an amino acid position that corresponds to amino acid position 250 of the wild type canine IgG,
an amino acid position that corresponds to amino acid position 251 of the wild type canine IgG,
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG,
an amino acid position that corresponds to amino acid position 285 of the wild type canine IgG,
an amino acid position that corresponds to amino acid position 286 of the wild type canine IgG,
an amino acid position that corresponds to amino acid position 307 of the wild type canine IgG,
an amino acid position that corresponds to amino acid position 308 of the wild type canine IgG,
an amino acid position that corresponds to amino acid position 309 of the wild type canine IgG,
an amino acid position that corresponds to amino acid position 311 of the wild type canine IgG,
an amino acid position that corresponds to amino acid position 315 of the wild type canine IgG,
an amino acid position that corresponds to amino acid position 378 of the wild type canine IgG,
an amino acid position that corresponds to amino acid position 380 of the wild type canine IgG,
an amino acid position that corresponds to amino acid position 428 of the wild type canine IgG,
an amino acid position that corresponds to amino acid position 430 of the wild type canine IgG,
an amino acid position that corresponds to amino acid position 433 of the wild type canine IgG,
an amino acid position that corresponds to amino acid position 434 of the wild type canine IgG, and
an amino acid position that corresponds to amino acid position 435 of the wild type canine IgG.

In some embodiments, the polypeptide comprises:
Glu or Gln at the amino acid position that corresponds to amino acid position 250 of the wild type canine IgG,
Asp or Glu at the amino acid position that corresponds to amino acid position 251 of the wild type canine IgG,
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG,
Asn or Asp at the amino acid position that corresponds to amino acid position 285 of the wild type canine IgG,
Asp, Tyr, Phe, Leu or Trp at the amino acid position that corresponds to amino acid position 286 of the wild type canine IgG,
Arg, Gln or Ala at the amino acid position that corresponds to amino acid position 307 of the wild type canine IgG,
Pro at the amino acid position that corresponds to amino acid position 308 of the wild type canine IgG,
Pro at the amino acid position that corresponds to amino acid position 309 of the wild type canine IgG,
Val at the amino acid position that corresponds to amino acid position 311 of the wild type canine IgG,
Asp at the amino acid position that corresponds to amino acid position 315 of the wild type canine IgG,
Val at the amino acid position that corresponds to amino acid position 378 of the wild type canine IgG,
Ala at the amino acid position that corresponds to amino acid position 380 of the wild type canine IgG,
Leu at the amino acid position that corresponds to amino acid position 428 of the wild type canine IgG,
Ala or Lys at the amino acid position that corresponds to amino acid position 430 of the wild type canine IgG,
Lys at the amino acid position that corresponds to amino acid position 433 of the wild type canine IgG,
Trp, Tyr, Arg, His, Ser, Ala or Phe at the amino acid position that corresponds to amino acid position 434 of the wild type canine IgG, and/or
Tyr at the amino acid position that corresponds to amino acid position 435 of the wild type canine IgG.

In some embodiments, the at least one additional amino acid substitution is at a position selected from the group consisting of:
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG, and
an amino acid position that corresponds to amino acid position 434 of the wild type canine IgG.

In some embodiments, the polypeptide comprises:
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG, and/or
Trp, Tyr, Arg, His, Ser, Ala or Phe at the amino acid position that corresponds to amino acid position 434 of the wild type canine IgG.

In some embodiments, the polypeptide comprises:
Tyr at the amino acid position that corresponds to amino acid position 252 of the wild type canine IgG,
Thr at the amino acid position that corresponds to amino acid position 254 of the wild type canine IgG,
Glu at the amino acid position that corresponds to amino acid position 256 of the wild type canine IgG, and/or
Trp, Tyr, Arg or His at the amino acid position that corresponds to amino acid position 434 of the wild type canine IgG.

In some aspects, the disclosure provides polypeptides comprising a canine IgG Fc region variant, or a canine FcRn-binding region thereof, wherein the polypeptide comprises amino acid substitutions at two or more positions selected from the group consisting of:
a position that corresponds to amino acid position 286 of a wild type canine IgG;
a position that corresponds to amino acid position 312 of a wild type canine IgG;
a position that corresponds to amino acid position 426 of a wild type canine IgG;
a position that corresponds to amino acid position 434 of a wild type canine IgG; and
a position that corresponds to amino acid position 436 of a wild type canine IgG,
wherein the amino acid positions are based on EU numbering, and wherein the polypeptide has increased binding affinity to canine FcRn when compared to an Fc domain of the wild type canine IgG.

In some embodiments, the amino acid substitution at the position that corresponds to amino acid position 286 of a wild type canine IgG is selected from the group consisting of T286L, T286Y and conservative amino acid substitutions of any of foregoing.

In some embodiments, the amino acid substitution at the position that corresponds to amino acid position 312 of a wild type canine IgG is D312P or a conservative amino acid substitution thereof.

In some embodiments, the amino acid substitution at the position that corresponds to amino acid position 426 of a wild type canine IgG is selected from the group consisting of A426Y, A426H and conservative amino acid substitutions of any of foregoing.

In some embodiments, the amino acid substitution at the position that corresponds to amino acid position 434 of a wild type canine IgG is N434R or a conservative amino acid substitution thereof.

In some embodiments, the amino acid substitution at the position that corresponds to amino acid position 436 of a wild type canine IgG is Y436H or a conservative amino acid substitution thereof.

In some embodiments, the polypeptide comprises an amino acid substitution at the position that corresponds to amino acid position 426 of a wild type canine IgG, wherein the polypeptide comprises amino acid substitutions at the two or more positions selected from the group consisting of:
positions that correspond to amino acid positions 426 and 286 of a wild type canine IgG;
positions that correspond to amino acid position 426 and 312 of a wild type canine IgG;
positions that correspond to amino acid position 426 and 434 of a wild type canine IgG;
positions that correspond to amino acid position 426 and 436 of a wild type canine IgG; and
positions that correspond to amino acid position 286, 426 and 436 of a wild type canine IgG.

In some embodiments, the polypeptide comprises amino acid substitutions selected from the group consisting of:
A426Y and T286L;
A426Y and D312P;
A426Y and Y436H;
A426H and T286L;
A426H and T286Y;
A426H and D312P; and
T286L, A426Y, and Y436H.

In some embodiments, the two or more amino acid substitutions are selected from the group consisting of:
A426Y in combination with one or more of T286L, D312P, N434R and Y436H;
A426H in combination with one or more of T286L, T286Y, D312P, N434R and Y436H; and
N434R in combination with one or more of T286L, T286Y, D312P and Y436H.

In some embodiments, the wild type canine IgG is a canine IgGA comprising an Fc domain having an amino acid sequence that is at least 95% identical to SEQ ID NO: 9, a canine IgGB comprising an Fc domain having an amino acid sequence that is at least 95% identical to SEQ ID NO: 10, a canine IgGC comprising an Fc domain having an amino acid sequence that is at least 95% identical to SEQ ID NO: 11, or a canine IgGD comprising an Fc domain having amino acid sequence that is at least 95% identical to SEQ ID NO: 12.

In some embodiments, the polypeptide further comprises a binding domain comprising (i) six complementarity determining regions (CDRs) of an immunoglobulin molecule; (ii) a ligand binding domain of a canine receptor protein, (iii) a nanobody, or (iv) an extracellular domain of a canine receptor protein.

In some embodiments, the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

In some embodiments, the polypeptide further comprises a protein selected from the group consisting of EPO, CTLA4, LFA3, VEGFR1/VEGFR3, IL-1R, IL-4R, GLP-1 receptor agonist, and Thrombopoietin binding peptide.

In some embodiments, the polypeptide has: (1) increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant; and/or (2) increased binding to canine FcRn than the control polypeptides; and wherein the amino acid positions are based on EU numbering.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:9.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:10.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:11.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:12.

In some embodiments, the polypeptide binds to a canine FcRn at a higher level at an acidic pH than at a neutral pH in a binding assay.

In some embodiments, the polypeptide binds to a canine FcRn at a higher level at an acidic pH than at a neutral pH. In some embodiments, the polypeptide binds to a canine FcRn at a higher level at pH 5.5 than at pH 7.4. In some embodiments, the polypeptide binds to a canine FcRn at a higher level at pH 6.0 than at pH 7.4.

In some aspects, the disclosure provides pharmaceutical compositions comprising (i) any of the polypeptides described herein, and (ii) a pharmaceutically acceptable excipient.

In some aspects, the disclosure provides a nucleic acid or nucleic acids encoding any of the polypeptides described herein.

In some aspects, the disclosure provides an expression vector or expression vectors comprising any of the nucleic acid or nucleic acids described herein.

In some aspects, the disclosure provides host cells comprising a nucleic acid or nucleic acids, or an expression vector or expression vectors comprising a nucleic acid or nucleic acids encoding a polypeptide comprising a canine IgG Fc region variant, or a canine FcRn-binding region thereof, wherein the polypeptide comprises at least one amino acid substitution at a position selected from the group consisting of:

a position that corresponds to amino acid position 286 of a wild type canine IgG;
a position that corresponds to amino acid position 312 of a wild type canine IgG;
a position that corresponds to amino acid position 426 of a wild type canine IgG; and
a position that corresponds to amino acid position 436 of a wild type canine IgG;
wherein the amino acid substitution that corresponds to amino acid position 286 of the wild type canine IgG is selected from the group consisting of Tyr, Phe, Leu and Trp, wherein the amino acid positions are based on EU numbering, and wherein the polypeptide has increased binding affinity to canine FcRn when compared to an Fc domain of the wild type canine IgG.

In some aspects, the disclosure provides a host cell comprising the nucleic acid or nucleic acids described herein or the expression vector or expression vectors described herein.

In some aspects, the disclosure provides a method of making a polypeptide or polypeptides, the method comprising:

(a) providing a nucleic acid or nucleic acids described herein;
(b) expressing the nucleic acid or nucleic acids in a host cell culture, thereby producing the polypeptide; and
(c) collecting the polypeptide produced in (b) from the host cell culture.

In some embodiments, the method further comprises formulating the polypeptide as a pharmaceutical formulation.

In some aspects, the disclosure provides a method of treating a canine disease or disorder in a dog in need thereof, the method comprising administering an effective amount of a composition comprising the pharmaceutical composition described herein to the dog.

In some aspects, the disclosure provides a method of preventing a canine disease or disorder in a dog in need thereof, the method comprising administering an effective amount of a composition comprising the pharmaceutical composition described herein to the dog.

In some embodiments, the disease or disorder is an allergic disease, a chronic pain, an acute pain, an inflammatory disease, an autoimmune disease, an endocrine disease, a gastrointestinal disease, a cardiovascular disease, a renal disease, a fertility related disorder, an infectious disease or a cancer.

In some embodiments, the disease or disorder is atopic dermatitis, allergic dermatitis, osteoarthritic pain, arthritis, anemia, or obesity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF DRAWINGS

The patent application file contains at least one drawing executed in color. Copies of this patent application publication with color drawing(s) will be provided by the Office upon request and payment of the necessary fee.

FIG. 1 is an amino acid sequence alignment of canine IgG γ chains. These chains contain $V_H$, CH1, CH2, and CH3 domains and the hinge region between CH1 and CH2. An N-glycosylation site is shown in bold and marked in a block. These sequences are assigned SEQ ID NOs.: 13, 14, 15, and 16, respectively.

FIG. 2 is an amino acid sequence alignment of the CH2 region of canine IgG γ chains. These sequences are assigned SEQ ID NOs.: 1, 2, 3, and 4, respectively. Residues that are substituted to increase half-life are identified by underlines.

FIG. 3 is an amino acid sequence alignment of the CH3 region of canine IgG γ chains. These sequences are assigned SEQ ID NOs.: 5, 6, 7, and 8, respectively. Residues that are substituted to increase half-life are identified by underlines.

FIG. 4 is an amino acid sequence alignment of the Fc region of canine IgG γ chains. These sequences are assigned SEQ ID NOs.: 9, 10, 11, and 12, respectively. Residues that are substituted to increase half-life are identified by underlines.

FIG. 5 is a table provided EU numbering for the CH2 region of canine IgG.

FIG. 6 is a table provided EU numbering for the CH3 region of canine IgG.

FIGS. 8A-8C depict Biacore sensorgrams for wild type and the different variants from the NNK libraries at position 250. The lighter line on each figure represents the measured data and the darker line is the fitted curve using a 1:1 interaction model.

FIGS. 15A-15F depict Biacore sensorgrams for wild type and the different variants from the NNK libraries at position 434. The lighter line represents the measured data and the darker line represents the fitted curve using a 1:1 interaction model.

FIGS. 20A-20F show Biacore sensorgrams for wild-type canine IgGB Fc, single (A426Y) and combination variants of canine IgGB Fc binding to canine FcRn at pH 6.0. The concentrations of canine FcRn used for wild-type IgG were 200 nM (white circle), 400 nM (black triangle), 800 nM (white triangle), 1600 nM (black diamond), and 3200 nM (white diamond). The concentrations of canine FcRn for the remaining variants was 50 nM (white square), 100 nM (black circle), 200 nM, (white circle), 400 nM (black triangle) and 800 nM (white triangle). The lighter line in each sensorgram represents the measured data and the darker line represents the fitted curve using a 1:1 interaction model.

FIGS. 25A-25F show Biacore sensorgrams for single (A426H) and combination variants of IgGB Fc binding to canine FcRn at pH 7.4. The lighter line in each sensorgram represents the measured data and the darker line represents the fitted curve using a 1:1 interaction model.

FIG. 28 is an amino acid sequence alignment of canine IgGB Fc with human IgG1 Fc. The positions (according to EU numbering) at which amino acid substitutions were made to generate the canine Fc variants are underlined.

FIGS. 30A-30K show the Biacore sensorgram for the binding of different variants of IgGB to canine FcRn at pH 5.9.

DETAILED DESCRIPTION

Figure 7A:
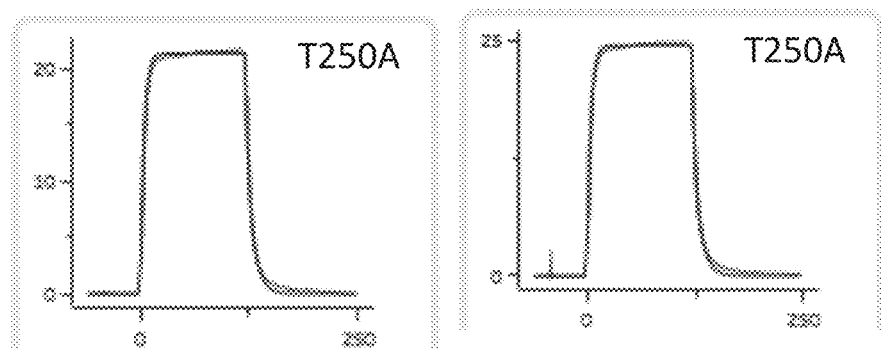
FIGS. 7A-7U depict Biacore sensorgrams from the alanine scanning mutagenesis experiment. The lighter line on each figure represents the measured data and the darker line represents the fitted curve using a 1:1 interaction model.
Figure 7B:
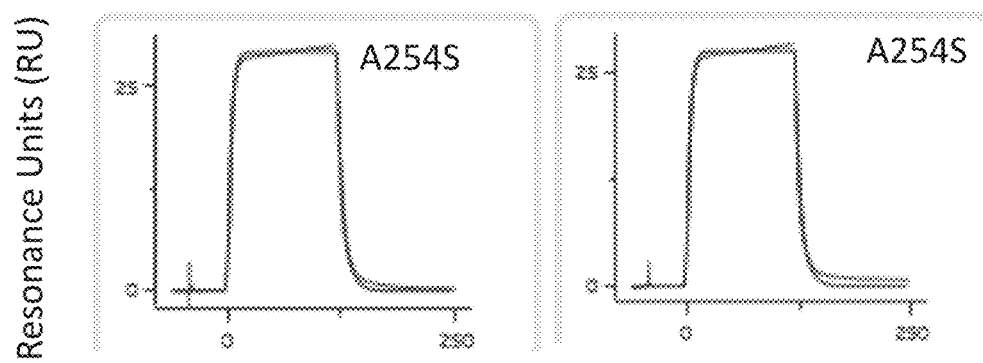
Figure 7C:
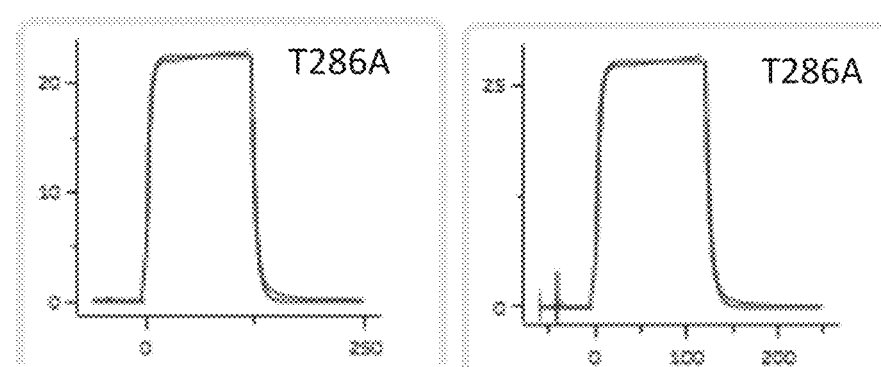
Figure 7D:
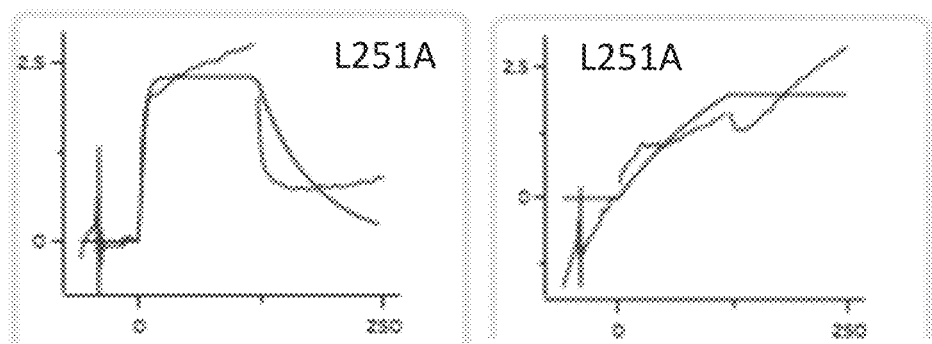
Figure 7E:
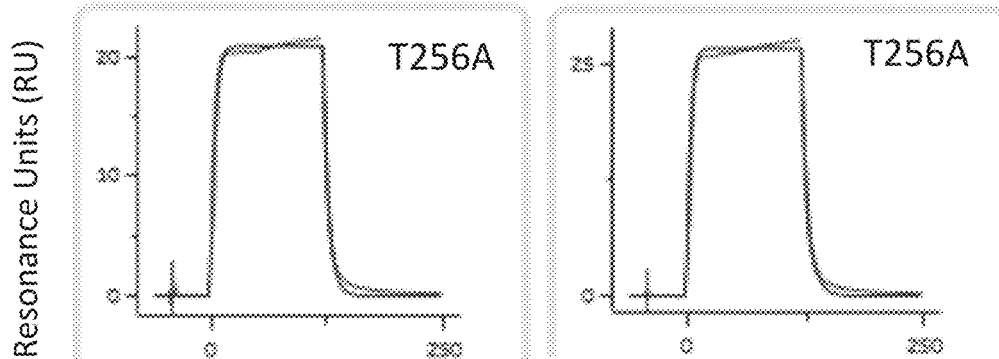
Figure 7F:
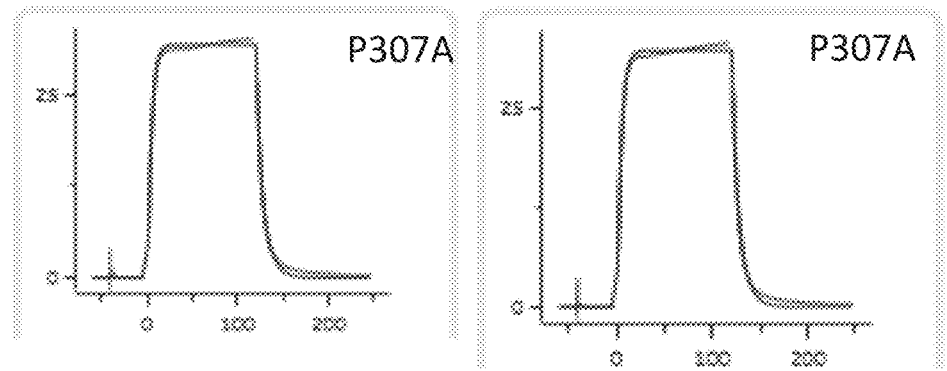
Figure 7G:
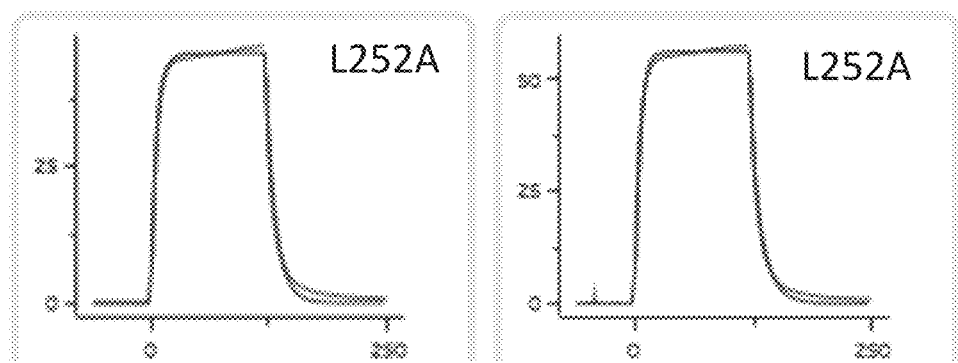
Figure 7H:
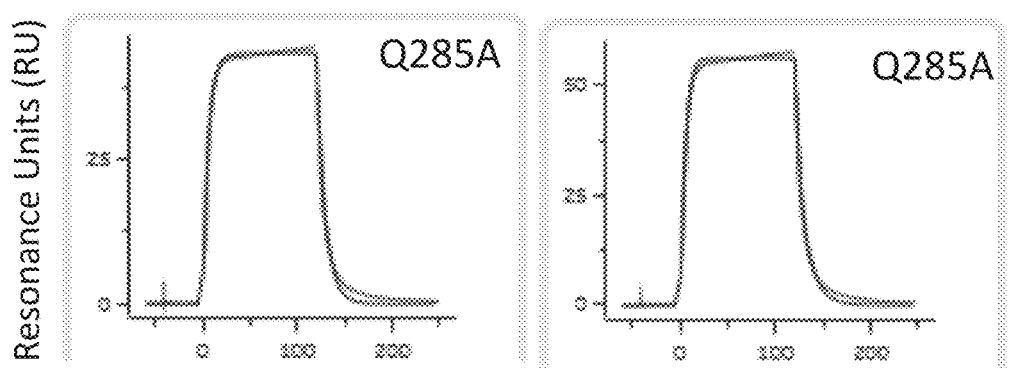
Figure 7I:
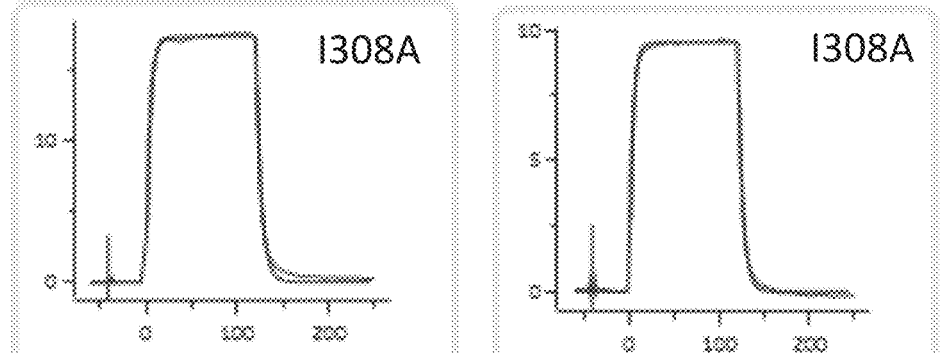
Figure 7J:
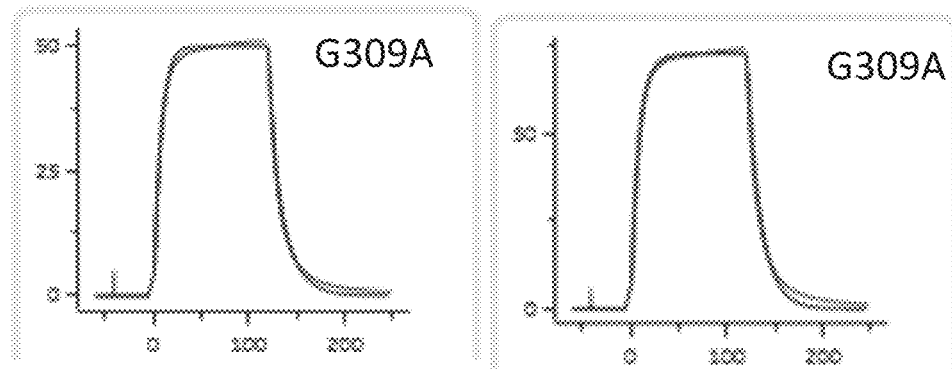
Figure 7K:
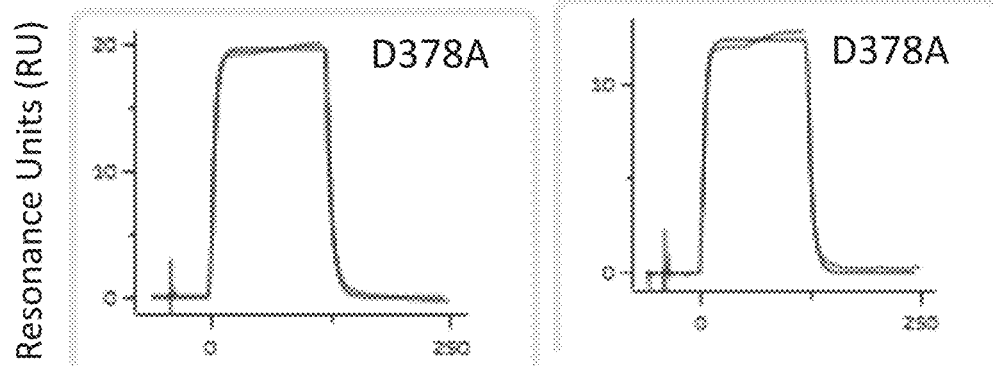
Figure 7L:
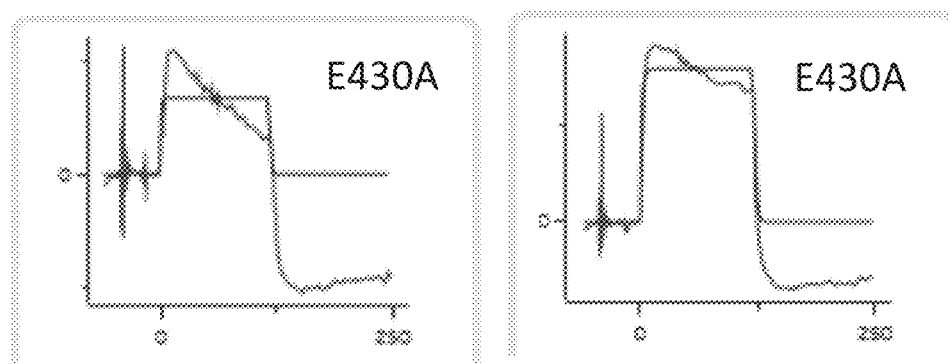
Figure 7M:
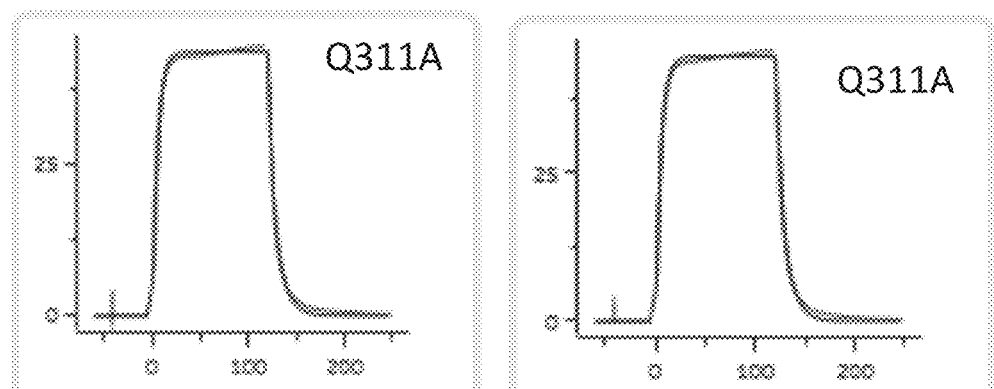
Figure 7N:
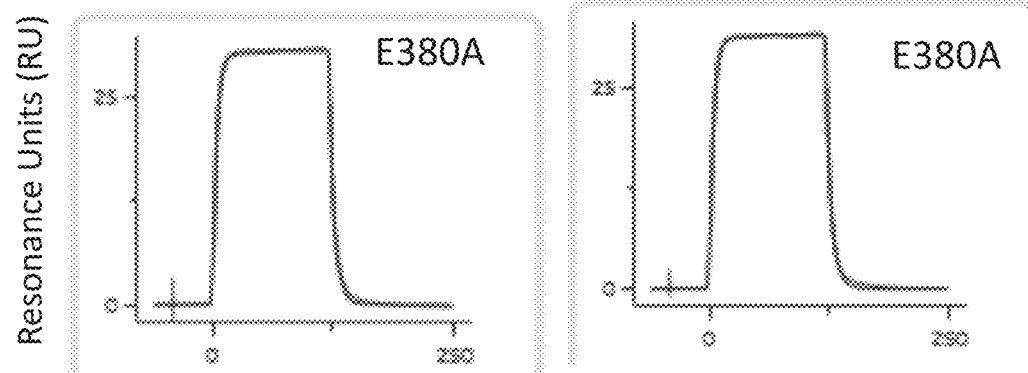
Figure 7O:
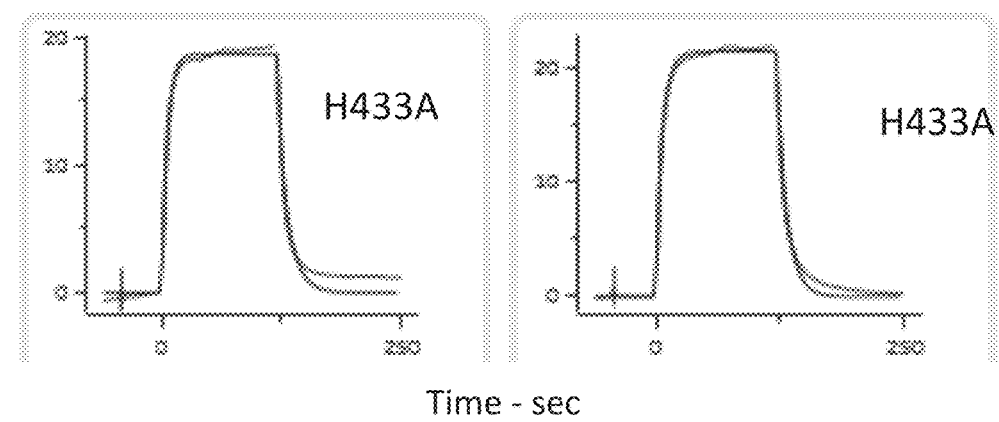
Figure 7P:
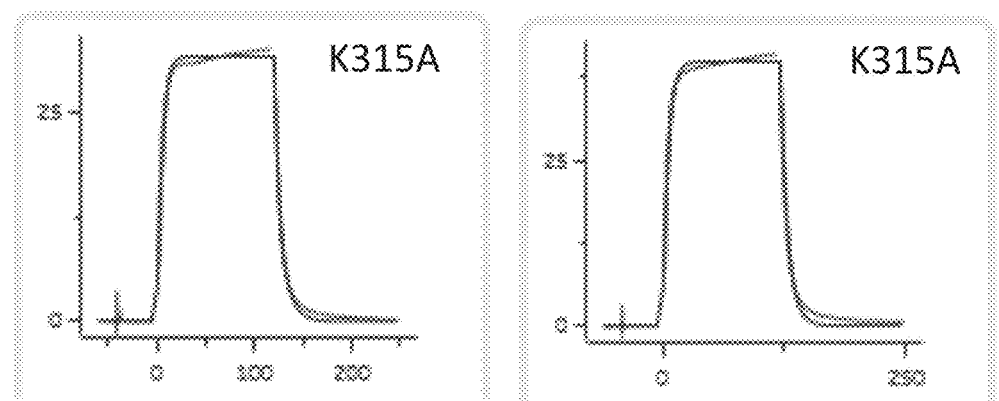
Figure 7Q:
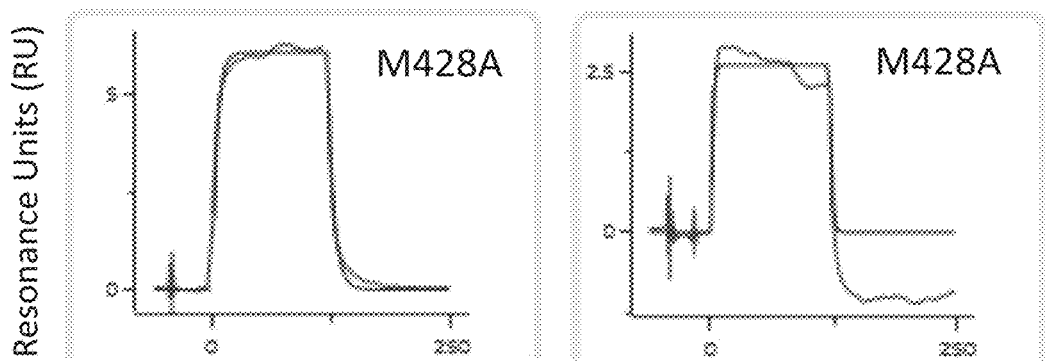
Figure 7R:
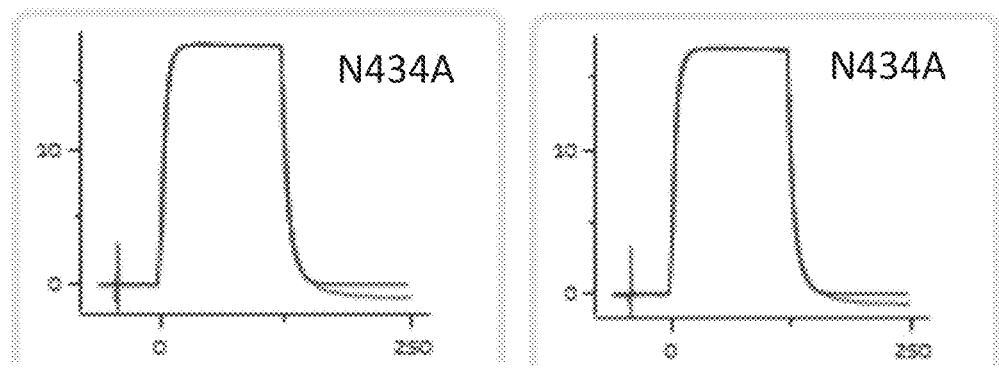
Figure 7S:
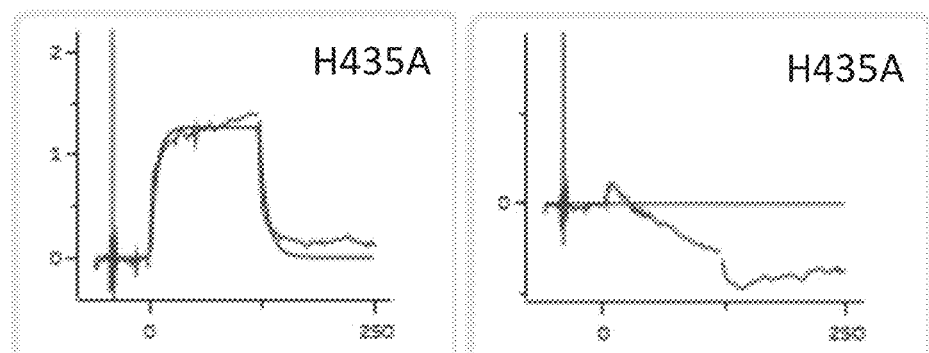
Figure 7T:
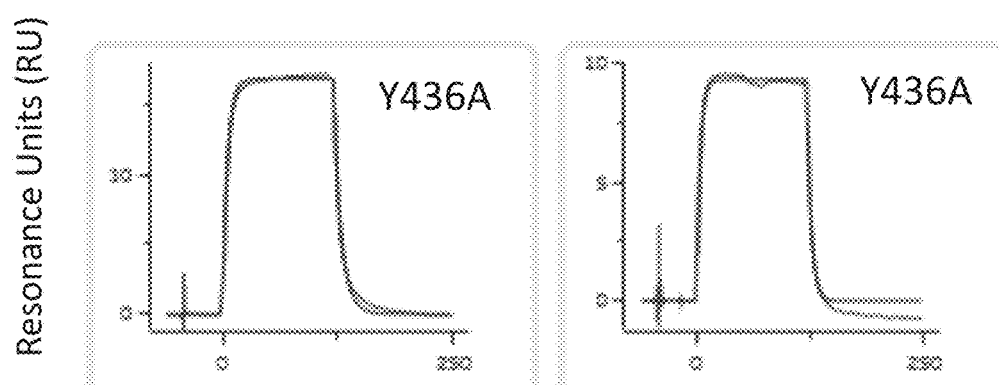

With the increasing use of polypeptide (e.g., antibodies, ligand-binding domains of receptors, enzymes, ligands, peptides) as therapeutics for the prevention and treatment of a wide variety of canine diseases, it is important to develop polypeptides with extended half-life, especially for the prevention or treatment of chronic diseases in which a polypeptide must be administered repetitively.

Accordingly, this disclosure features canine immunoglobulin Fc regions or canine FcRn-binding regions thereof comprising mutations that enhance the half-life of a polypeptide or polypeptides comprising these sequences. Also disclosed are polypeptides comprising these domains and methods of their use. These peptides can be used for various therapeutic and diagnostic purposes.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated. All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

Canine Antibodies

Dogs have four IgG heavy chains referred to as A, B, C, and D. These heavy chains represent four different subclasses of dog IgG, which are referred to as IgGA, IgGB, IgGC and IgGD. The amino acid and DNA sequences for these heavy chains are available from Tang et al., *Vet. Immunol. Immunopathol.,* 80: 259-270 (2001) and the GENBANK database. For example, the amino acid sequence of IgGA heavy chain has GENBANK accession number AAL35301.1, IgGB has GENBANK accession number AAL35302.1, IgGC has GENBANK accession number AAL35303.1, and IgGD has GENBANK accession number AAL35304.1. Canine antibodies also include two types of light chains: kappa and lambda. The DNA and amino acid sequence of these light chains can also be obtained from GENBANK database. For example, the dog kappa light chain amino acid sequence has accession number ABY57289.1 and the dog lambda light chain has accession number ABY55569.1.

CH2 Region of a Canine Fc Region:

The CH2 region of a canine antibody comprises or consists of amino acids 237 to 340 (according to EU numbering) of a canine IgG antibody. It is to be understood that the CH2 region may include one to six (e.g., 1, 2, 3, 4, 5, 6) additional amino acids or deletions at their N and/or C-terminus.

The amino acid sequence of the CH2 region of canine IgGA is provided below:

```
                                            (SEQ ID NO: 1)
GPSVLI FPPKPKDILR ITRTPEVTCV VLDLGREDPE

VQISWFVDGK EVHTAKTQSR EQQFNGTYRV VSVLPIEHQD

WLTGKEFKCR VNHIDLPSPI ERTISKAR
```

The amino acid sequence of the CH2 domain of canine IgGB is provided below:

```
                                            (SEQ ID NO: 2)
GPSVFIFPPK PKDTLLIART PEVTCVVVDL DPEDPEVQIS

WFVDGKQMQT AKTQPREEQF NGTYRVVSVL PIGHQDWLKG

KQFTCKVNNK ALPSPIERTI SKAR
```

The amino acid sequence of the CH2 domain of canine IgGC is provided below:

```
                                            (SEQ ID NO: 3)
GPSVFIFPP KPKDILVTAR TPTVTCVVVD LDPENPEVQI

SWFVDSKQVQ TANTQPREEQ SNGTYRVVSV LPIGHQDWLS

GKQFKCKVNN KALPSPIEEI ISKTP
```

The amino acid sequence of the CH2 domain of canine IgGD is provided below:

```
                                            (SEQ ID NO: 4)
GPSV FIFPPKPKDI LRITRTPEIT CVVLDLGRED

PEVQISWFVD GKEVHTAKTQ PREQQFNSTY RVVSVLPIEH

QDWLTGKEFK CRVNHIGLPS PIERTISKAR
```

CH3 Region of a Canine Fc Region:

The CH3 region of a canine antibody comprises or consists of amino acids 345 to 447 (according to EU numbering) of a canine IgG antibody. It is to be understood that the CH3 region may include one to six (e.g., 1, 2, 3, 4, 5, 6) additional amino acids or deletions at their N and/or C-terminus.

The amino acid sequence of the CH3 domain of canine IgGA is provided below:

```
                                        (SEQ ID NO: 5)
KPSVYVLP PSPKELSSSD TVSITCLIKD FYPPDIDVEW

QSNGQQEPER KHRMTPPQLD EDGSYFLYSK LSVDKSRWQQ

GDPFTCAVMH ETLQNHYTDL SLSHSPGK
```

The amino acid sequence of the CH3 domain of canine IgGB is provided below:

```
                                        (SEQ ID NO: 6)
QP SVYVLPPSRE ELSKNTVSLT CLIKDFFPPD IDVEWQSNGQ

QEPESKYRTT PPQLDEDGSY FLYSKLSVDK SRWQRGDTFI

CAVMHEALHN HYTQESLSHS PGK
```

The amino acid sequence of the CH3 domain of canine IgGC is provided below:

```
                                        (SEQ ID NO: 7)
Q PNVYVLPPSR DEMSKNTVTL TCLVKDFFPP EIDVEWQSNG

QQEPESKYRM TPPQLDEDGS YFLYSKLSVD KSRWQRGDTF

ICAVMHEALH NHYTQISLSH SPGK
```

The amino acid sequence of the CH3 domain of canine IgGD is provided below:

```
                                        (SEQ ID NO: 8)
QPSVYV LPPSPKELSS SDTVTLTCLI KDFFPPEIDV EWQSNGQPEP

ESKYHTTAPQ LDEDGSYFLY SKLSVDKSRW QQGDTFTCAV

MHEALQNHYT DLSLSHSPGK
```

Fc Region of a Canine Fc Region:

The Fc region of a canine IgG antibody comprises or consists of amino acids 231 to 447 (according to EU numbering) of the canine IgG antibody.

The amino acid sequence of the Fc domain of canine IgGA is provided below:

```
                                        (SEQ ID NO: 9)
VPEPLGGPSVLI FPPKPKDILR ITRTPEVTCV VLDLGREDPE

VQISWFVDGK EVHTAKTQSR EQQFNGTYRV VSVLPIEHQD

WLTGKEFKCR VNHIDLPSPI ERTISKARGR AHKPSVYVLP

PSPKELSSSD TVSITCLIKD FYPPDIDVEW QSNGQQEPER

KHRMTPPQLD EDGSYFLYSK LSVDKSRWQQ GDPFTCAVMH

ETLQNHYTDL SLSHSPGK
```

The amino acid sequence of the Fc domain of canine IgGB is provided below:

```
                                        (SEQ ID NO: 10)
APEMLGGPSVFIFPPPK PKDTLLIART PEVTCVVVDL DPEDPEVQIS

WFVDGKQMQT AKTQPREEQF NGTYRVVSVL PIGHQDWLKG

KQFTCKVNNK ALPSPIERTI SKARGQAHQP SVYVLPPSRE

ELSKNTVSLT CLIKDFFPPD IDVEWQSNGQ QEPESKYRTT

PPQLDEDGSY FLYSKLSVDK SRWQRGDTFI CAVMHEALHN

HYTQESLSHS PGK
```

The amino acid sequence of the Fc domain of canine IgGC is provided below:

```
                                        (SEQ ID NO: 11)
GCGLLGGPSVFIFPPP KPKDILVTAR TPTVTCVVVD LDPENPEVQI

SWFVDSKQVQ TANTQPREEQ SNGTYRVVSV LPIGHQDWLS

GKQFKCKVNN KALPSPIEEI ISKTPGQAHQ PNVYVLPPSR

DEMSKNTVTL TCLVKDFFPP EIDVEWQSNG QQEPESKYRM

TPPQLDEDGS YFLYSKLSVD KSRWQRGDTF ICAVMHEALH

NHYTQISLSH SPGK
```

The amino acid sequence of the Fc domain of canine IgGD is provided below:

```
                                        (SEQ ID NO: 12)
VPESLGGPSV FIFPPKPKDI LRITRTPEIT CVVLDLGRED

PEVQISWFVD GKEVHTAKTQ PREQQFNSTY RVVSVLPIEH

QDWLTGKEFK CRVNHIGLPS PIERTISKAR GQAHQPSVYV

LPPSPKELSS SDTVTLTCLI KDFFPPEIDV EWQSNGQPEP

ESKYHTTAPQ LDEDGSYFLY SKLSVDKSRW QQGDTFTCAV

MHEALQNHYT DLSLSHSPGK
```

Substitutions in Canine IgG Fc that Improve Half-Life

Increased serum persistence is a beneficial property for therapeutic polypeptides. This disclosure features substitutions in wild type canine IgGA, IgGB, IgGC, and IgGD Fc regions that enhance the half-life of a polypeptide or polypeptides comprising these Fc regions in a dog relative to a control polypeptide or control polypeptides, wherein the control polypeptide or control polypeptides are identical to the polypeptide or polypeptides except for having the corresponding wild type canine IgG Fc region in place of the IgG Fc region variant. The substitutions to increase half-life may be made in one or more of a canine CH2 region, a canine CH3 region, or in the context of a canine Fc (e.g., a CH2+CH3) region.

The present disclosure provides a polypeptide comprising an Fc domain of a canine IgG, or a canine FcRn-binding region thereof, wherein the polypeptide comprises at least one amino acid substitution at a position selected from the group consisting of:
(i) a position that corresponds to amino acid position 286 of a wild type canine IgG;
(ii) a position that corresponds to amino acid position 312 of a wild type canine IgG;
(iii) a position that corresponds to amino acid position 426 of a wild type canine IgG; and
(iv) a position that corresponds to amino acid position 436 of a wild type canine IgG; wherein the amino acid substitution at the position that corresponds to amino acid position 286 of the wild type canine IgG is selected from the group consisting of Tyr, Phe, Leu and Trp, wherein the amino acid positions are based on EU numbering, and wherein the polypeptide has increased binding affinity to canine FcRn when compared to an Fc domain of the wild type canine IgG. In some embodiments, the polypeptide has increased binding affinity to canine FcRn at a pH of about 5.0 to about 6.5 (e.g., about 5.5 or about 6.0) when compared to an Fc domain of the wild type canine IgG in a binding assay. In some embodiments, a binding assay refers to an assay comparing, for example, the binding affinity of a polypeptide variant described herein to canine FcRn at a pH of about 5.0 to about 6.5 as compared to the binding affinity of the wild type canine IgG to canine FcRn at the same pH (e.g., a pH of about 5.0 to about 6.5). In some embodiments, the binding assay is performed using comparable conditions. In some embodiments, the binding assay is a Surface Plasmon Resonance (SPR) assay.

In some embodiments, the at least one amino acid substitution comprises an amino acid substitution at the position that corresponds to amino acid position 312 of a wild type canine IgG.

In some embodiments, the polypeptide comprises Pro at the amino acid position that corresponds to amino acid position 312 of the wild type canine IgG.

In some embodiments, the at least one amino acid substitution comprises an amino acid substitution at the position that corresponds to amino acid position 426 of a wild type canine IgG. In some embodiments, the polypeptide comprises Tyr, His or Phe at the amino acid position that corresponds to amino acid position 426 of the wild type canine IgG. In some embodiments, the polypeptide comprises Tyr at the amino acid position that corresponds to amino acid position 426 of the wild type canine IgG. In some embodiments, the polypeptide comprises His at the amino acid position that corresponds to amino acid position 426 of the wild type canine IgG. In some embodiments, the polypeptide comprises Phe at the amino acid position that corresponds to amino acid position 426 of the wild type canine IgG.

In some embodiments, the at least one amino acid substitution comprises an amino acid substitution at the position that corresponds to amino acid position 436 of a wild type canine IgG. In some embodiments, the polypeptide comprises His at the amino acid position that corresponds to amino acid position 436 of the wild type canine IgG.

In some embodiments, the polypeptide comprises an amino acid sequence that is at least 80% identical to an amino acid sequence selected from the group consisting of SEQ ID NOs: 9 to 12.

In some instances, this disclosure provides a canine IgG CH2 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 4. Also provided are canine IgG CH2 region variants comprising an amino acid sequence that varies from any one of SEQ ID NOs.:1 to 4 by 1 to 15 (e.g., 1, 2, 3, 4, 5, 6, 7, 8, 9, 10, 11, 12, 13, 14, or 15) amino acids.

In other instances, this disclosure features a canine IgG CH3 region variant comprising an amino acid sequence that is at least 75%, at least 80%, at least 85%, at least 90%, at least 95%, at least 96%, at least 97% or at least 98% or at least 99%, identical to the amino acid sequence set forth in any one of SEQ ID NOs.:5 to 8. Also featured are canine IgG CH3 region variants comprising an amino acid sequence that varies from any one of SEQ ID NOs.:5 to 8 by 1 to 15 (e.g., 1, 2, 3, 4, 5, 6, 7, 8, 9, 10, 11, 12, 13, 14, or 15) amino acids.

In certain instances, this disclosure features a canine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:9 to 12. Also disclosed are canine IgG Fc region variants comprising an amino acid sequence that varies from any one of SEQ ID NOs.:9 to 12 by 1 to 20 (e.g., 1, 2, 3, 4, 5, 6, 7, 8, 9, 10, 11, 12, 13, 14, 15, 16, 17, 18, 19, or 20) amino acids.

In some instances, at least one (e.g. 1, 2, or 3) of the following regions in the canine IgG Fc CH2 region variant are identical to the corresponding regions in a wild type canine IgG Fc CH2 region:
amino acid positions 250-256;
amino acid positions 285-288; and
amino acid positions 307-315,
wherein the amino acid positions are based on EU numbering. In some instances, all of the above regions in the canine IgG Fc CH2 region variant are identical to the corresponding regions in a wild type canine IgG Fc CH2 region.

In some instances, at least one (e.g. 1 or 2) of the following regions in the canine IgG Fc CH3 region variant are identical to the corresponding regions in a wild type canine IgG Fc CH3 region:
amino acid positions 376-380; and
amino acid positions 428-436,
wherein the amino acid positions are based on EU numbering. In some instances, all of the above regions in the canine IgG Fc CH3 region variant are identical to the corresponding regions in a wild type canine IgG Fc CH3 region.

In some instances, at least one (e.g., 1, 2, 3, 4, or 5) of the following regions in the canine IgG Fc variant are identical to the corresponding regions in a wild type canine IgG Fc:
amino acid positions 250-256;
amino acid positions 285-288;
amino acid positions 307-315;
amino acid positions 376-380; and
amino acid positions 428-436,
wherein the amino acid positions are based on EU numbering. In some instances, all of the following regions in the canine IgG Fc variant are identical to the corresponding regions in a wild type canine IgG Fc.

In some instances, at least one (e.g., 1, 2, 3, 4, or 5) of the following regions in the canine IgG Fc variant are identical to the corresponding regions in a wild type canine IgG Fc:
amino acid positions 250-256;
amino acid positions 285, 287 and 288;
amino acid positions 307-315;
amino acid positions 376-380; and
amino acid positions 428-436,
wherein the amino acid positions are based on EU numbering. In some instances, all of the following regions in the canine IgG Fc variant are identical to the corresponding regions in a wild type canine IgG Fc.

In some embodiments, provided are a polypeptide or polypeptides comprising a canine IgG Fc CH2 region variant, the CH2 region variant comprising an amino acid sequence that is at least 75%, at least 80%, at least 85%, at least 90%, at least 95%, at least 96%, at least 97%, at least 98% or at least 99%, identical to the amino acid sequence set forth in any one of SEQ ID NOs.:1 to 4.

In some embodiments, featured are a polypeptide or polypeptides comprising a canine IgG Fc CH3 region variant, the CH3 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:5 to 8.

In some embodiments, featured are a polypeptide or polypeptides comprising a canine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:9 to 12.

In some embodiments, the polypeptide comprises:

(i) Pro at the amino acid position that corresponds to amino acid position 312 of the wild type canine IgG; and/or (ii) Tyr, His or Phe at the amino acid position that corresponds to amino acid position 426 of the wild type canine IgG; and/or (iii) Tyr, Phe, Leu and Trp at the amino acid position that corresponds to amino acid position 286 of the wild type canine IgG.

In some embodiments, the polypeptide comprises:

(i) Pro at the amino acid position that corresponds to amino acid position 312 of the wild type canine IgG; and/or (ii) Tyr at the amino acid position that corresponds to amino acid position 426 of the wild type canine IgG; and/or (iii) Tyr, Phe, Leu and Trp at the amino acid position that corresponds to amino acid position 286 of the wild type canine IgG.

In some embodiments, the polypeptide comprises:

(i) Pro at the amino acid position that corresponds to amino acid position 312 of the wild type canine IgG; and/or (ii) His at the amino acid position that corresponds to amino acid position 426 of the wild type canine IgG; and/or (iii) Tyr, Phe, Leu and Trp at the amino acid position that corresponds to amino acid position 286 of the wild type canine IgG.

As noted elsewhere, the polypeptide, in some embodiments, further comprises at least one additional amino acid substitution in a region corresponding to amino acid positions 250-256, amino acid positions 285-288; amino acid positions 307-315; amino acid positions 376-380; or amino acid positions 428-436 of the wild type canine IgG, wherein the amino acid positions are based on EU numbering, and wherein the polypeptide has increased binding to canine FcRn compared to an Fc domain of the wild type canine IgG.

In some embodiment, the polypeptide further comprises at least one additional amino acid substitution in a region corresponding to amino acid positions 250-256, amino acid positions 285, 287 and 288; amino acid positions 307-315; amino acid positions 376-380; or amino acid positions 428-436 of the wild type canine IgG, wherein the amino acid positions are based on EU numbering, and wherein the polypeptide has increased binding to canine FcRn compared to an Fc domain of the wild type canine IgG. The at least one additional amino acid substitution encompassed by the present disclosure includes one or more (e.g., 1, 2, 3, 4, 5, 6, 7, 8, 9, 10, 11, 12, 13, 14, 15, 16, 17, 18, 19, or 20) of those disclosed in Table 1.

TABLE 1

| Position (EU Numbering) | hIgG1 | Canine IgGA | Canine IgGB | Canine IgGC | Canine IgGD | Substitution |
|---|---|---|---|---|---|---|
| CH2 Region | | | | | | |
| 250 | T | I | T | I | I | E or Q |
| 251 | L | L | L | L | L | D or E |
| 252 | M | R | L | V | R | Y |
| 254 | S | T | A | A | T | T |
| 256 | T | T | T | T | T | D, E, or F |
| 285 | H | H | Q | Q | H | N or D |
| 286 | N | T | T | T | T | D |
| 307 | T | P | P | P | P | R, Q, or A |
| 308 | V | I | I | I | I | P |
| 309 | L | E | G | G | E | P |
| 311 | Q | Q | Q | Q | Q | V |
| 315 | N | T | K | S | T | D |
| CH3 Region | | | | | | |
| 378 | A | D | D | D | D | V |
| 380 | E | E | E | E | E | A |
| 428 | M | M | M | M | M | L |
| 430 | E | E | E | E | E | A or K |
| 433 | H | Q | H | H | Q | K |
| 434 | N | N | N | N | N | S, A, or F |
| 435 | H | H | H | H | H | Y |
| 436 | Y | Y | Y | Y | Y | H |

In some instances, the at least one additional amino acid substitution encompassed by the present disclosure includes one or more (e.g., 1, 2, 3, or 4) of those substitutions disclosed in Table 2.

TABLE 2

| Position (EU Numbering) | hIgG1 | Canine IgGA | Canine IgGB | Canine IgGC | Canine IgGD | Substitution |
|---|---|---|---|---|---|---|
| CH2 Region | | | | | | |
| 252 | M | R | L | V | R | Y or M |
| 254 | S | T | A | A | T | T |
| 256 | T | T | T | T | T | E |
| CH3 Region | | | | | | |
| 434 | N | N | N | N | N | Y, W, R, or H |

All possible combinations and permutations of the substitutions disclosed above are encompassed by this disclosure. In some instances, the polypeptide comprises at least one (e.g. two or more, three or more, four or more, five or more) additional amino acid substitutions selected from the group consisting of:

(i) Tyr at amino acid position 252, Thr at amino acid position 254, and Glu at amino acid position 256;
(ii) Leu at amino acid position 428 and Ser at amino acid position 434;
(iii) Asp at amino acid position 256, Arg at amino acid position 307, and Val at amino acid position 311;
(iv) Asp at amino acid position 256, Asp at amino acid position 315, and Val at amino acid position 378;
(v) Asp at amino acid position 256, Asp, Tyr, Phe, Leu or Trp at amino acid position 286, Arg at amino acid position 307, and Val at amino acid position 311;
(vi) Asn at amino acid position 285, Gln at amino acid position 307, and Asp at amino acid position 315;
(vii) Asp at amino acid position 256, Arg at amino acid position 307, Val at amino acid position 311, and Val at amino acid position 378;
(viii) Asp at amino acid position 285, Val at amino acid position 311, and Val at amino acid position 378;

(ix) Asp at amino acid position 256, Asp at amino acid position 285, and Val at amino acid position 378;
(x) Asp at amino acid position 256, Val at amino acid position 311, and Val at amino acid position 378;
(xi) Asp at amino acid position 256, Asp at amino acid position 285, Asp, Tyr, Phe, Leu or Trp at amino acid position 286, Arg at amino acid position 307, and Val at amino acid position 378;
(xii) Asp at amino acid position 256, Asp at amino acid position 286, Arg at amino acid position 307, Val at amino acid position 311, and Val at position 378;
(xiii) Gln at amino acid position 307, Val at amino acid position 311, and Val at amino acid position 378;
(xiv) Asp at amino acid position 285, Gln at amino acid position 307, and Val at amino acid position 378;
(xv) Asp at amino acid position 256, Asp at amino acid position 285, Arg at amino acid position 307, Val at amino acid position 311, and Val at amino acid position 378;
(xvi) Gln at amino acid position 307, Ala at amino acid position 380, Ser or Ala at amino acid position 434;
(xvii) Leu at amino acid position 428, and Ser or Ala at amino acid position 434; (xviii) Gln at amino acid position 250 and Leu at amino acid position 428;
(xix) Glu at amino acid position 250 and Glu at amino acid position 251;
(xx) Phe at amino acid position 256 and Phe at amino acid position 309;
(xxi) Ala at amino acid position 430 and Lys at amino acid position 433;
(xxii) Phe at amino acid position 434 and His at amino acid position 436; and
(xxiii) Tyr at amino acid position 435 and His at amino acid position 436;

In some instances, the substitutions do not include the combination of Tyr at amino acid position 252, Thr at amino acid position 254, and Glu at amino acid position 256.

In some embodiments, the at least one additional amino acid substitution is at a position selected from the group consisting of:
(i) an amino acid position that corresponds to amino acid position 250 of the wild type canine IgG,
(ii) an amino acid position that corresponds to amino acid position 251 of the wild type canine IgG,
(iii) an amino acid position that corresponds to amino acid position 252 of the wild type canine IgG,
(iv) an amino acid position that corresponds to amino acid position 254 of the wild type canine IgG,
(v) an amino acid position that corresponds to amino acid position 256 of the wild type canine IgG,
(vi) an amino acid position that corresponds to amino acid position 285 of the wild type canine IgG,
(vii) an amino acid position that corresponds to amino acid position 286 of the wild type canine IgG,
(viii) an amino acid position that corresponds to amino acid position 307 of the wild type canine IgG,
(ix) an amino acid position that corresponds to amino acid position 308 of the wild type canine IgG,
(x) an amino acid position that corresponds to amino acid position 309 of the wild type canine IgG,
(xi) an amino acid position that corresponds to amino acid position 311 of the wild type canine IgG,
(xii) an amino acid position that corresponds to amino acid position 315 of the wild type canine IgG,
(xiii) an amino acid position that corresponds to amino acid position 378 of the wild type canine IgG,
(xiv) an amino acid position that corresponds to amino acid position 380 of the wild type canine IgG,
(xv) an amino acid position that corresponds to amino acid position 428 of the wild type canine IgG,
(xvi) an amino acid position that corresponds to amino acid position 430 of the wild type canine IgG,
(xvii) an amino acid position that corresponds to amino acid position 433 of the wild type canine IgG,
(xviii) an amino acid position that corresponds to amino acid position 434 of the wild type canine IgG,
(xix) an amino acid position that corresponds to amino acid position 435 of the wild type canine IgG, and
(xx) an amino acid position that corresponds to amino acid position 436 of the wild type canine IgG.

In some embodiments, the polypeptide comprises:
(i) Glu or Gln at the amino acid position that corresponds to amino acid position 250 of the wild type canine IgG,
(ii) Asp or Glu at the amino acid position that corresponds to amino acid position 251 of the wild type canine IgG,
(iii) Tyr or Met at the amino acid position that corresponds to amino acid position 252 of the wild type canine IgG,
(iv) Thr or Ser at the amino acid position that corresponds to amino acid position 254 of the wild type canine IgG,
(v) Asp, Glu or Phe at the amino acid position that corresponds to amino acid position 256 of the wild type canine IgG,
(vi) Asn or Asp at the amino acid position that corresponds to amino acid position 285 of the wild type canine IgG,
(vii) Asp, Tyr, Phe, Leu or Trp at the amino acid position that corresponds to amino acid position 286 of the wild type canine IgG,
(viii) Arg, Gln or Ala at the amino acid position that corresponds to amino acid position 307 of the wild type canine IgG,
(ix) Pro at the amino acid position that corresponds to amino acid position 308 of the wild type canine IgG,
(x) Pro at the amino acid position that corresponds to amino acid position 309 of the wild type canine IgG,
(xi) Val at the amino acid position that corresponds to amino acid position 311 of the wild type canine IgG,
(xii) Asp at the amino acid position that corresponds to amino acid position 315 of the wild type canine IgG,
(xiii) Val at the amino acid position that corresponds to amino acid position 378 of the wild type canine IgG,
(xiv) Ala at the amino acid position that corresponds to amino acid position 380 of the wild type canine IgG,
(xv) Leu at the amino acid position that corresponds to amino acid position 428 of the wild type canine IgG,
(xvi) Ala or Lys at the amino acid position that corresponds to amino acid position 430 of the wild type canine IgG,
(xvii) Lys at the amino acid position that corresponds to amino acid position 433 of the wild type canine IgG,
(xviii) Trp, Tyr, Arg, His, Ser, Ala or Phe at the amino acid position that corresponds to amino acid position 434 of the wild type canine IgG,
(xix) Tyr at the amino acid position that corresponds to amino acid position 435 of the wild type canine IgG, and/or
(xx) His at the amino acid position that corresponds to amino acid position 436 of the wild type canine IgG.

In some embodiments, the at least one amino acid substitution comprises an amino acid substitution at the position that corresponds to amino acid position 286 of the wild type canine IgG. In some embodiments, the polypeptide comprises Tyr at the amino acid position that corresponds to amino acid position 286 of the wild type canine IgG. In some embodiments, the polypeptide comprises Phe at the amino acid position that corresponds to amino acid position 286 of the wild type canine IgG. In some embodiments, the polypeptide comprises Leu at the amino acid position that corresponds to amino acid position 286 of the wild type canine IgG. In some embodiments, the polypeptide comprises Trp at the amino acid position that corresponds to amino acid position 286 of the wild type canine IgG. In some embodiments, the polypeptide comprises at least one additional amino acid substitution at a position selected from the group consisting of:
(i) an amino acid position that corresponds to amino acid position 250 of the wild type canine IgG,
(ii) an amino acid position that corresponds to amino acid position 251 of the wild type canine IgG,
(iii) an amino acid position that corresponds to amino acid position 252 of the wild type canine IgG,
(iv) an amino acid position that corresponds to amino acid position 254 of the wild type canine IgG,
(v) an amino acid position that corresponds to amino acid position 256 of the wild type canine IgG,
(vi) an amino acid position that corresponds to amino acid position 285 of the wild type canine IgG,
(vii) an amino acid position that corresponds to amino acid position 307 of the wild type canine IgG,
(viii) an amino acid position that corresponds to amino acid position 308 of the wild type canine IgG,
(ix) an amino acid position that corresponds to amino acid position 309 of the wild type canine IgG,
(x) an amino acid position that corresponds to amino acid position 311 of the wild type canine IgG,
(xi) an amino acid position that corresponds to amino acid position 315 of the wild type canine IgG,
(xii) an amino acid position that corresponds to amino acid position 378 of the wild type canine IgG,
(xiii) an amino acid position that corresponds to amino acid position 380 of the wild type canine IgG,
(xiv) an amino acid position that corresponds to amino acid position 428 of the wild type canine IgG,
(xv) an amino acid position that corresponds to amino acid position 430 of the wild type canine IgG,
(xvi) an amino acid position that corresponds to amino acid position 433 of the wild type canine IgG,
(xvii) an amino acid position that corresponds to amino acid position 434 of the wild type canine IgG,
(xviii) an amino acid position that corresponds to amino acid position 435 of the wild type canine IgG, and
(xix) an amino acid position that corresponds to amino acid position 436 of the wild type canine IgG.
In some embodiments, the polypeptide comprises:
(i) Glu or Gln at the amino acid position that corresponds to amino acid position 250 of the wild type canine IgG,
(ii) Asp or Glu at the amino acid position that corresponds to amino acid position 251 of the wild type canine IgG,
(iii) Tyr or Met at the amino acid position that corresponds to amino acid position 252 of the wild type canine IgG,
(iv) Thr or Ser at the amino acid position that corresponds to amino acid position 254 of the wild type canine IgG,
(v) Asp, Glu or Phe at the amino acid position that corresponds to amino acid position 256 of the wild type canine IgG,
(vi) Asn or Asp at the amino acid position that corresponds to amino acid position 285 of the wild type canine IgG,
(vii) Arg, Gln or Ala at the amino acid position that corresponds to amino acid position 307 of the wild type canine IgG,
(viii) Pro at the amino acid position that corresponds to amino acid position 308 of the wild type canine IgG,
(ix) Pro at the amino acid position that corresponds to amino acid position 309 of the wild type canine IgG,
(x) Val at the amino acid position that corresponds to amino acid position 311 of the wild type canine IgG,
(xi) Asp at the amino acid position that corresponds to amino acid position 315 of the wild type canine IgG,
(xii) Val at the amino acid position that corresponds to amino acid position 378 of the wild type canine IgG,
(xiii) Ala at the amino acid position that corresponds to amino acid position 380 of the wild type canine IgG,
(xiv) Leu at the amino acid position that corresponds to amino acid position 428 of the wild type canine IgG,
(xv) Ala or Lys at the amino acid position that corresponds to amino acid position 430 of the wild type canine IgG,
(xvi) Lys at the amino acid position that corresponds to amino acid position 433 of the wild type canine IgG,
(xvii) Trp, Tyr, Arg, His, Ser, Ala or Phe at the amino acid position that corresponds to amino acid position 434 of the wild type canine IgG,
(xviii) Tyr at the amino acid position that corresponds to amino acid position 435 of the wild type canine IgG, and/or
(xix) His at the amino acid position that corresponds to amino acid position 436 of the wild type canine IgG.
In some embodiments, the at least one additional amino acid substitution is at a position selected from the group consisting of:
(i) an amino acid position that corresponds to amino acid position 250 of the wild type canine IgG,
(ii) an amino acid position that corresponds to amino acid position 252 of the wild type canine IgG,
(iii) an amino acid position that corresponds to amino acid position 254 of the wild type canine IgG,
(iv) an amino acid position that corresponds to amino acid position 256 of the wild type canine IgG,
(v) an amino acid position that corresponds to amino acid position 285 of the wild type canine IgG,
(vi) an amino acid position that corresponds to amino acid position 307 of the wild type canine IgG,
(vii) an amino acid position that corresponds to amino acid position 309 of the wild type canine IgG,
(viii) an amino acid position that corresponds to amino acid position 311 of the wild type canine IgG,
(ix) an amino acid position that corresponds to amino acid position 315 of the wild type canine IgG,
(x) an amino acid position that corresponds to amino acid position 433 of the wild type canine IgG,
(xi) an amino acid position that corresponds to amino acid position 434 of the wild type canine IgG, and
(xii) an amino acid position that corresponds to amino acid position 436 of the wild type canine IgG.
In some embodiments, the polypeptide comprises:
(i) Glu or Gln at the amino acid position that corresponds to amino acid position 250 of the wild type canine IgG,
(ii) Tyr or Met at the amino acid position that corresponds to amino acid position 252 of the wild type canine IgG,
(iii) Thr or Ser at the amino acid position that corresponds to amino acid position 254 of the wild type canine IgG,
(iv) Asp, Glu or Phe at the amino acid position that corresponds to amino acid position 256 of the wild type canine IgG,
(v) Asn or Asp at the amino acid position that corresponds to amino acid position 285 of the wild type canine IgG,
(vi) Arg, Gln or Ala at the amino acid position that corresponds to amino acid position 307 of the wild type canine IgG,
(vii) Pro at the amino acid position that corresponds to amino acid position 309 of the wild type canine IgG,
(viii) Val at the amino acid position that corresponds to amino acid position 311 of the wild type canine IgG, (ix) Asp at the amino acid position that corresponds to amino acid position 315 of the wild type canine IgG,
(x) Lys at the amino acid position that corresponds to amino acid position 433 of the wild type canine IgG,
(xi) Trp, Tyr, Arg, His, Ser, Ala or Phe at the amino acid position that corresponds to amino acid position 434 of the wild type canine IgG, and
(xii) His at the amino acid position that corresponds to amino acid position 436 of the wild type canine IgG.

In some embodiments, the at least one additional amino acid substitution is at a position selected from the group consisting of:
(i) an amino acid position that corresponds to amino acid position 252 of the wild type canine IgG,
(ii) an amino acid position that corresponds to amino acid position 254 of the wild type canine IgG,
(iii) an amino acid position that corresponds to amino acid position 256 of the wild type canine IgG, and
(iv) an amino acid position that corresponds to amino acid position 434 of the wild type canine IgG.

In some embodiments, the polypeptide comprises:
(i) Tyr or Met at the amino acid position that corresponds to amino acid position 252 of the wild type canine IgG,
(ii) Thr or Ser at the amino acid position that corresponds to amino acid position 254 of the wild type canine IgG,
(iii) Asp, Glu or Phe at the amino acid position that corresponds to amino acid position 256 of the wild type canine IgG, and/or
(iv) Trp, Tyr, Arg, His, Ser, Ala or Phe at the amino acid position that corresponds to amino acid position 434 of the wild type canine IgG.

In some embodiments, the polypeptide comprises:
(i) Tyr at the amino acid position that corresponds to amino acid position 252 of the wild type canine IgG,
(ii) Thr at the amino acid position that corresponds to amino acid position 254 of the wild type canine IgG,
(iii) Glu at the amino acid position that corresponds to amino acid position 256 of the wild type canine IgG, and/or
(iv) Trp, Tyr, Arg or His at the amino acid position that corresponds to amino acid position 434 of the wild type canine IgG.

The substitutions may be made on one or both chains of a CH2 domain, a CH3 domain, or an Fc domain. In some instances, the substitutions on both chains of a CH2 domain, a CH3 domain, or an Fc domain are identical. In some instances, the substitutions on both chains of a CH2 domain, a CH3 domain, or an Fc domain are not identical. In some instances, the Fc region includes one or more additional substitutions that increase or decrease effector function and/or improve product heterogeneity.

The present disclosure also provides a polypeptide comprising a canine IgG Fc region variant, or a canine FcRn-binding region thereof, wherein the polypeptide comprises amino acid substitutions at two or more (e.g., two, three, four, or five) positions selected from the group consisting of:
(i) a position that corresponds to amino acid position 286 of a wild type canine IgG;
(ii) a position that corresponds to amino acid position 312 of a wild type canine IgG;
(iii) a position that corresponds to amino acid position 426 of a wild type canine IgG;
(iv) a position that corresponds to amino acid position 434 of a wild type canine IgG; and
(v) a position that corresponds to amino acid position 436 of a wild type canine IgG,
wherein the amino acid positions are based on EU numbering, and wherein the polypeptide has increased binding affinity to canine FcRn when compared to an Fc domain of the wild type canine IgG.

All possible combinations and permutations of the substitutions disclosed herein are encompassed by this disclosure In some embodiments, the two or more amino acid substitutions provide a synergistic effect, insofar as the polypeptide has increased binding affinity to canine FcRn when compared to a polypeptide comprising only one of the foregoing two or more amino acid substitutions.

In some embodiments, the polypeptides described herein comprise at least one additional amino acid substitution at a position other than those that correspond to positions 286, 312, 426, 434, and 436 of a wild type canine IgG. For example, the polypeptides described herein can include about 1, 2, 3, 4, or 5, to about 30 or less additional amino acid substitutions of a canine IgG.

In some embodiments, the polypeptide has increased binding affinity to canine FcRn at a pH of about 5.0 to about 6.5 (e.g., about 5.5 or about 6.0) when compared to an Fc domain of the wild type canine IgG. Methods of determining FcRn binding affinity will be familiar to persons skilled in the art, illustrative examples of which are described elsewhere herein.

The difference in FcRn binding activity may suitably be determined using a comparable or similar assay for each variable (e.g., pH value, number of amino acid substitutions, position of amino acid substitutions, type of amino acid substitution, etc.). Comparable assays in this context refer to assays that operate substantially in the same or similar manner so as to minimise or otherwise avoid unnecessary variables that may have a substantial impact on the way in which the assay performs and the outcome that is independent of the variable being assessed. It will be understood, however, that conditions necessary to perform an assay for determining FcRn binding at, for example, pH 6.0, may differ from conditions necessary to perform a similar assay at pH 7.4, having regard to, for example, the effect of pH on the way in which the assay performs. In some embodiments, the polypeptide has increased binding affinity to canine FcRn at a pH of about 5.0 to about 6.5 (e.g., about 5.5 or about 6.0) when compared to an Fc domain of the wild type canine IgG using a comparable assay.

In some embodiments, the polypeptide binds to a canine FcRn at a higher level at an acidic pH than at a neutral pH in a comparable assay. In some embodiments, the polypeptide binds to a canine FcRn at a higher level at pH 5.5 than at pH 7.4 in a comparable assay. In some embodiments, the polypeptide binds to a canine FcRn at a higher level at pH 6.0 than at pH 7.4 in a comparable assay.

In some embodiments, the amino acid substitution at the position that corresponds to amino acid position 286 of a wild type canine IgG is selected from the group consisting of T286L, T286Y and conservative amino acid substitutions of any of foregoing.

In some embodiments, the polypeptide of claim 1, wherein the amino acid substitution at the position that corresponds to amino acid position 312 of a wild type canine IgG is D312P or a conservative amino acid substitution thereof.

In some embodiments, the amino acid substitution at the position that corresponds to amino acid position 426 of a wild type canine IgG is selected from the group consisting of A426Y, A426H and conservative amino acid substitutions of any of foregoing.

In some embodiments, the amino acid substitution at the position that corresponds to amino acid position 434 of a wild type canine IgG is N434R or a conservative amino acid substitution thereof.

In some embodiments, the amino acid substitution at the position that corresponds to amino acid position 436 of a wild type canine IgG is Y436H or a conservative amino acid substitution thereof.

In some embodiments, the polypeptide comprises an amino acid substitution at the position that corresponds to amino acid position 426 of a wild type canine IgG.

The term "conservative amino acid substitution" as used herein refers to a substitution of one amino acid residue for another amino acid residue that has similar properties such as charge, hydrophobicity and size. In some embodiments, a conservative amino acid substitution refers to a substitution that results in similar properties or functions as another amino acid substitution. For example, a conservative amino acid substitution of A426Y can be A426F or A426T.

In some embodiments, the polypeptide comprises amino acid substitutions at the two or more positions selected from the group consisting of:
(i) positions that correspond to amino acid positions 426 and 286 of a wild type canine IgG;
(ii) positions that correspond to amino acid position 426 and 312 of a wild type canine IgG;
(iii) positions that correspond to amino acid position 426 and 434 of a wild type canine IgG; and
(iv) positions that correspond to amino acid position 426 and 436 of a wild type canine IgG.

In some embodiments, the two or more amino acid substitutions are selected from the group consisting of:
(i) A426Y in combination with one or more of T286L, T286Y, D312P, N434R and Y436H;
(ii) A426H in combination with one or more of T286L, T286Y, D312P, N434R and Y436H; and
(iii) N434R in combination with one or more of T286L, T286Y, D312P and Y436H.

In some embodiments, the polypeptide comprises amino acid substitutions selected from the group consisting of:
(i) A426Y and T286L;
(ii) A426Y and D312P;
(iii) A426Y and Y436H;
(iv) A426H and T286L;
(v) A426H and T286Y; and
(vi) A426H and D312P.

In some embodiments, the polypeptide comprises an amino acid sequence that is at least 80% identical to an amino acid sequence selected from the group consisting of SEQ ID NOs: 9 to 12.

In some instances, this disclosure provides a canine IgG CH2 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 4. Also provided are canine IgG CH2 region variants comprising an amino acid sequence that varies from any one of SEQ ID NOs.:1 to 4 by 1 to 15 (e.g., 1, 2, 3, 4, 5, 6, 7, 8, 9, 10, 11, 12, 13, 14, or 15) amino acids.

In other instances, this disclosure features a canine IgG CH3 region variant comprising an amino acid sequence that is at least 75%, at least 80%, at least 85%, at least 90%, at least 95%, at least 96%, at least 97% or at least 98% or at least 99%, identical to the amino acid sequence set forth in any one of SEQ ID NOs.:5 to 8. Also featured are canine IgG CH3 region variants comprising an amino acid sequence that varies from any one of SEQ ID NOs.:5 to 8 by 1 to 15 (e.g., 1, 2, 3, 4, 5, 6, 7, 8, 9, 10, 11, 12, 13, 14, or 15) amino acids.

In certain instances, this disclosure features a canine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:9 to 12. Also disclosed are canine IgG Fc region variants comprising an amino acid sequence that varies from any one of SEQ ID NOs.:9 to 12 by 1 to 20 (e.g., 1, 2, 3, 4, 5, 6, 7, 8, 9, 10, 11, 12, 13, 14, 15, 16, 17, 18, 19, or 20) amino acids.

In some instances, at least one (e.g. 1, 2, or 3) of the following regions in the canine IgG Fc CH2 region variant are identical to the corresponding regions in a wild type canine IgG Fc CH2 region:
amino acid positions 250-256; and
amino acid positions 307-311,
wherein the amino acid positions are based on EU numbering. In some instances, all of the above regions in the canine IgG Fc CH2 region variant are identical to the corresponding regions in a wild type canine IgG Fc CH2 region.

In some instances, at least one (e.g. 1 or 2) of the following regions in the canine IgG Fc CH3 region variant are identical to the corresponding regions in a wild type canine IgG Fc CH3 region:
amino acid positions 376-380; and
amino acid positions 428-433,
wherein the amino acid positions are based on EU numbering. In some instances, all of the above regions in the canine IgG Fc CH3 region variant are identical to the corresponding regions in a wild type canine IgG Fc CH3 region.

In some instances, at least one (e.g., 1, 2, 3, 4, or 5) of the following regions in the canine IgG Fc variant are identical to the corresponding regions in a wild type canine IgG Fc:
amino acid positions 250-256;
amino acid positions 307-311;
amino acid positions 376-380; and
amino acid positions 428-433,
wherein the amino acid positions are based on EU numbering. In some instances, all of the following regions in the canine IgG Fc variant are identical to the corresponding regions in a wild type canine IgG Fc.

In some instances, at least one (e.g., 1, 2, 3, 4, or 5) of the following regions in the canine IgG Fc variant are identical to the corresponding regions in a wild type canine IgG Fc:
amino acid positions 250-256;
amino acid positions 285, 287 and 288;
amino acid positions 307-311;
amino acid positions 376-380; and
amino acid positions 428-433,
wherein the amino acid positions are based on EU numbering. In some instances, all of the following regions in the canine IgG Fc variant are identical to the corresponding regions in a wild type canine IgG Fc.

In some embodiments, provided are a polypeptide or polypeptides comprising a canine IgG Fc CH2 region variant, the CH2 region variant comprising an amino acid sequence that is at least 75%, at least 80%, at least 85%, at least 90%, at least 95%, at least 96%, at least 97%, at least 98% or at least 99%, identical to the amino acid sequence set forth in any one of SEQ ID NOs.:1 to 4.

In some embodiments, featured are a polypeptide or polypeptides comprising a canine IgG Fc CH3 region variant, the CH3 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:5 to 8.

In some embodiments, featured are a polypeptide or polypeptides comprising a canine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:9 to 12.

Other Substitutions that can be Combined with the Half-Life Enhancing Substitutions The development of a therapeutic polypeptide/protein (e.g., a monoclonal antibody) is a complex process that entails coordination of a complex set of activities to generate the desired polypeptide/protein. These include optimization of the specificity, affinity, functional activity, expression level in engineered cell lines, long-term stability, elimination or enhancement of effector functions and development of commercially viable manufacturing and purification methods. This disclosure encompasses substitutions at one or more additional amino acid positions of the Fc region variant that facilitates any one or more of the above goals.

In some embodiments, the Fc region variant comprises amino acid substitutions at one or more additional amino acid positions that increase or decrease effector function and/or improve product heterogeneity.

In some embodiments, the substitutions are introduced to reduce effector function of the canine Fc region. Such substitutions may be at one or more (e.g., 1, 2, 3, 4, 5, 6, or 7) of the following positions of the canine IgG (numbering according to EU numbering): 238, 265, 297, 298, 299, 327, and 329. The substitution(s) can be to any of the other 19 amino acids. In some instances, the substitution is conservative. In certain non-limiting instances, the substituted amino acid at position 238 is Ala; the substituted amino acid at position 265 is Ala; the substituted amino acid at position 297 is Ala or Gln; the substituted amino acid at position 298 is Pro; the substituted amino acid at position 299 is Ala; the substituted amino acid at position 327 is Gly; and the substituted amino acid at position 329 is Ala. In some instances, the variant Fc region is from a canine IgGB or IgGC antibody.

In some embodiments, substitutions are introduced to a wild type canine IgG Fc region to enhance binding to Protein A so as to facilitate purification by protein A chromatography. Such substitutions may be at one or both (e.g., 1, 2, 3, 4, 5, 6, or 7) of the following positions of the canine IgG (numbering according to EU numbering): 252 and 254. The substitution(s) can be to any of the other 19 amino acids. In some instances, the substitution is conservative. In certain non-limiting instances, the substituted amino acid at position 252 is Met; and the substituted amino acid at position 254 is Ser.

In some embodiments, the substitutions are made to alter binding affinity to FcRn as compared to a parent polypeptide or a wildtype polypeptide (e.g., to increase or reduce binding affinity with FcRn). In some variations, the modification can be one, two, three, or four modifications that are selected from the group consisting of: 308F, 428L, 434M and 434S, where the numbering is according to the EU numbering. In some embodiments, the Fc variant includes one or more modifications selected from the group consisting of: 252Y/428L, 428L/434H, 428L/434F, 428L/434Y, 428L/434A, 428L/434M, and 428L/434S, where the numbering is according to the EU numbering. In some embodiments, the Fc variant includes one or more modification selected from the group consisting of: 428L/434S, 308F/428L/434S, where the numbering is according to the EU numbering. In some embodiments, the Fc variant includes one or more modifications selected from the group consisting of: 259I/434S, 308F/434S, 308F/428L/434S, 259I/308F/434S, 307Q/308F/434S, 250I/308F/434S, and 308F/319L/434S, where the numbering is according to the EU numbering. A detailed description of these modifications is described in e.g., U.S. Pat. No. 8,883,973B2, which is incorporated herein by reference in its entirety.

In some embodiments, the polypeptide comprises a hinge region of a canine antibody. In some embodiments, modifications can be made to the hinge region of the canine antibody to increase half-life. In some embodiments, the modification is 228P according to EU numbering.

In some embodiments, the binding with FcRn is pH-dependent. H310 and H435 (EU numbering) can be critical for pH-dependent binding. Thus, in some embodiments, the amino acids at position 310 (EU numbering) is histidine. In some embodiments, the amino acids at position 435 (EU numbering) is histidine. In some embodiments, the amino acids at both positions are histidine.

In some embodiments, the Fc region has LALA mutations (L234A and L235A mutations in EU numbering), or LALA-PG mutations (L234A, L235A, P329G mutations in EU numbering). In some embodiments, the LALA mutation is P234A, M234A, or S234A. In some embodiments, the amino acid residue at position 234 (EU numbering) is Ala. In some embodiments, the amino acid residue at position 234 (EU numbering) is Ala. In some embodiments, the amino acid residues at positions 234 and 235 (EU numbering) are Ala.

Polypeptides Comprising the Canine IgG Fc Variants

The disclosure encompasses any polypeptide that may benefit from having an increased half-life in a dog. To increase half-life these polypeptides are designed to include an Fc region variant (e.g., a CH2 region, a CH3 region, a CH2+CH3 region) disclosed above.

Exemplary polypeptides include, but are not limited to, whole antibodies, scFvs, nanobodies, ligand-binding portions of a receptor, cytokines, growth factors, enzymes, and peptides. For example, a CH3 domain variant disclosed above may be attached to an scFv nanobody, ligand-binding portion of a receptor (e.g., the ligand-binding portion of canine IL-13Rα1 or IL-13Rα2), a cytokine, a growth factor, an enzyme, or a peptide. As used herein, the terms "nanobody", "VHH", "VHH antibody fragment" and "single domain antibody" are used interchangeably herein to denote the variable domain of the single heavy chain of antibodies of the type of those found in *Camelidae*, which are typically found in natural to lack light chains. Suitable nanobodies will be familiar to persons skilled in the art, illustrated examples of which include nanobodies of camels, dromedaries, llamas and alpacas. Alternatively, an Fc region variant disclosed above may be attached to these polypeptides. In another embodiment, a canine or caninized antibody is modified to include an Fc region variant disclosed herein.

In some embodiments, the polypeptides of this disclosure include an antibody hinge region. The hinge region may be placed between the antigen or ligand-binding domain of the polypeptide and the Fc region variant. In some instances, the hinge region is attached to the C-terminus of a cytokine, a growth factor, an enzyme, or a peptide and the hinge region is attached to the N-terminus of the Fc region variant. Exemplary hinge region sequences are provided below.

IgGA:
(SEQ ID NO: 17)
FNECRCTDTPPCPVPEP;

IgGB:
(SEQ ID NO: 18)
PKRENGRVPRPPDCPKCPAPEM;

IgGC:
(SEQ ID NO: 19)
AKECECKCNCNNCPCPGCGL;

IgGD:
(SEQ ID NO: 20)
PKESTCKCISPCPVPES;
and

IgGDmut:
(SEQ ID NO: 21)
PKESTCKCIPPCPVPES.

The hinge region, if used, in a recombinant protein of this disclosure may include zero to six (i.e., 0, 1, 2, 3, 4, 5, or 6) amino acid substitutions relative to an amino acid sequence set forth in any one of SEQ ID NOs.:17-21. In some instances, the hinge region used in a recombinant protein of this disclosure is at least 80%, at least 85%, at least 90%, at least 95%, at least 96%, at least 97%, at least 98%, at least 99%, or 100% identical to an amino acid sequence set forth in any one of SEQ ID NOs.:17-21.

In some embodiments, a linker sequence may be used instead of an antibody hinge sequence to connect the polypeptide (e.g., antibodies, ligand-binding domains of receptors, enzymes, ligands, peptides) to the canine Fc region variants disclosed herein. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Examples of peptide linkers include: Gly, Ser; Gly Ser; Gly Gly Ser; Ser Gly Gly; Gly Gly Gly Ser (SEQ ID NO:22); Ser Gly Gly Gly Gly (SEQ ID NO:23); Gly Gly Gly Gly Ser (SEQ ID NO:24); Ser Gly Gly Gly Gly (SEQ ID NO:25); Gly Gly Gly Gly Gly Ser (SEQ ID NO:26); Ser Gly Gly Gly Gly Gly (SEQ ID NO:27); Gly Gly Gly Gly Gly Gly Ser (SEQ ID NO:28); Ser Gly Gly Gly Gly Gly Gly (SEQ ID NO:29); (Gly Gly Gly Gly Ser)$_n$ (SEQ ID NO:24)n, wherein n is an integer of one or more (e.g., 1, 2, 3, 4, 5); and (Ser Gly Gly Gly Gly)$_n$ (SEQ ID NO:25)n, wherein n is an integer of one or more (e.g., 1, 2, 3, 4, 5).

Non-peptide linkers may also be used to link the polypeptide or polypeptides of interest to an Fc region variant disclosed herein. For example, alkyl linkers such as —NH (CH$_2$)$_n$C(O)—, wherein n=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc.

The polypeptide or polypeptides of this disclosure may comprise a binding domain. The binding domain can specifically bind to a protein, subunit, domain, motif, and/or epitope of a selected target described herein. In some embodiments, the polypeptide or polypeptides (e.g., fusion polypeptide) can comprise a protein, wherein the protein is a therapeutic protein described herein. In some embodiments, the target (e.g., for the target of the binding domain) or the therapeutic protein (e.g., for the fusion polypeptide) is selected from the group consisting of: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RITA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, IgE, Angiotensin type 1 (AT1) receptor, Angiotensin type 2 (AT2) receptor, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD47, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, GLP1, GLP2, Glucagon, Glut 4, glycoprotein IIb/IIIa (GP IIb/IIIa), GM-CSF, gp130, gp72, GRO, GnRH, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, cardiac myosin, cytomegalovirus (CMV), growth hormone (GH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bpl, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NAV 1.7, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PD1, PDL1, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p'75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DCTRAIL R2 TNFRH2), TNFRST23 (DCTRAIL R1TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk (e.g., TrkA), TROP-2, TSG, TSLP, tumor-associated antigen CA 125, tumor-associated antigen expressing Lewis Y related carbohydrate, TWEAK, TXB2, Ung, UPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factor.

In some embodiments, the binding domain specifically binds to one or more therapeutic targets or antigens in canine, such as, but are not limited to, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bpl, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (flt-1), VEGF, VEGFR, and VEGFR-3 (flt-4).

In some embodiments, the polypeptide or polypeptides can comprise a protein, wherein the protein is a therapeutic protein, e.g., EPO, CTLA4, LFA3, VEGFR1/VEGFR3, IL-1R, IL-4R, GLP-1 receptor agonist, or Thrombopoietin binding peptide. In some embodiments, the therapeutic protein is ACE, ACE-2, Activin, Activin A, Activin AB, Activin B, Activin C, Activin RIA, Activin MA ALK-2, Activin RIB ALK-4, Activin RITA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bpl, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta Ruth, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (flt-1), VEGF, VEGFR, or VEGFR-3 (flt-4).

In some embodiments, the therapeutic protein is any protein described herein. In some embodiments, the polypeptide or polypeptides further comprises a canine IgG CH2 domain, IgG CH3 domain, or IgG Fc region as described herein. The modified canine IgG CH2 domain, IgG CH3 domain, or IgG Fc region can enhance the half-life the therapeutic proteins in vivo.

Pharmaceutical Compositions

To prepare pharmaceutical or sterile compositions of a polypeptide or polypeptides described herein, the polypeptide or polypeptides can be admixed with a pharmaceutically acceptable carrier or excipient. (See, e.g., Remington's Pharmaceutical Sciences and U.S. Pharmacopeia: National Formulary, Mack Publishing Company, Easton, Pa. (1984)).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.). In one embodiment, the polypeptide or polypeptides of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the polypeptide compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, a polypeptide or polypeptides exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the polypeptide or polypeptides can be administered by an invasive route such as by injection. In further embodiments, the polypeptide or polypeptides is administered intravenously, subcutaneously, intramuscularly, intraarterially, intratumorally, or by inhalation, aerosol delivery.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the polypeptide or polypeptides in a local rather than systemic manner, for example, via injection of the antibody directly into an arthritic joint or pathogen-induced lesion characterized by immunopathology, often in a depot or sustained release formulation. Furthermore, one may administer the polypeptide or polypeptides in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including, without limitation, the age, weight, and physical condition of the canine being treated, the serum or tissue turnover rate of the therapeutic antibody, the level of symptoms, the immunogenicity of the therapeutic polypeptide or polypeptides, and the accessibility of the target cells in the biological matrix. Preferably, the administration regimen delivers sufficient therapeutic polypeptide or polypeptides to effect improvement in the target disease state, while simultaneously minimizing undesired side effects. Accordingly, the amount of biologic delivered depends in part on the particular therapeutic polypeptide or polypeptides and the severity of the condition being treated. Guidance in selecting appropriate doses of therapeutic antibodies is available (see, e.g., Wawrzynczak Antibody Therapy, Bios Scientific Pub. Ltd, Oxfordshire, U K (1996); Milgrom et al. New Engl. J. Med. 341:1966-1973 (1999); Slamon et al. New Engl. J. Med. 344:783-792 (2001); Beniaminovitz et al. New Engl. J. Med. 342:613-619 (2000); Ghosh et al. New Engl. J. Med. 348:24-32 (2003); Lipsky et al. New Engl. J. Med. 343: 1594-1602 (2000)).

Determination of the appropriate dose of the polypeptide or polypeptides is made by one skilled in the art, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Nucleic Acids, Vectors, Host Cells, and Methods of Making

The disclosure also encompasses nucleic acid or nucleic acids encoding the polypeptide or polypeptides described herein, a vector or vectors comprising the nucleic acid or nucleic acids, and host cells comprising the nucleic acid or nucleic acids or the vector or vectors.

The polypeptide or polypeptides described herein may be produced in bacterial or eukaryotic cells. Some polypeptides, e.g., Fab's, can be produced in bacterial cells, e.g., *E. coli* cells. Polypeptides can also be produced in eukaryotic cells such as transformed cell lines (e.g., CHO, 293E, COS, 293T, Hela). In addition, polypeptides (e.g., scFv's) can be expressed in a yeast cell such as *Pichia* (see, e.g., Powers et al., J Immunol Methods. 251:123-35 (2001)), *Hanseula*, or *Saccharomyces*. To produce the antibody of interest, a polynucleotide or polynucleotides encoding the polypeptide or polypeptides is/are constructed, introduced into an expression vector or expression vectors, and then expressed in suitable host cells. To improve expression, the nucleotide sequences of the genes can be recoded without changing (or minimally changing—e.g., removal of a C-terminal residue of the heavy or light chain) the amino acid sequence. The areas for potential recoding include those associated with translation initiation, codon usage, and possible unintended mRNA splicing. Polynucleotides encoding an Fc region variant described herein would be readily envisioned by the ordinarily skilled artisan.

Standard molecular biology techniques can be used to prepare the recombinant expression vector(s), transfect the host cells, select for transformants, culture the host cells, and recover the polypeptide (e.g., antibody).

If the polypeptide or polypeptides is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.*, 169:4379 (1987)) may be used as the signal sequence for antibody secretion. For bacterial expression, calcium chloride methods or electroporation methods may be used to introduce the expression vector into the bacterial cell.

If the polypeptide or polypeptides is to be expressed in animal cells such as CHO, COS, and NIH3T3 cells, the expression vector includes a promoter necessary for expression in these cells, for example, an SV40 promoter (Mulligan et al., *Nature*, 277:108 (1979)) (e.g., early simian virus 40 promoter), MMLV-LTR promoter, EF1α promoter (Mizushima et al., *Nucleic Acids Res.*, 18:5322 (1990)), or CMV promoter (e.g., human cytomegalovirus immediate early promoter). In addition to the nucleic acid sequence encoding the Fc region variant, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In some embodiments, the polypeptide or polypeptides are produced in mammalian cells. Exemplary mammalian host cells for expressing polypeptide or polypeptides include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of the antibody is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Methods of Treatment

The polypeptide or polypeptides disclosed herein can be used to treat or prevent any disease or disorder in a dog in need thereof. This invention is particularly helpful in the treatment of chronic conditions where repeated dosing is required. Because of the increased half-life of the protein therapeutic, less frequent dosing and/or reduced dose levels may be possible.

In some embodiments, the disease, disorder, condition or symptoms being treated or prevented is an allergic disease, a chronic pain, an acute pain, an inflammatory disease, an autoimmune disease, an endocrine disease, a gastrointestinal disease, a skeletal/musculoskeletal disease, a cardiovascular disease, a neurological disease, a renal disease, a metabolic disease, a immunological disease, a genetic/inherited disease, a fertility related disorder, an infectious disease or a cancer. In certain embodiments, the disease or disorder being treated or prevented is atopic dermatitis, allergic dermatitis, food allergy, osteoarthritic pain, perioperative pain, dental pain, cancer pain, arthritis, anemia, obesity, or diabetes.

Antibodies may not only be used to treat or prevent disease but also to modulate normal biological function, for example, to manage fertility or behavior.

Diagnosis

The polypeptide or polypeptides disclosed herein can also be used for various diagnostic purposes, for example, to determine whether a dog has any particular disease or disorder. In some embodiments, the polypeptide or polypeptides may comprise a binding domain. The binding domain can specifically bind to a protein, subunit, domain, motif, and/or epitope as described herein (e.g., a maker for cancer cells). In some embodiments the polypeptide or polypeptides further comprises a labeling group. In general, label groups fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

In some embodiments, the labeling group is a probe, a dye (e.g., a fluorescent dye), or a radioactive isotope (e.g., $^3$H, $^{14}$C, $^{22}$Na, $^{36}$Cl, $^{35}$S, $^{33}$P, or $^{125}$I).

Specific labels can also include optical dyes, including, but not limited to, chromophores, phosphors and fluorophores, with the latter being specific in many instances. Fluorophores can be either "small molecule" fluores, or proteinaceous fluores.

The fluorescent label can be any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, which is incorporated by reference in its entirety.

Suitable proteinaceous fluorescent labels also include, but are not limited to, green fluorescent protein, including a Renilla, Ptilosarcus, or Aequorea species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference in the entirety.

Assays

Fc$_\varepsilon$RI and FcγRIII Binding:

Binding to FcγRI and FcγRIII is a measure of the ability of an antibody to mediate ADCC. In order to assess this property for an antibody an assay to measure binding of the antibody to FcγRI and FcγRIII can be conducted using methods known in the art.

C1 q Binding:

Binding to the first component of complement, C1q, is a measure of the ability of an antibody to mediate complement-dependent cytotoxicity (CDC). In order to assess this property for an antibody, an assay to measure binding of the antibody to C1q can be conducted using methods known in the art.

Half-Life:

Methods of measuring half-life of an antibody is well known in the art. See, e.g., Booth et al., MAbs, 10(7):1098-1110 (2018). Exemplary animal models include non-human primate models and transgenic mouse models. The transgenic mouse models (e.g. Tg32 or Tg276 transgenic mice) can be null for mouse FcRn alpha chain and express the human FcRn alpha transgene (e.g. under the control of a constitutive promoter). The human FcRn alpha chain can pair in vivo with the mouse β2-microglobulin protein forming a functional chimeric FcRn heterodimer. As an example, the half-life of a canine antibody can be measured by injection of the antibody into a dog model and measuring levels of the antibody in the serum over a certain period of time.

EXAMPLES

Example 1: Alanine Scanning Mutagenesis of CH2 and CH3 Domains of Canine IgGB

Alanine scanning mutagenesis (Morrison and Weiss, Curr. Opin. Chem. Biol. 5: 302-307 (2001)) was completed on residues 250, 251, 252, 254, 256, 285, 286, 307, 309, 311, 315 in the CH2 domain and residues 378, 380, 428, 430, 433, 434, 435, and 436 in the CH3 domain. For this experiment, the wild-type (wt) sequence of the CH2 and CH3 domains of canine IgG.B was synthesized and used as template for the mutagenesis. Each specified position with the exception of position 254 was individually changed to alanine by PCR mutagenesis using a primer encoding the change. Position 254 is alanine in the wild-type sequence, and it was modified to serine. The PCR product was subcloned into the GenScript FASEBA plasmid, transformed into E. coli and sequence verified for the presence of the variant. Upstream of the CH2 domain is the SASA (single-domain antibody against serum albumin) tag (See, e.g. US 2013/0129727A1) which has pM affinity for albumin. The PelB (pectate lyase B) signal peptide is at the N-terminus to facilitate secretion of the Fc into the medium. The expression of CH2-CH3 protein was regulated by the Lac promoter. The supernatants from conditioned medium were analyzed for binding to canine FcRn (UniProtKB-E2ROL6 [FcRn] and UniProtKB-E2RN10 [canine beta-2-microglobulin]) at pH 5.5 using surface plasmon resonance (SPR).

Figure 7U:
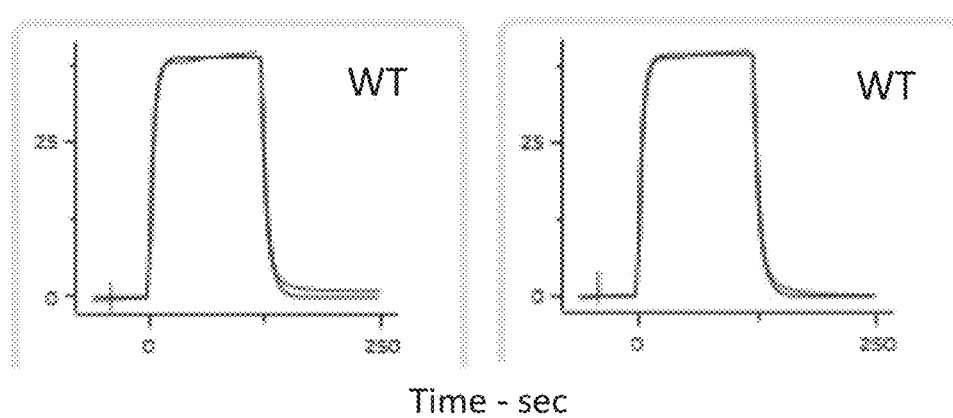
Figure 9A:
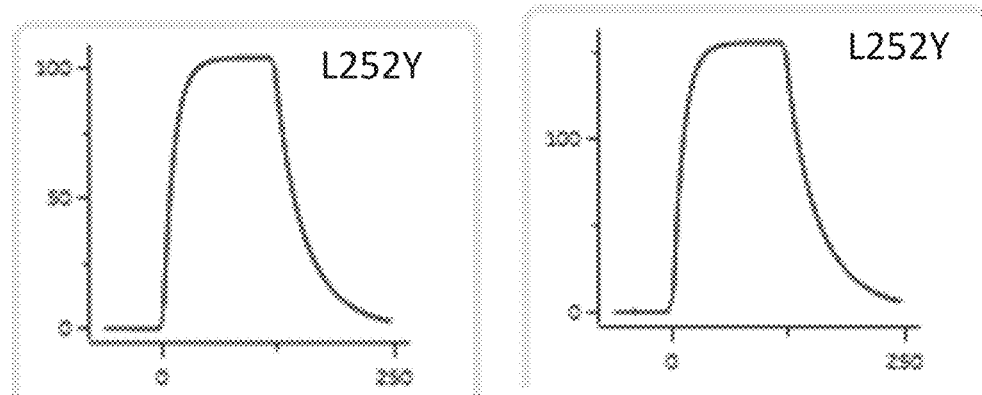
FIGS. 9A-9C depict Biacore sensorgrams for wild type and the different variants from the NNK libraries at position 252. The lighter line on each figure represents the measured data and the darker line is the fitted curve using a 1:1 interaction model.
Figure 9B:
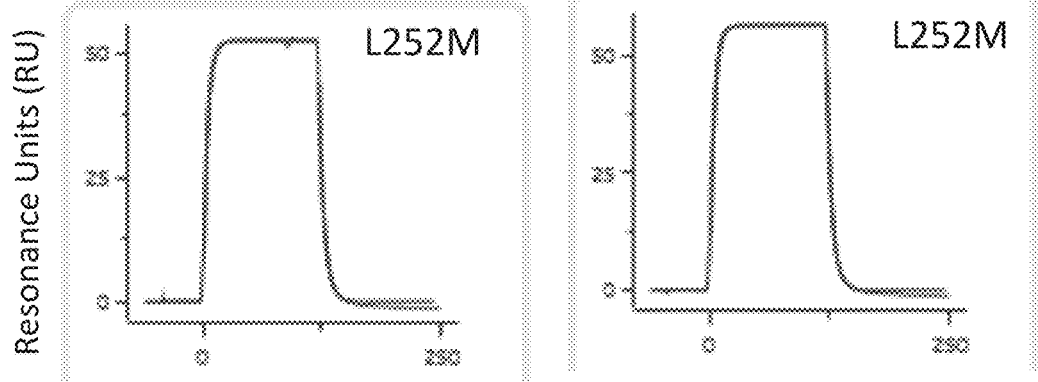
Figure 9C:
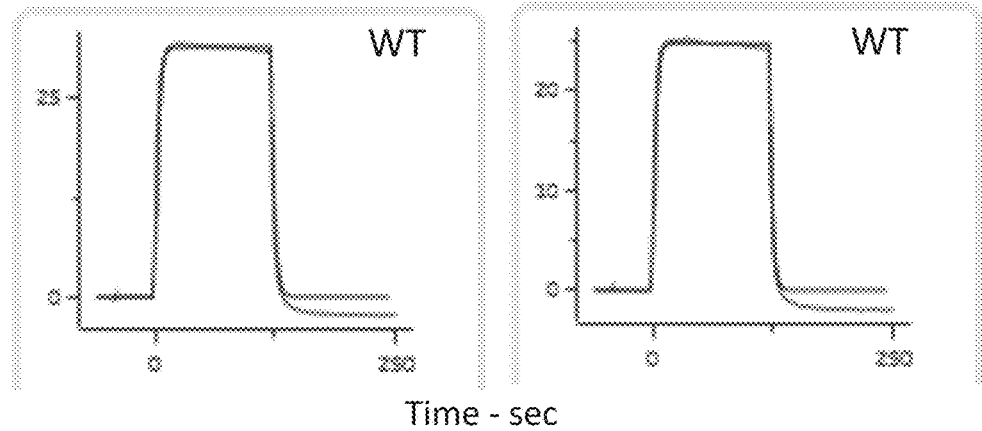
Figure 10A:
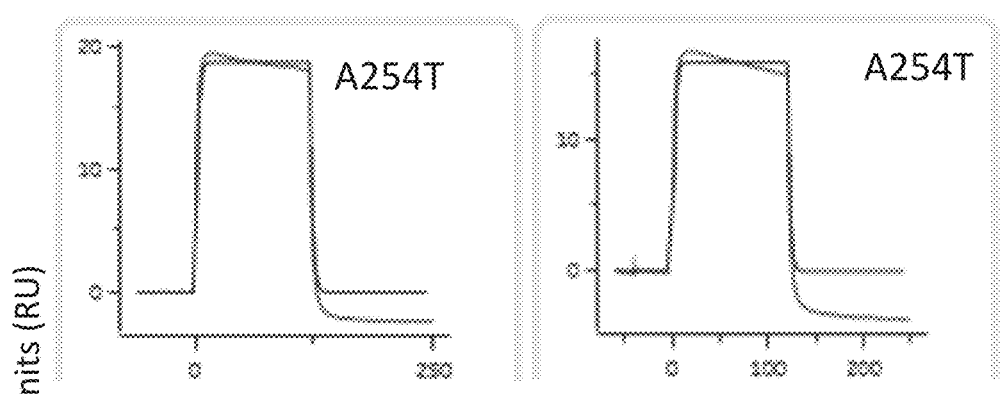
FIGS. 10A and 10B depict Biacore sensorgrams for wild type and the variant A254T. The lighter line represents the measured data and the darker line represents the fitted curve using a 1:1 interaction model.
Figure 10B:
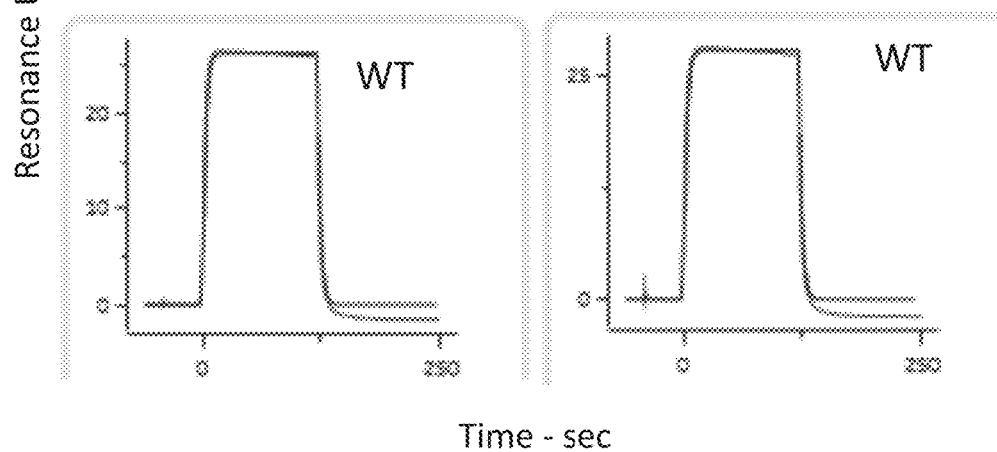
Figure 11A:
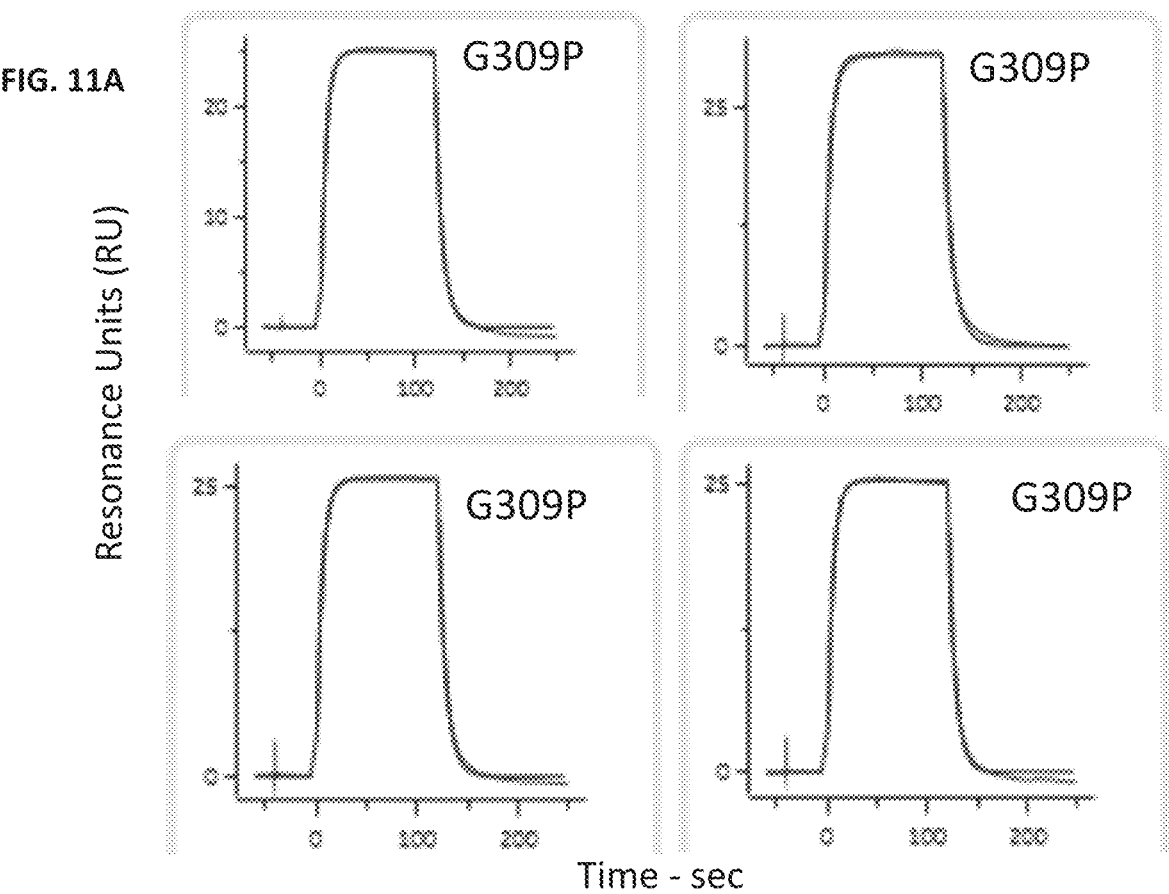
FIGS. 11A and 11B depict Biacore sensorgrams for wild type and the variant G309P. The lighter line represents the measured data and the darker line represents the fitted curve using a 1:1 interaction model.
Figure 11B:
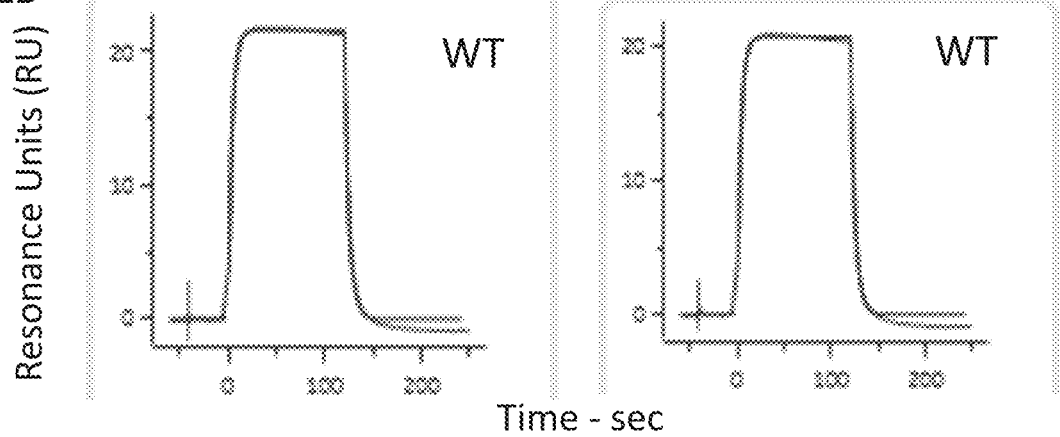
Figure 12A:
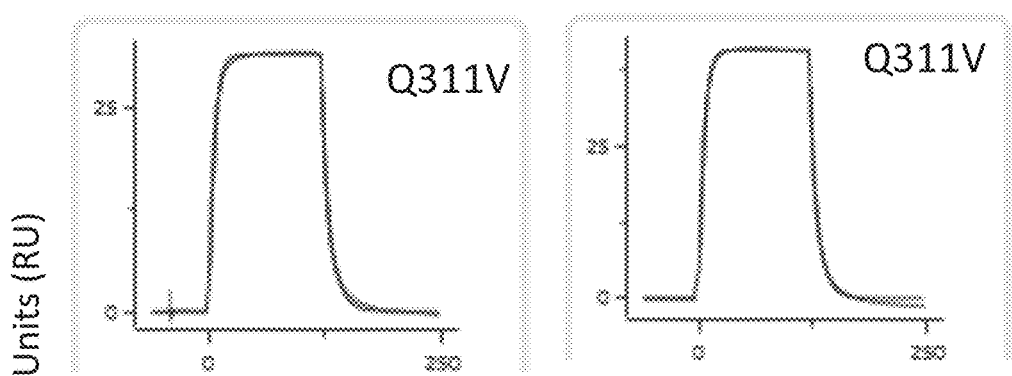
FIGS. 12A and 12B depict Biacore sensorgrams for wild type and the variant Q311V. The lighter line represents the measured data and the darker line represents the fitted curve using a 1:1 interaction model.
Figure 12B:
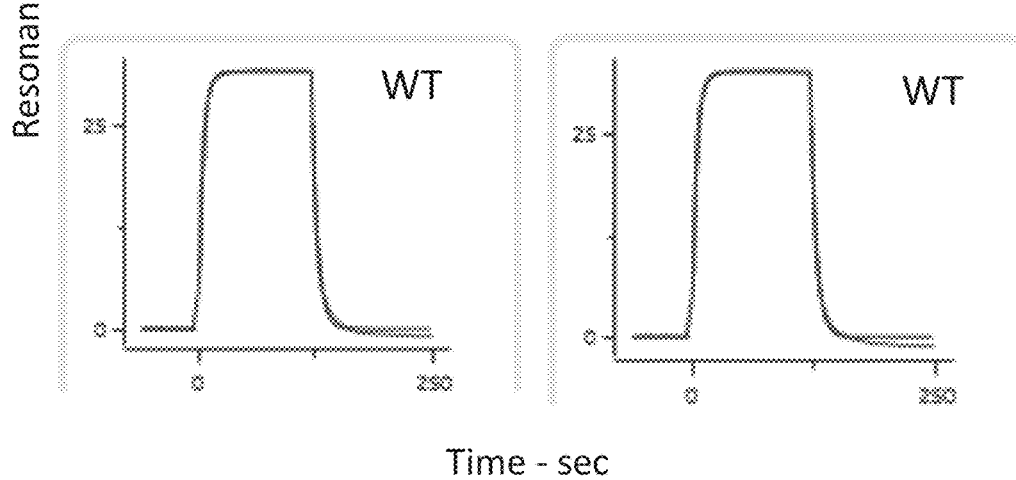
Figure 13A:
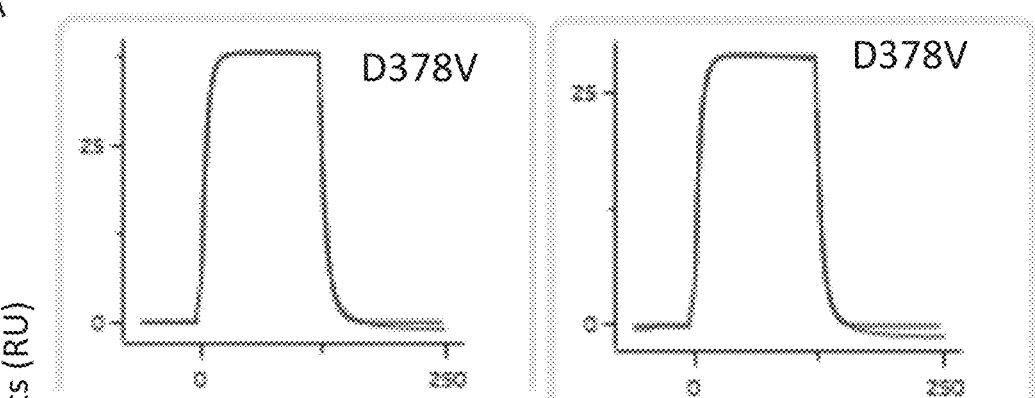
FIGS. 13A and 13B depict Biacore sensorgrams for wild type and the variant D378V. The lighter line represents the measured data and the darker line represents the fitted curve using a 1:1 interaction model.
Figure 13B:
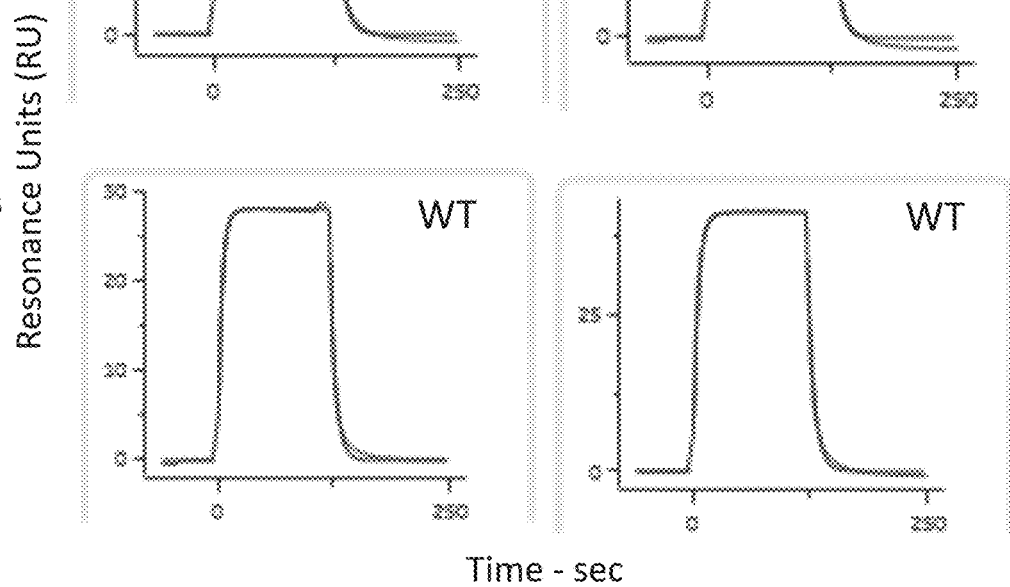
Figures 14A, 14B:
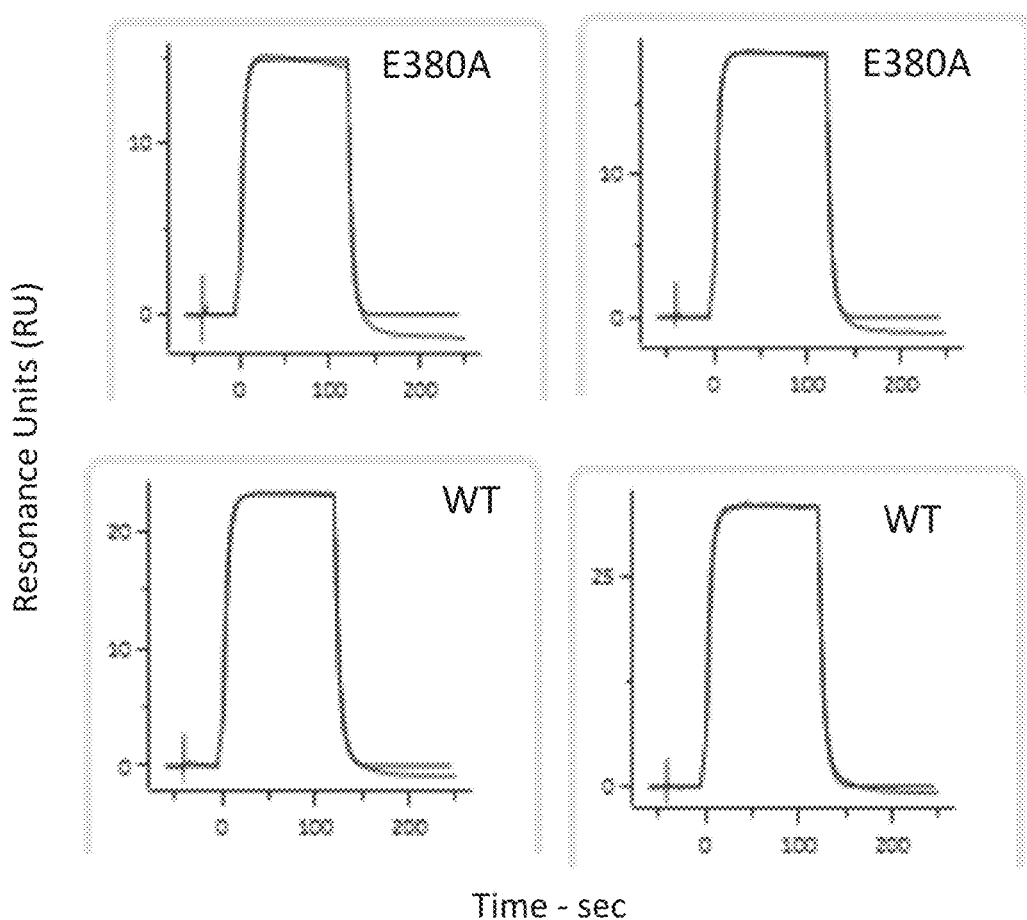
FIGS. 14A and 14B depict Biacore sensorgrams for wild type and the variant E380A. The lighter line represents the measured data and the darker line represents the fitted curve using a 1:1 interaction model.
Figure 15A:
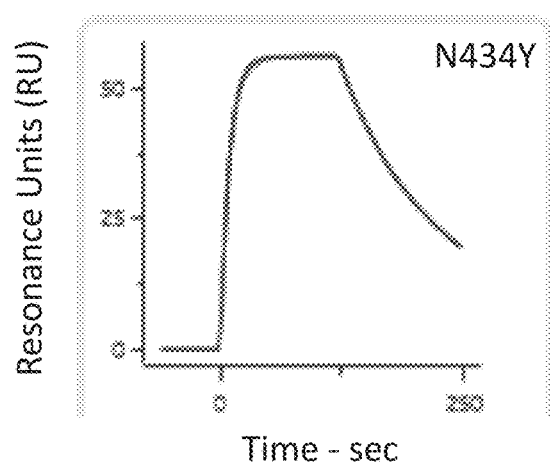
Figure 15B:
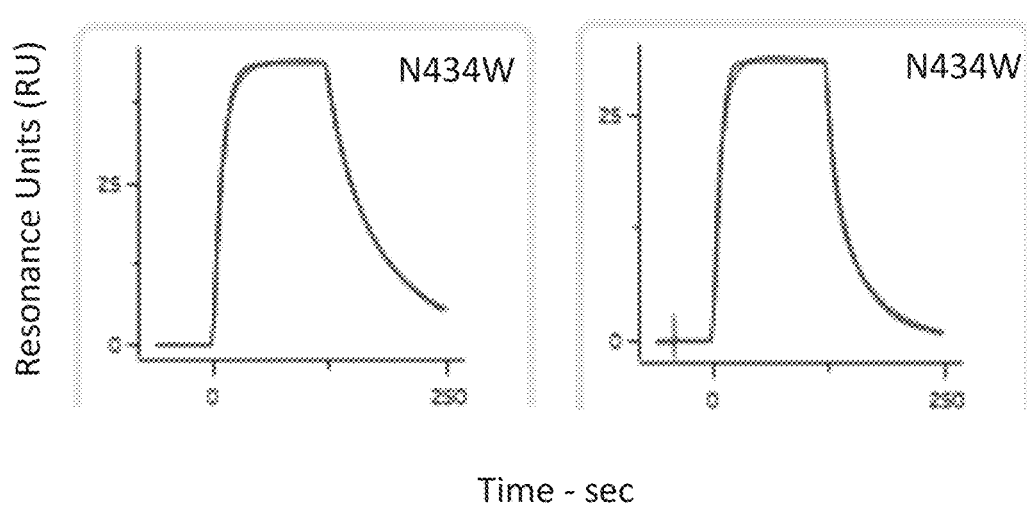
Figure 15C:
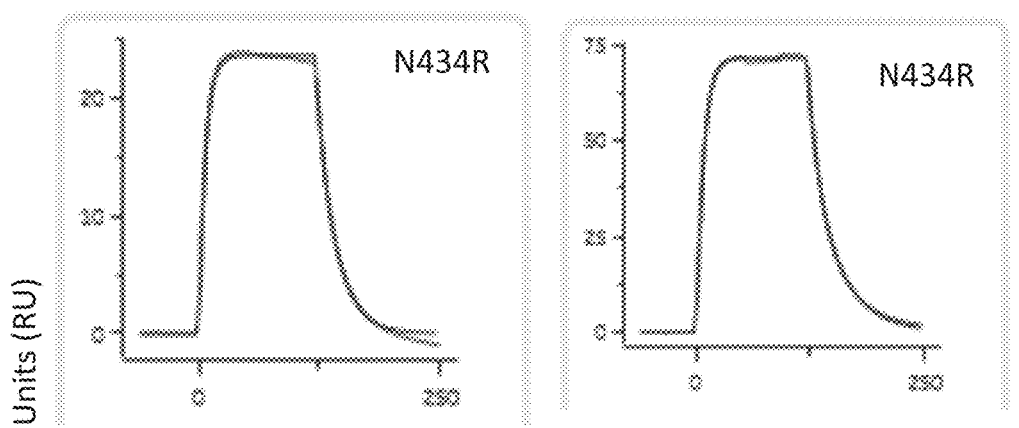
Figure 15D:
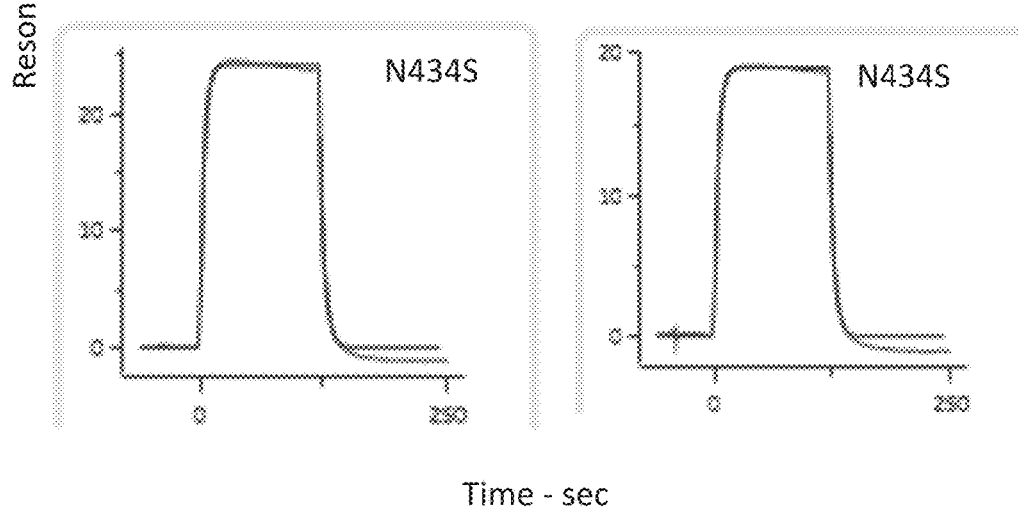
Figure 16A:
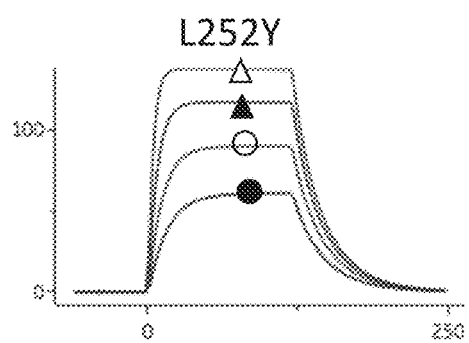
FIGS. 16A-16E depict Biacore sensorgrams for different variants in a concentration series. The concentration of canine FcRn used were 100 nM (white circle), 200 nM (black circle), 400 nM (black triangle), and 800 nM (white triangle). The lighter line on each figure is the measured data and the darker line is the fitted curve using a 1:1 interaction model.
Figure 16B:
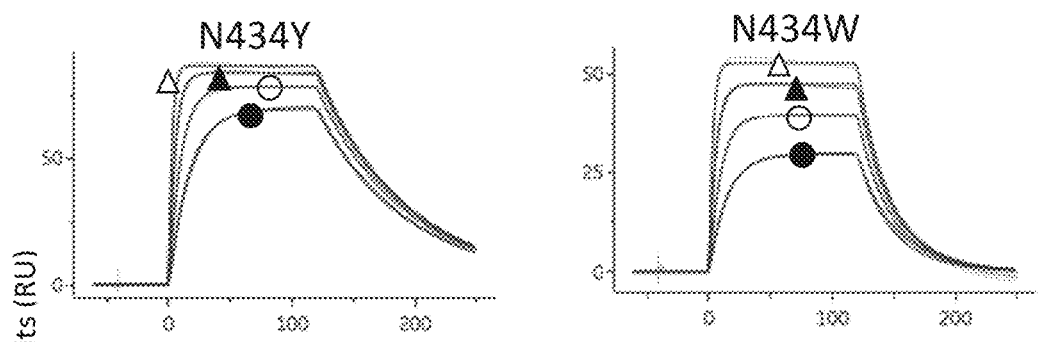
Figure 16C:
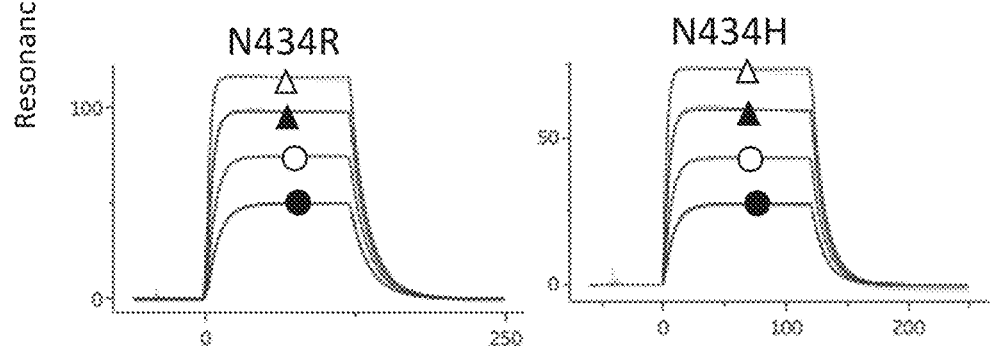
Figure 16D:
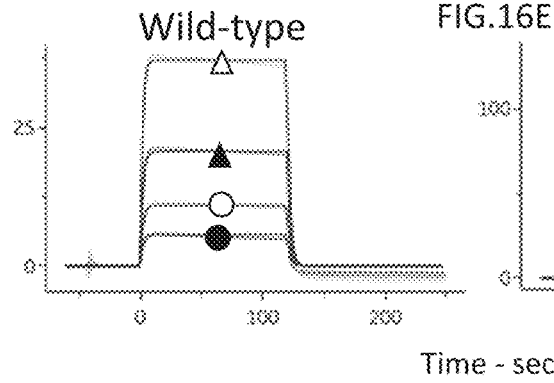
Figure 16E:
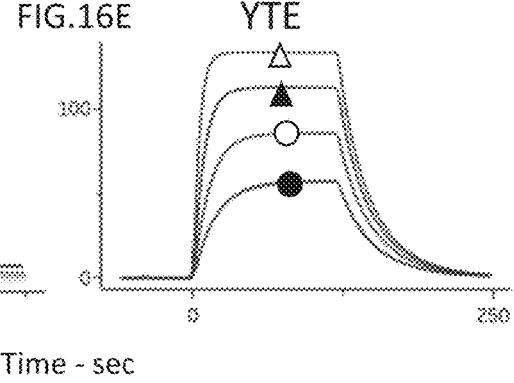

For the SPR analyses using Biacore 8K, bovine serum albumin (BSA) was immobilized to CM5 sensor chip. The sensor chip surface of flow cells 1 and 2 were activated by freshly mixed 50 mmol/L N-Hydroxysuccinimide and 200 mmol/L 1-ethyl-3-(3-dimethylaminopropyl) carbodiimide hydrochloride for 420 s (10 µL/min). Afterwards, BSA diluted in 10 mM sodium acetate (pH 4.5) was injected into the flow cell 2 to achieve conjugation, while flow cell 1 was set as blank. After the amine coupling reaction, the remaining active coupling sites on chip surface were blocked with 420 s injection of 1 mM ethanolamine hydrochloride. The running buffer for the binding experiment was HBS-EP (10 mM HEPES, 500 mM NaCl, 3 mM EDTA, 0.05% Tween 20, pH 5.5) and it was run at 25° C. Supernatants from the alanine variants were injected over chip surface and captured via the SASA tag onto the immobilized BSA for 60 sec. Canine FcRn at 400 nM was injected for 120 sec and the dissociation was complete with running buffer for 120 sec. The flow rate for the immobilization phase of BSA was 10 µl/min and the flow rate for the association and dissociation phase was 30 µl/min. All of the data was processed using the Biacore 8K evaluation software version 1.1. The tabulated data is shown in Table 3 with the last column containing the average KD of wild-type divided by the variant KD. The sensorgrams are shown in FIGS. 7A-7U.

TABLE 3

| Variant | ka (1/Ms) | kd (1/s) | KD (M) | Comments | WT KD Avg/Variant KD |
|---|---|---|---|---|---|
| T250A | 1.86E+07 | 6.24E+00 | 3.35E-07 |  | 1.69 |
| T250A | 3.87E+06 | 1.27E+00 | 3.28E-07 |  | 1.72 |
| L251A |  |  |  | Binding not detected |  |
| L251A |  |  |  | Binding not detected |  |
| L252A | 3.32E+05 | 9.69E-02 | 2.92E-07 |  | 1.94 |
| L252A | 2.36E+06 | 5.67E-01 | 2.40E-07 |  | 2.36 |
| A254S | 7.91E+06 | 2.69E+00 | 3.40E-07 |  | 1.66 |
| A254S | 2.39E+06 | 7.58E-01 | 3.17E-07 |  | 1.78 |
| T256A | 3.71E+05 | 1.66E-01 | 4.47E-07 |  | 1.27 |
| T256A | 2.43E+08 | 7.24E+01 | 2.98E-07 |  | 1.90 |
| Q285A | 3.28E+05 | 1.12E-01 | 3.41E-07 |  | 1.66 |
| Q285A | 1.37E+08 | 3.52E+01 | 2.57E-07 |  | 2.20 |
| T286A | 4.22E+05 | 1.96E-01 | 4.64E-07 |  | 1.22 |
| T286A | 5.33E+05 | 3.04E-01 | 5.69E-07 |  | 0.99 |
| P307A | 2.87E+08 | 9.31E+01 | 3.25E-07 |  | 1.74 |
| P307A | 3.66E+06 | 1.23E+00 | 3.38E-07 |  | 1.67 |
| I308A | 3.57E+05 | 1.69E-01 | 4.72E-07 |  | 1.20 |
| I308A | 3.45E+05 | 1.94E-01 | 5.63E-07 |  | 1.00 |
| G309A | 1.42E+06 | 3.48E-01 | 2.45E-07 |  | 2.31 |
| G309A | 2.44E+05 | 7.19E-02 | 2.94E-07 |  | 1.92 |
| Q311A | 2.43E+06 | 8.94E-01 | 3.68E-07 |  | 1.54 |
| Q311A | 1.34E+06 | 4.96E-01 | 3.70E-07 |  | 1.53 |
| K315A | 4.13E+07 | 1.74E+01 | 4.22E-07 |  | 1.34 |
| K315A | 2.45E+05 | 1.34E-01 | 5.48E-07 |  | 1.03 |
| D378A | 2.72E+05 | 1.83E-01 | 6.73E-07 |  | 0.84 |

TABLE 3-continued

| Variant | ka (1/Ms) | kd (1/s) | KD (M) | Comments | WT KD Avg/Variant KD |
|---|---|---|---|---|---|
| D378A | 3.06E+05 | 1.81E-01 | 5.92E-07 |  | 0.96 |
| E380A | 2.41E+05 | 1.80E-01 | 7.47E-07 |  | 0.76 |
| E380A | 5.98E+05 | 3.69E-01 | 6.18E-07 |  | 0.92 |
| M428A | 2.34E+05 | 1.69E-01 | 7.23E-07 |  | 0.78 |
| M428A | 3.18E+05 | 5.32E-01 | 1.67E-06 |  | 0.34 |
| E430A |  |  |  | Binding not detected |  |
| E430A |  |  |  | Binding not detected |  |
| H433A | 8.62E+05 | 2.29E-01 | 2.66E-07 |  | 2.13 |
| H433A | 2.78E+05 | 9.97E-02 | 3.59E-07 |  | 1.58 |
| N434A | 5.18E+05 | 2.37E-01 | 4.57E-07 |  | 1.24 |
| N434A | 9.66E+05 | 4.77E-01 | 4.94E-07 |  | 1.14 |
| H435A |  |  |  | Binding not detected |  |
| H435A |  |  |  | Binding not detected |  |
| Y436A | 1.04E+06 | 4.07E-01 | 3.93E-07 |  | 1.44 |
| Y436A | 2.44E+05 | 2.13E-01 | 8.76E-07 |  | 0.65 |
| Wild Type | 3.61E+06 | 1.16E+00 | 3.21E-07 |  | 1.76 |
| Wild Type | 6.32E+05 | 3.75E-01 | 5.92E-07 |  | 0.96 |
| Wild Type | 4.42E+05 | 1.85E-01 | 4.18E-07 |  | 1.35 |
| Wild Type | 5.87E+05 | 3.14E-01 | 5.34E-07 |  | 1.06 |
| Wild Type | 3.86E+05 | 1.88E-01 | 4.88E-07 |  | 1.16 |
| Wild Type | 3.91E+05 | 2.01E-01 | 5.14E-07 |  | 1.10 |
| Wild Type | 2.65E+05 | 1.60E-01 | 6.06E-07 |  | 0.93 |
| Wild Type | 3.10E+05 | 1.52E-01 | 4.89E-07 |  | 1.16 |
| Wild Type | 2.69E+05 | 1.66E-01 | 6.16E-07 |  | 0.92 |
| Wild Type | 7.80E+05 | 4.79E-01 | 6.14E-07 |  | 0.92 |
| Wild Type | 2.90E+05 | 1.35E-01 | 4.65E-07 |  | 1.22 |
| Wild Type | 1.73E+05 | 1.96E-01 | 1.13E-06 |  | 0.50 |
|  |  | WT KD Avg 5.66E-07 |  |  |  |

Example 2: Generation of NNK Saturation Mutagenesis Libraries at Selected Positions and Analysis of Individual Variants The NNK saturation mutagenesis method is an effective strategy to generate all 20 possible amino acids at a desired position (Hogrefe et al., Biotechniques. 33: 1158-1165 (2002)). Individual NNK libraries at positions 250, 252, 254, 309, 311, 378, 380, and 434 (EU numbering) were generated. For this method, NNK (N=A/C/G/T, K=G/T) primers at the specified position were used with the QuikChange Site-Directed Mutagenesis Kit (Agilent). The supernatants from ninety individual transformants from each library were assayed for binding to canine FcRn at pH 5.5 using the Biacore method described in Example 1. The only difference was the concentration of canine FcRn used in the assay was 200 nM not 400 nM. The sensorgrams for all of the NNK library variants are shown in FIGS. 8-15.

For the NNK library at position 250, none of the variants showed increased binding to canine FcRn at pH 5.5. The data from variants T250E and T250Q and wild type Fc are shown in Table 4. In a competitive binding assay, variants T250E and T250Q in human IgG2 have been demonstrated to bind tighter to human FcRn at pH 6.0 compared to wild-type human IgG2 Fc (Hinton et al., J. Biol. Chem. 279: 6213-6216 (2004)).

TABLE 4

| Variant | ka (1/Ms) | kd (1/s) | KD (M) |
|---|---|---|---|
| T250Q | 9.96E+04 | 2.58E-01 | 2.59E-06 |
| T250Q | 9.43E+04 | 2.68E-01 | 2.84E-06 |
| T250E | 1.14E+05 | 2.84E-01 | 2.48E-06 |

TABLE 4-continued

| Variant | ka (1/Ms) | kd (1/s) | KD (M) |
|---|---|---|---|
| T250E | 1.72E+05 | 2.87E−01 | 1.66E−06 |
| WT | 3.87E+04 | 3.47E−01 | 8.99E−06 |
| WT | 1.14E+05 | 3.54E−01 | 3.11E−06 |

For the NNK library at position 252, only variants L252Y and L252M had an apparent higher affinity for canine FcRn at pH 5.5 (see Table 5 below). In the 90 transformants, there were no L252F variants present so no binding data was obtained with this variant.

TABLE 5

| Variant | ka (1/Ms) | kd (1/s) | KD (M) |
|---|---|---|---|
| L252Y | 4.02E+05 | 3.97E−02 | 9.87E−08 |
| L252Y | 3.58E+05 | 4.10E−02 | 1.14E−07 |
| L252M | 1.93E+05 | 1.68E−01 | 8.69E−07 |
| L252M | 2.18E+05 | 1.69E−01 | 7.74E−07 |
| WT | 1.68E+05 | 2.88E−01 | 1.71E−06 |
| WT | 1.23E+05 | 3.26E−01 | 2.66E−06 |

For the NNK library at position 254, none of the variants tested had an apparent higher affinity for canine FcRn at pH 5.5. Data for the A254T variant is shown in Table 6 and the corresponding variant in human IgG1 has been used in the YTE variant (M252Y/S254T/T256E) which has an increased affinity to human FcRn at pH 6.0 (Dall'Acqua et al., J. Immunol. 169: 5171-5180 (2002)) and been demonstrated to increase the half-life of human IgG in preclinical models as well as in humans (Borrok et al., J. Biol. Chem. 290: 4282-4290 (2015); Robbie et al., Antimicrob. Agents Ch. 57: 6147-6153 (2013)). In the 90 transformants, there were no A254H variants present so no data was obtained with this variant.

TABLE 6

| Variant | ka (1/Ms) | kd (1/s) | KD (M) |
|---|---|---|---|
| A254T | 1.63E+05 | 3.75E−01 | 2.29E−06 |
| A254T | 3.23E+05 | 4.33E−01 | 1.34E−06 |
| WT | 1.51E+05 | 3.10E−01 | 2.05E−06 |
| WT | 1.05E+05 | 3.15E−01 | 2.99E−06 |

For the NNK libraries at positions 309 and 311, none of the variants tested had an apparent higher affinity for canine FcRn at pH 5.5. Data for the variants G309P and Q311V are shown in Tables 7 and 8 and the corresponding human variants (L309P and Q311V) in human IgG1 in several combinations with other variants have been demonstrated to have a higher affinity for human FcRn at pH 6.0 (Dall'Acqua et al., J. Immunol. 169: 5171-5180 (2002); Booth et al., MAbs, 10(7):1098-1110 (2018)). The variants G309D, G309K and Q311D were not identified in the NNK libraries and therefore were not tested for FcRn binding.

TABLE 7

| Variant | ka (1/Ms) | kd (1/s) | KD (M) |
|---|---|---|---|
| G309P | 3.77E+05 | 2.39E−01 | 6.35E−07 |
| G309P | 5.58E+05 | 2.42E−01 | 4.34E−07 |
| G309P | 2.07E+05 | 1.32E−01 | 6.37E−07 |
| G309P | 2.02E+05 | 1.45E−01 | 7.18E−07 |
| WT | 2.37E+05 | 2.10E−01 | 8.84E−07 |
| WT | 2.53E+05 | 2.18E−01 | 8.62E−07 |

TABLE 8

| Variant | ka (1/Ms) | kd (1/s) | KD (M) |
|---|---|---|---|
| Q311V | 1.52E+06 | 5.66E−01 | 3.72E−07 |
| Q311V | 1.59E+06 | 6.96E−01 | 4.39E−07 |
| WT | 2.67E+05 | 1.70E−01 | 6.39E−07 |
| WT | 2.47E+05 | 1.71E−01 | 6.92E−07 |

For the NNK libraries at positions 378 and 380, none of the variants tested had an apparent higher affinity for canine FcRn at pH 5.5. The data for variant D378V is shown in Table 9 and the corresponding variant in human IgG1 has been used in combinations with other IgG variants to demonstrate higher affinity to human FcRn at pH 6.0 compared to wild-type Fc and extending the half-life of human IgG in transgenic human FcRn mice (Monnet et al., MABS. 6: 422-436 (2014); Booth et al., 2018). Also, the data for variant E380A is shown in Table 10 and the corresponding variant in human IgG has been shown to have higher binding affinity to human FcRn at pH 6.0 (Shields et al., J. Biol. Chem. 276: 6591-6604 (2001)). Variants D378E, D378I, D378K, and E380F were not present in the NNK libraries and not screened for binding to canine FcRn.

TABLE 9

| Variant | ka (1/Ms) | kd (1/s) | KD (M) |
|---|---|---|---|
| D378V | 2.29E+05 | 1.59E−01 | 6.93E−07 |
| D378V | 1.84E+05 | 1.60E−01 | 8.73E−07 |
| WT | 3.36E+05 | 1.69E−01 | 5.02E−07 |
| WT | 2.64E+05 | 2.07E−01 | 7.84E−07 |

TABLE 10

| Variant | ka (1/Ms) | kd (1/s) | KD (M) |
|---|---|---|---|
| E380A | 1.68E+05 | 2.23E−01 | 1.32E−06 |
| E380A | 1.52E+05 | 2.39E−01 | 1.57E−06 |
| WT | 1.15E+05 | 1.79E−01 | 1.56E−06 |
| WT | 2.42E+05 | 1.82E−01 | 7.54E−07 |

For the NNK library at position 434, variants N434Y, N434W, and N434R had a higher affinity for canine FcRn at pH 5.5 shown in Table 11. Variants N434S and N434A did not have a higher affinity for canine FcRn at a low pH which is unlike the corresponding human IgG1 variants (Petkova et al., Int. Immunol. 18: 1759-1769 (2006); Yeung et al., J. Immunol. 182: 7663-7671 (2009); Zalevsky et al., Nat. Biotechnol. 28: 157-159 (2010); Deng et al., Drug Metab. Dispos. 38: 600-605 (2010)). The NNK library screened at position 434 did not contain the N434F variant so the binding of this variant to canine FcRn was not tested.

TABLE 11

| Variant | ka (1/Ms) | kd (1/s) | KD (M) |
|---|---|---|---|
| N434Y | 6.07E+05 | 9.68E−03 | 1.59E−08 |
| N434W | 6.93E+05 | 2.80E−02 | 4.04E−08 |
| N434W | 4.20E+06 | 3.18E−01 | 7.57E−08 |
| N434R | 4.88E+05 | 5.24E−02 | 1.07E−07 |
| N434R | 3.99E+05 | 6.33E−02 | 1.59E−07 |
| N434S | 2.25E+05 | 2.07E−01 | 9.24E−07 |
| N434S | 1.99E+05 | 2.09E−01 | 1.05E−06 |
| N434A | 2.72E+05 | 1.56E−01 | 5.73E−07 |

TABLE 11-continued

| Variant | ka (1/Ms) | kd (1/s) | KD (M) |
|---|---|---|---|
| N434A | 2.61E+05 | 1.64E−01 | 6.29E−07 |
| WT | 1.90E+05 | 1.81E−01 | 9.55E−07 |
| WT | 1.59E+05 | 2.09E−01 | 1.31E−06 |

Example 3: Binding Kinetics for L252Y, N434Y, N434W, N434R, N434H and YTE (L252Y/A254T/T256E) Variants and Wild-Type Fc Several canine IgG.B variants that demonstrated higher affinity to canine FcRn at pH 5.5 were further evaluated for binding kinetics to canine FcRn. In this study, the binding of the variants (L252Y, N434Y, N434W, N434R, N434H), YTE variant (L252Y/A254T/T256E) and wild-type canine Fc to canine FcRn at pH 5.5 and pH 7.4 was evaluated. The Biacore method for the pH 5.5 condition was the same as described in Example 1 with the exception that four concentrations of FcRn (100 nM, 200 nM, 400 nM, 800 nM) were tested which yields more precise binding kinetics. For the Biacore conditions at pH 7.4, the running buffer used was 10 mM HEPES, 500 mM NaCl, 3 mM EDTA, 0.05% Tween 20, pH 7.4 and the concentration of canine FcRn tested was 200 nM. All of the variants (including YTE), as well as the wild type did not bind to canine FcRn at pH 7.4. The binding kinetics at pH 5.5 are shown in Table 12 and the sensorgrams are shown in FIGS. 16A-16E. The variants tested showed increased affinity for canine FcRn at pH 5.5 as compared to wild type Fc.

TABLE 12

| Variant | ka (1/Ms) | kd (1/s) | KD (M) |
|---|---|---|---|
| L252Y | 2.75E+05 | 4.76E−02 | 1.73E−07 |
| N434Y | 5.20E+05 | 1.51E−02 | 2.91E−08 |
| N434W | 4.46E+05 | 4.50E−02 | 1.01E−07 |
| N434R | 4.40E+05 | 8.01E−02 | 1.82E−07 |
| N434H | 4.11E+05 | 1.02E−01 | 2.47E−07 |
| Wild Type | 1.68E+05 | 5.27E−01 | 3.15E−06 |
| YTE | 2.50E+05 | 4.60E−02 | 1.84E−07 |

Example 4: Generation of NNK Saturation Mutagenesis Libraries at Selected Positions and Analysis of Individual Variants The wild-type (wt) sequence of the CH2 and CH3 domains of canine IgGB (SEQ ID NO:10) was synthesized and used as template for the NNK mutagenesis. The NNK saturation mutagenesis method is an effective strategy to generate all 20 possible amino acids at a desired position (Hogrefe et al., Biotechniques. 33: 1158-1165 (2002)). Individual NNK libraries at positions 286, 312, 426, and 436 (EU numbering) were generated. NNK (N=A/C/G/T, K=G/T) primers at the specified position were used with the QuikChange Site-Directed Mutagenesis Kit (Agilent). The PCR-product was subcloned into the GenScript FASEBA plasmid, transformed into E. coli and sequenced verified for the presence of the variant. Upstream of the CH2 domain is the SASA (single-domain antibody against serum albumin) tag (Zhang, J.; Wu, S.; Liu, J. Methods and systems for increasing protein stability. US patent application, 2013.) which has pM affinity for albumin. The SASA antibody enables the capture of the Fc to the sensor chip surface described below. The PelB (pectate lyase B) signal peptide is at the N-terminus to facilitate secretion of the Fc into the medium. The expression of CH2-CH3 protein was regulated by the Lac promoter. The supernatants from conditioned medium were analyzed for binding to canine FcRn (UniProtKB-E2ROL6 [FcRn] and UniProtKB-E2RN10 [canine beta-2-microglobulin]) at pH 5.5 for variants at position 426 and 312 and at pH 6.0 for variants at position 286 and 436 using surface plasmon resonance (SPR).

The supernatants from ninety individual transformants from each library were assayed for binding to canine FcRn at pH 5.5 for variants at position 426 and 312 and at pH 6.0 for variants at position 286 and 436 using the Biacore method, as described below.

Figure 17A:
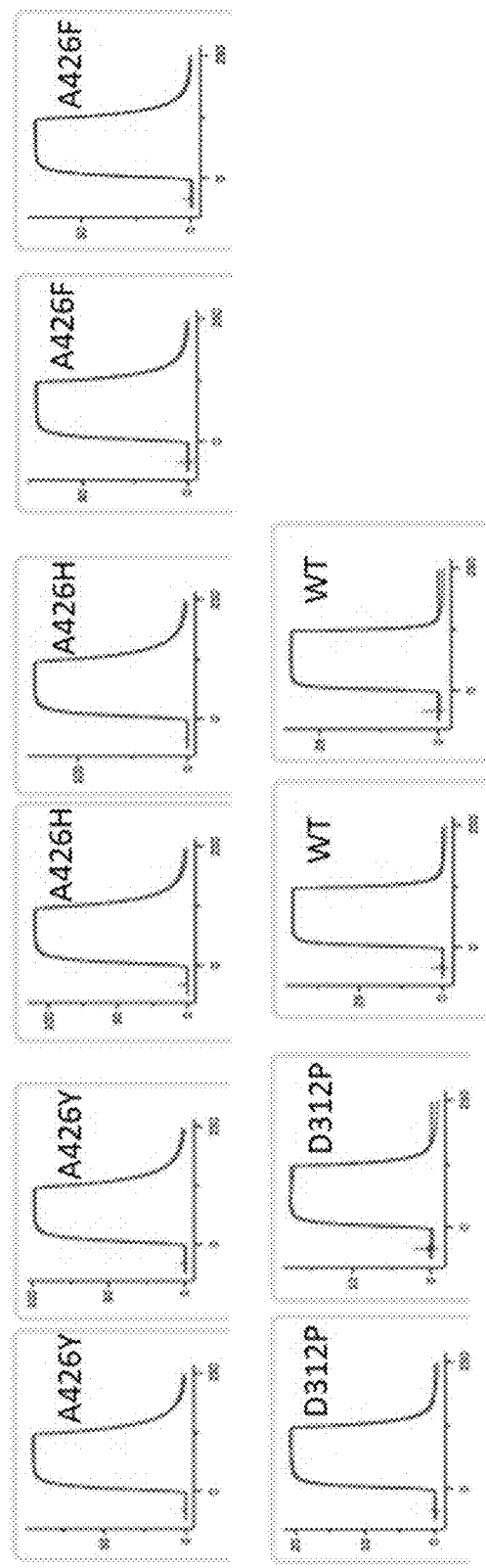
FIGS. 17A-17B depict Biacore NNK Library sensorgrams for different variants. The concentration of canine FcRn used was 200 nM. The lighter line on each figure is the measured data and the darker line is the fitted curve using a 1:1 interaction model.
Figure 17B:
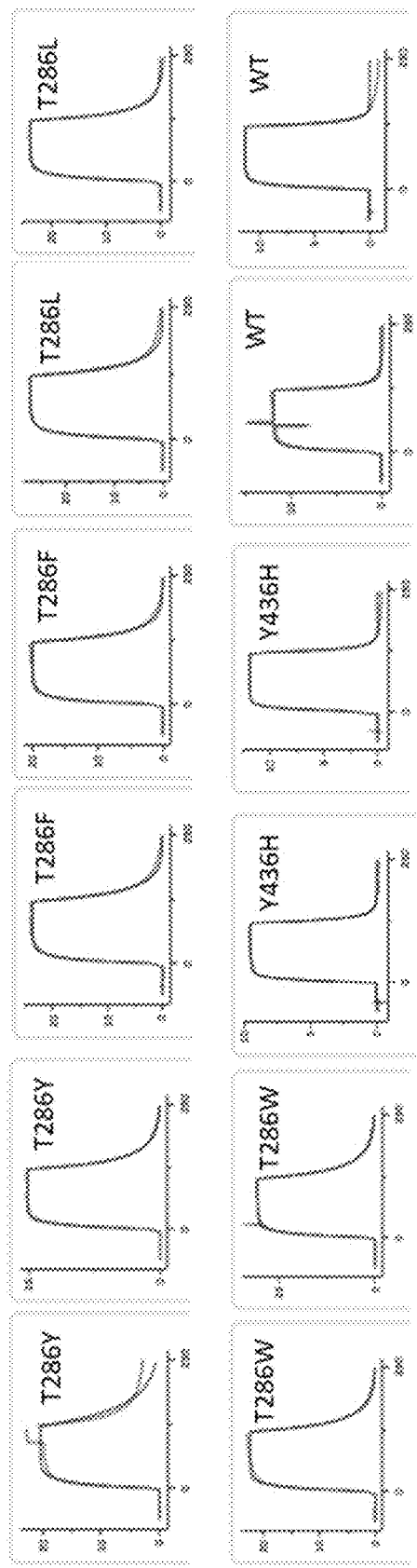

For the SPR analyses using the Biacore 8K, bovine serum albumin (BSA) was immobilized to CM5 sensor chip. The sensor chip surface of flow cells 1 and 2 were activated by freshly mixed 50 mmol/L N-Hydroxysuccinimide and 200 mmol/L 1-ethyl-3-(3-dimethylaminopropyl) carbodiimide hydrochloride for 420 s (10 µL/min). Afterwards, BSA diluted in 10 mM sodium acetate (pH 4.5) was injected into the flow cell 2 to achieve conjugation, while flow cell 1 was set as blank. After the amine coupling reaction, the remaining active coupling sites on chip surface were blocked with 420 s injection of 1 mM ethanolamine hydrochloride. The running buffer for the binding experiment was HBS-EP (10 mM HEPES, 500 mM NaCl, 3 mM EDTA, 0.05% Tween 20, pH 5.5) and it was run at 25° C. Supernatants from the variants were injected over chip surface and captured via the SASA tag onto the immobilized BSA for 60 sec. Canine FcRn at 200 nM was injected for 120 sec and the dissociation was complete with running buffer for 120 sec. The flow rate for the immobilization phase of BSA was 10 µl/min and the flow rate for the association and dissociation phase was 30 µl/min. All of the data was processed using the Biacore 8K evaluation software version 1.1. See FIG. 17 for the Biacore sensorgrams.

The variants tested showed increased binding affinity for canine FcRn at pH 5.5 (for variants with an amino acid substitution at position 312 or 426) and at pH 6.0 (for variants with an amino acid substitution at position 286 or 436) when compared to wild type canine IgGB Fc (SEQ ID NO:10). The results are summarized in Tables 13 and 14, below.

TABLE 13

| Variant | ka (1/Ms) | kd (1/s) | KD (M) |
|---|---|---|---|
| A426Y | 7.50E+05 | 1.09E−01 | 1.46E−07 |
| A426Y | 7.85E+05 | 1.12E−01 | 1.43E−07 |
| A426H | 8.43E+05 | 1.35E−01 | 1.60E−07 |
| A426H | 9.15E+05 | 1.40E−01 | 1.53E−07 |
| A426F | 7.86E+05 | 1.43E−01 | 1.82E−07 |
| A426F | 8.11E+05 | 1.47E−01 | 1.81E−07 |
| D312P | 3.07E+05 | 8.94E−02 | 2.91E−07 |
| D312P | 2.51E+05 | 1.10E−01 | 4.39E−07 |
| Wild-type | 1.94E+05 | 1.95E−01 | 1.01E−06 |
| Wild-type | 4.42E+05 | 2.97E−01 | 6.73E−07 |

TABLE 14

| Variant | ka (1/Ms) | kd (1/s) | KD (M) |
|---|---|---|---|
| T286Y | 4.10E+05 | 2.86E−02 | 6.98E−08 |
| T286Y | 1.11E+06 | 1.30E−01 | 1.16E−07 |
| T286F | 3.36E+05 | 5.27E−02 | 1.57E−07 |
| T286F | 3.30E+05 | 6.10E−02 | 1.85E−07 |
| T286L | 3.24E+05 | 5.65E−02 | 1.74E−07 |
| T286L | 4.96E+05 | 1.03E−01 | 2.08E−07 |

TABLE 14-continued

| Variant | ka (1/Ms) | kd (1/s) | KD (M) |
|---|---|---|---|
| T286W | 7.74E+05 | 9.82E-02 | 1.27E-07 |
| T286W | 9.45E+05 | 1.12E-01 | 1.18E-07 |
| Y426H | 3.00E+05 | 1.34E-01 | 4.47E-07 |
| Y426H | 2.65E+05 | 1.41E-01 | 5.32E-07 |
| Wild-Type | 1.49E+05 | 1.40E-01 | 9.39E-07 |
| Wild-Type | 1.44E+05 | 1.44E-01 | 9.99E-07 |

Figure 18A:
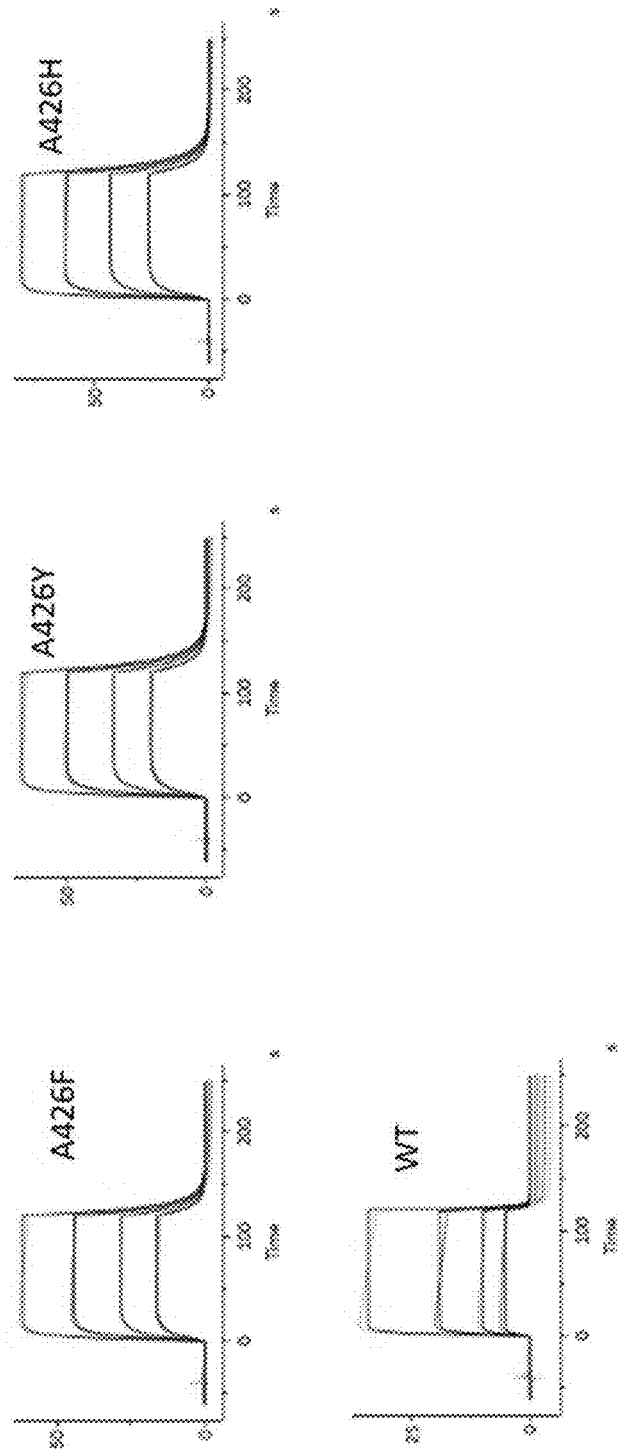
FIGS. 18A-18B depict Biacore sensorgrams for different variants in a concentration series. The concentration of canine FcRn used were (lines from the bottom to the top): 100 nM, 200 nM, 400 nM, and 800 nM, respectively. The lines are the fitted curve using a 1:1 interaction model.
Figure 18B:
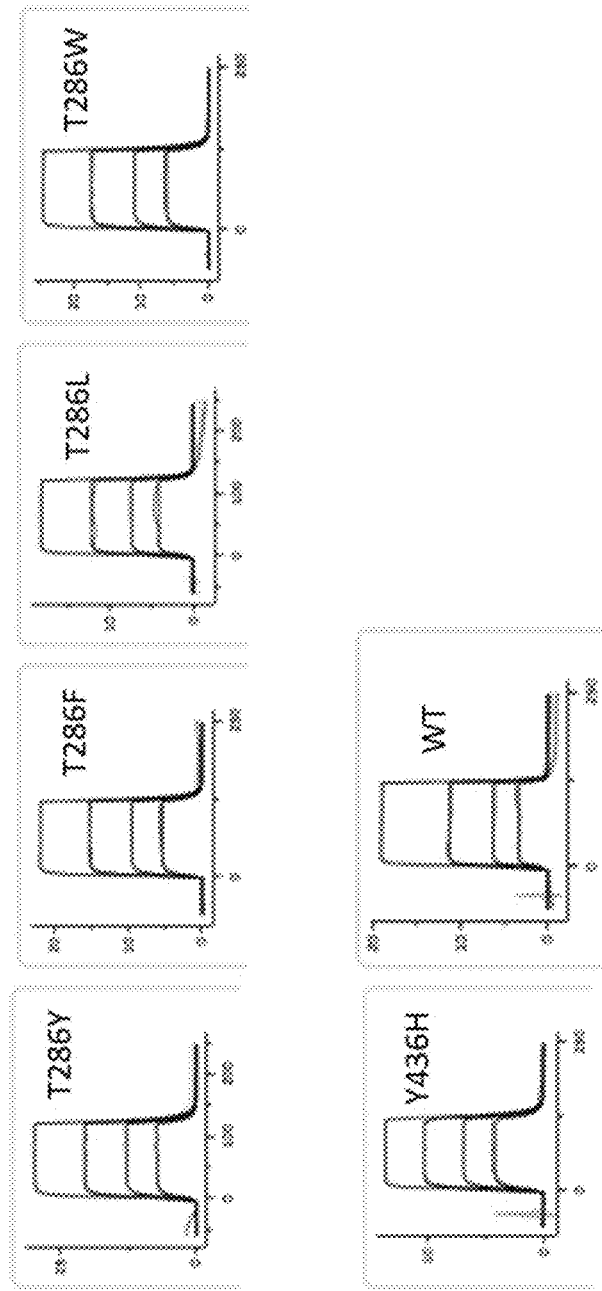

Example 5: Binding Kinetics for A426Y, A426H, A426F, T286Y, T286F, T286L, T286W, Y436H and Wild-Type Fc Several canine IgGB variants that demonstrated higher affinity to canine FcRn were further evaluated for binding kinetics to canine FcRn. In this study, the binding of the variants (A426Y, A426H, A426Y, T286Y, T286F, T286L, T286W, Y436H), YTE variant (L252Y/A254T/T256E) and wild-type canine IgGB Fc to canine FcRn at either pH 5.5 or pH 6.0 and pH 7.4 was evaluated. The Biacore method for the pH 5.5 and pH 6.0 condition was the same as described in Example 4, above, with the exception that four concentrations of FcRn (100 nM, 200 nM, 400 nM, 800 nM) were tested which will yield more precise binding kinetics. For the Biacore conditions at pH 7.4, the running buffer used was 10 mM HEPES, 500 mM NaCl, 3 mM EDTA, 0.05% Tween 20, pH 7.4 and the concentration of canine FcRn tested was 200 nM. See FIG. 18 for the Biacore sensorgrams. Neither wild-type Fc nor any of the variants bound to FcRn at pH 7.4 using the conditions described.

The binding affinity data are shown in Tables 15 and 16, below.

TABLE 15

| Variant | pH Tested | ka (1/Ms) | kd (1/s) | KD (M) |
|---|---|---|---|---|
| A426F | 5.5 | 2.53E+05 | 1.32E-01 | 5.22E-07 |
| A426Y | 5.5 | 2.62E+05 | 1.02E-01 | 3.89E-07 |
| A426H | 5.5 | 3.08E+05 | 1.06E-01 | 3.43E-07 |
| Wild-type | 5.5 | 1.68E+05 | 5.27E-01 | 3.15E-06 |
| YTE | 5.5 | 2.50E+05 | 4.60E-02 | 1.84E-07 |

TABLE 16

| Variant | pH Tested | ka (1/Ms) | kd (1/s) | KD (M) |
|---|---|---|---|---|
| T286Y | 6 | 2.56E+05 | 1.62E-01 | 6.32E-07 |
| T286F | 6 | 3.09E+05 | 1.90E-01 | 6.16E-07 |
| T286L | 6 | 3.25E+05 | 2.53E-01 | 7.77E-07 |
| T286W | 6 | 3.45E+05 | 1.95E-01 | 5.65E-07 |
| Y436H | 6 | 3.75E+05 | 1.45E-01 | 3.86E-07 |
| Wild-type | 6 | 2.30E+05 | 4.17E-01 | 1.82E-06 |
| YTE | 6 | 3.14E+05 | 6.59E-02 | 2.10E-07 |

Example 6: Canine Fc Variants Carrying Amino Acid Substitutions at Position 426 of Canine IgGA Fc Two canine Fc variants carrying amino acid modifications at position 426 (by EU numbering) and the wild-type canine IgGA Fc (SEQ ID NO:9) were synthesized using the variable domain described by Gearing D P et al. (2013, *BMC Veterinary Research*, 9:226). The canine IgGA DNAs were synthesized and subcloned into the pcDNA3.4 vector (ThermoFisher) and transfected into ExpiCHO-S cells using the ExpiCHO transfection method (ThermoFisher). Fourteen days after the cells were transfected, the conditioned media was purified using GenScript protein G resin.

Figure 19C:
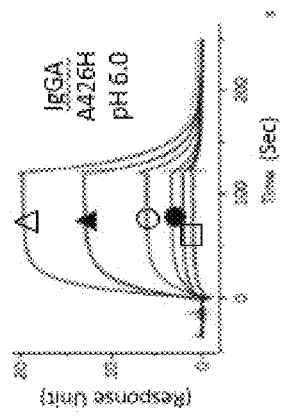
FIGS. 19A-19C show Biacore sensorgrams for IgGA wild-type, IgGA A426Y variant and IgGA A426H variant binding to canine FcRn at pH 6.0. The concentrations of canine FcRn used were 50 nM (white square), 100 nM (black circle), 200 nM (white circle), 400 nM (black triangle) and 800 nM (white triangle). The lighter line in each sensorgram represents the measured data and the darker line represents the fitted curve using a 1:1 interaction model.
Figure 19B:
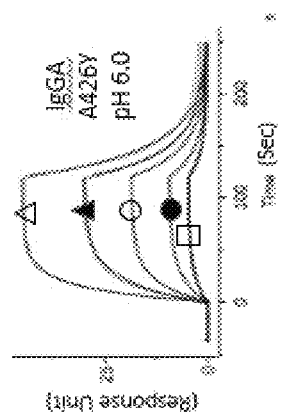
Figure 19A:
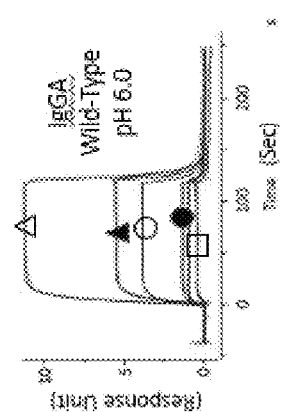
Figure 21A:
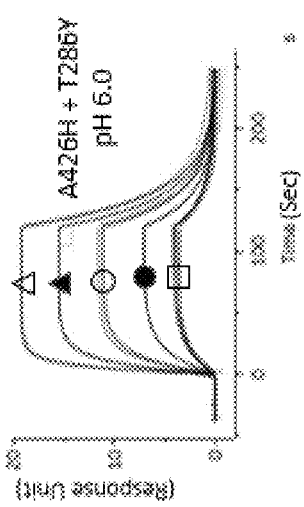
FIGS. 21A-21F show Biacore sensorgrams for single (A426H) and combination variants of canine IgGB Fc binding to canine FcRn at pH 6.0. The concentrations of canine FcRn used for the A426H-N434R IgG variant were 200 nM (white circle), 400 nM (black triangle), 800 nM (white triangle), 1600 nM (black diamond), and 3200 nM (white diamond). The concentrations of canine FcRn for the remaining variants was 50 nM (white square), 100 nM (black circle), 200 nM, (white circle), 400 nM (black triangle) and 800 nM (white triangle). The lighter line in each sensorgram represents the measured data and the darker line represents the fitted curve using a 1:1 interaction model.
Figure 21B:
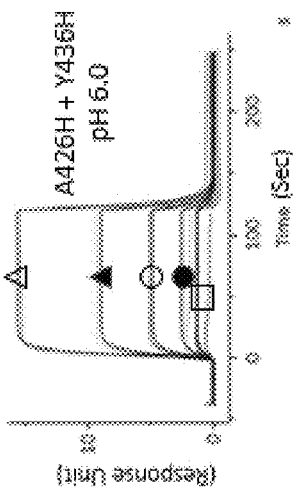
Figure 21C:
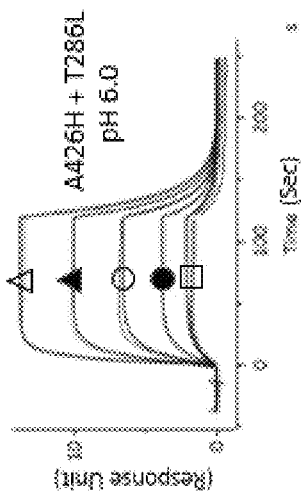
Figure 21D:
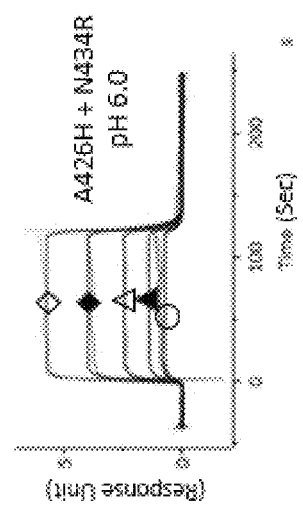
Figure 21E:
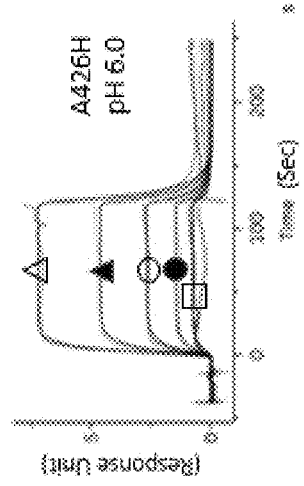
Figure 21F:
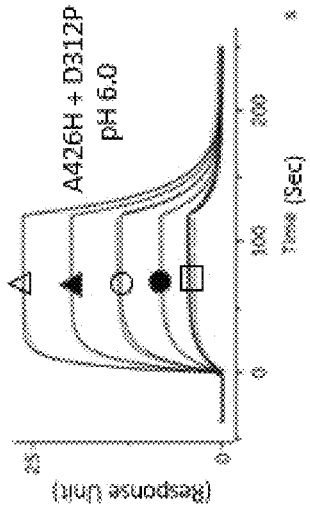
Figures 22A, 22B, 22C, 22D, 22E:
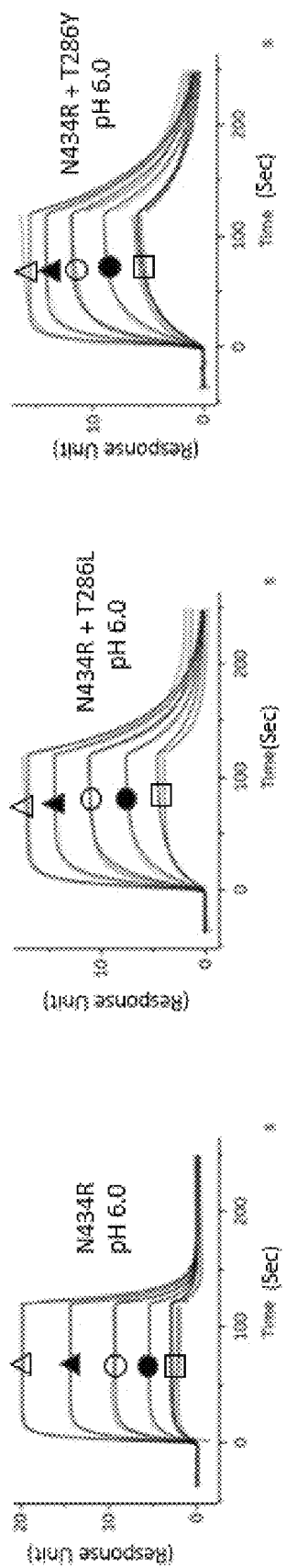
FIGS. 22A-22E show Biacore sensorgrams for single (N434R) and combination variants of canine IgGB Fc binding to canine FcRn at pH 6.0. The concentrations of canine FcRn used for the variants was 50 nM (white square), 100 nM (black circle), 200 nM, (white circle), 400 nM (black triangle) and 800 nM (white triangle). The lighter line in each sensorgram represents the measured data and the darker line represents the fitted curve using a 1:1 interaction model.
Figure 23:
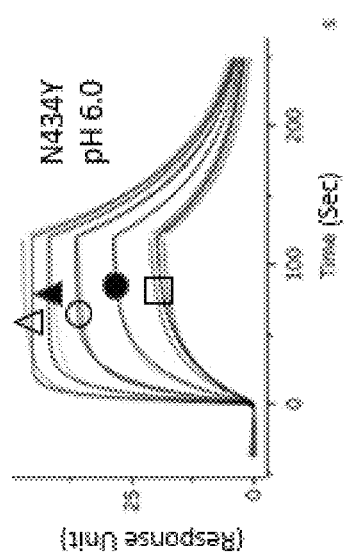
FIG. 23 shows Biacore sensorgrams for the N434Y variant of canine IgGB Fc binding to canine FcRn at pH 6.0. The concentrations of canine FcRn used for the variant was 50 nM (white square), 100 nM (black circle), 200 nM, (white circle), 400 nM (black triangle) and 800 nM (white triangle). The lighter line in each sensorgram represents the measured data and the darker line represents the fitted curve using a 1:1 interaction model.
Figure 24A:
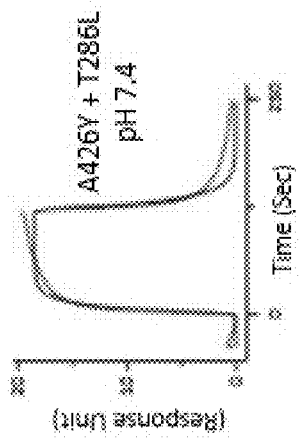
FIGS. 24A-24F show Biacore sensorgrams for wild-type canine IgGB Fc, single (A426Y) and combination variants of IgGB Fc binding to canine FcRn at pH 7.4. The lighter line in each sensorgram represents the measured data and the darker line represents the fitted curve using a 1:1 interaction model.
Figure 24B:
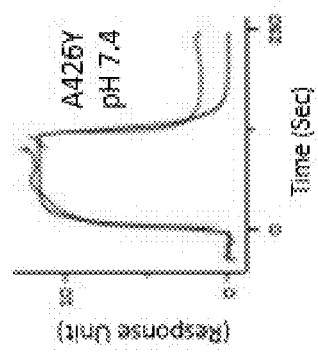
Figure 24C:
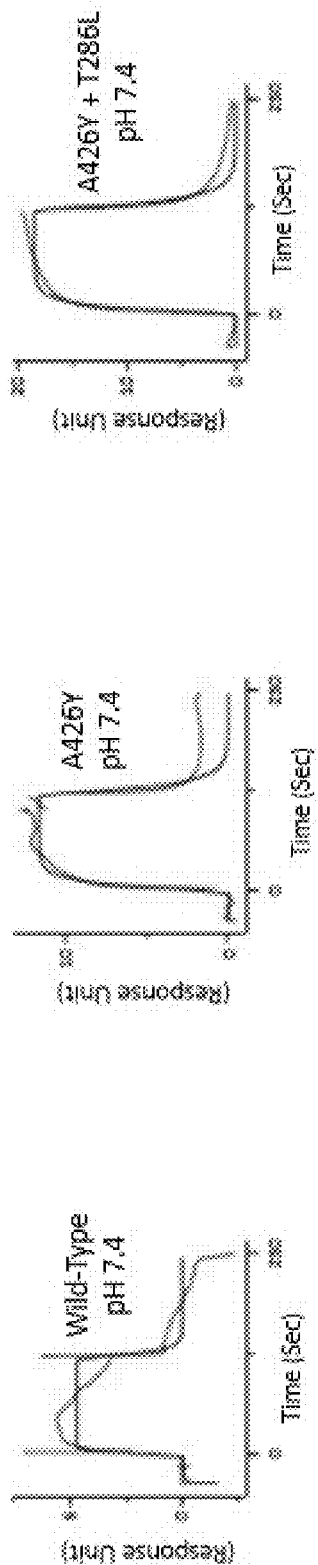
Figure 24D:
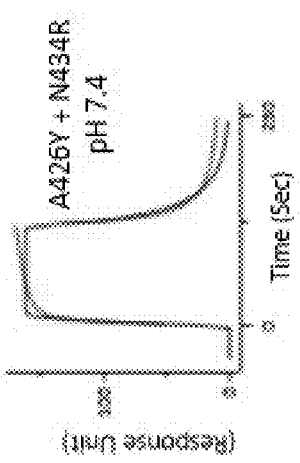
Figure 24E:
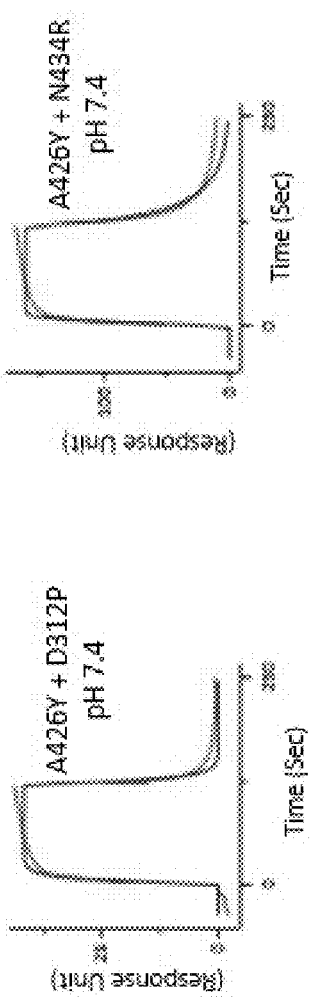
Figure 24F:
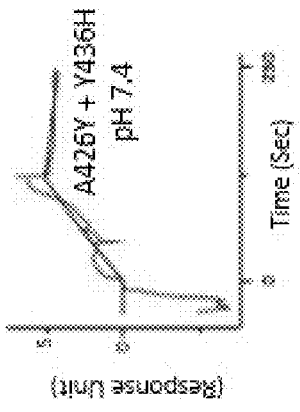
Figure 26C:
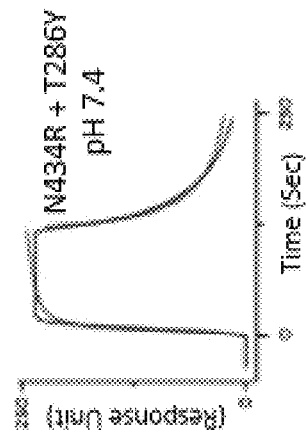
FIGS. 26A-26E show Biacore sensorgrams for single (N434R) and combination variants of IgGB Fc binding to canine FcRn at pH 7.4. The lighter line in each sensorgram represents the measured data and the darker line represents the fitted curve using a 1:1 interaction model.
Figure 26B:
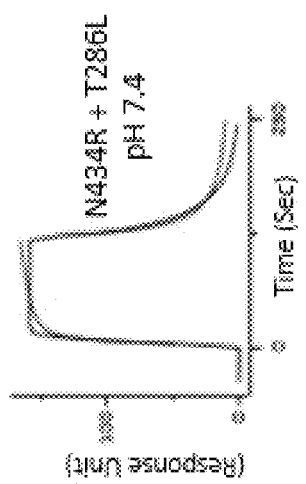
Figure 26E:
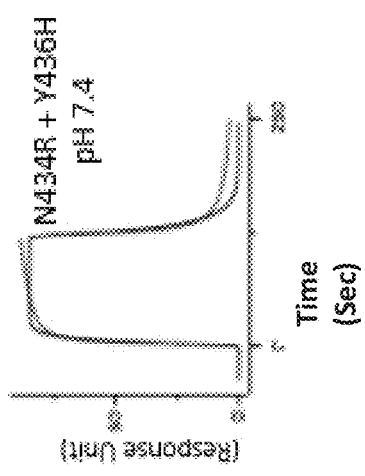
Figure 26A:
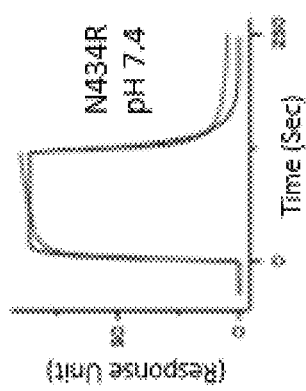
Figure 26D:
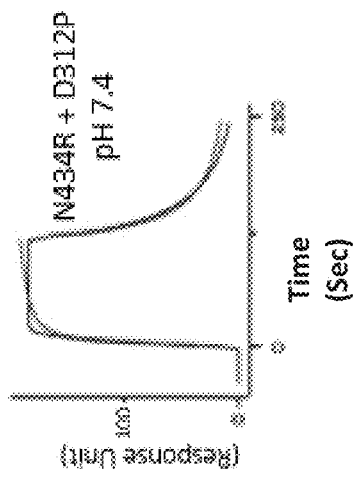
Figure 27:
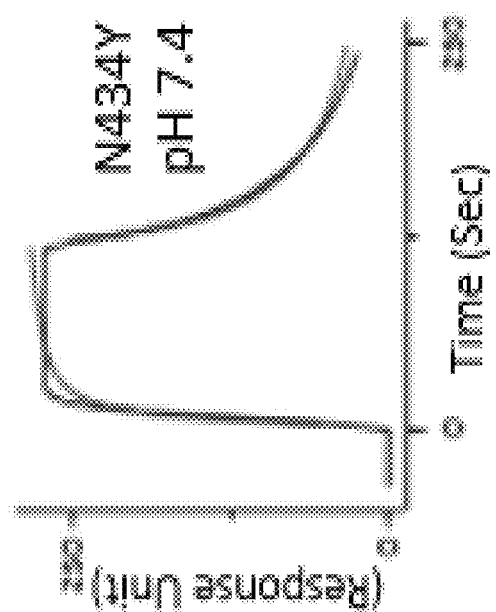
FIG. 27 shows a Biacore sensorgram for the N434Y variant of IgGB Fc binding to canine FcRn at pH 7.4. The lighter line represents the measured data and the darker line represents the fitted curve using a 1:1 interaction model.

For the pH 6.0 binding experiments, the antibodies were directly coupled to a CM5 sensor chip and the canine FcRn was then flowed over in HBS-EP (10 mM HEPES, 500 mM NaCl, 3 mM EDTA, 0.05% Tween 20, pH 6.0). The sensor chip surface of flow cells 1 and 2 were activated by freshly mixed 50 mmol/L N-Hydroxysuccinimide (NETS) and 200 mmol/L 1-ethyl-3-(3-dimethylaminopropyl) carbodiimide hydrochloride (EDC) for 100 s (10 µL/min). Antibodies were diluted in 10 mmol/L NaAC (pH 4.5) and injected into the flow cell 2 to achieve conjugation of about 100 Response Units, whereas flow cell 1 was set as a blank. After the amine coupling reaction, the remaining active coupling sites on chip surface were blocked with 100 s injection of 1 mol/L ethanolamine hydrochloride. The running buffer for the pH 6.0 binding experiment was HBS-EP (10 mM HEPES, 500 mM NaCl, 3 mM EDTA, 0.05% Tween 20, pH 6.0) and it was run at 25° C. Canine FcRn (UniProtKB-E2ROL6 [FcRn] and UniProtKB-E2RN10 [canine beta-2-microglobulin]) was injected for 120 sec and the dissociation was complete with running buffer for 120 sec. The flow rate was 30 µL per minute. The concentrations of canine FcRn flowed over the sensor chip was 50 nM, 100 nM, 200 nM, 400 nM and 800 nM. All of the data were processed using the Biacore 8K evaluation software version 1.1. Flow cell 1 and injection of buffer alone in each cycle was use as the reference for response unit subtraction. Table 17 below provides the kinetic data for the pH 6.0 binding experiments. Previously it has been demonstrated that the amine-coupling of IgGs to a Biacore CM5 biosensor chip reduces the affinity to FcRn by 2-3 fold compared to affinity determined by solution-based methods or directly coupling to a Biacore C1 chip (Abdiche et al., 2015. mAbs, 7:331). Therefore the true affinity of these IgGs to FcRn at pH 6.0 is likely at least 2-fold higher. This method is however valid to compare the relative FcRn binding affinities of the different IgG Fc variants. The Biacore sensorgrams are shown in FIG. 19.

TABLE 17

| Antibody | ka (1/Ms) | kd(1/s) | KD (M) |
|---|---|---|---|
| IgGA Wild-Type | 3.14E+04 | 1.87E-01 | 5.97E-06 |
| IgGA A426Y | 4.89E+04 | 3.75E-02 | 7.67E-07 |
| IgGA A426H | 4.14E+04 | 5.91E-02 | 1.43E-06 |

Example 7: Screening for Canine IgGB Fc Variants with Increased FcRn Binding Compared to Wild-Type Canine IgGB Fc Canine Fc variants carrying single amino acid substitutions or a combination of amino acid substitutions were synthesized into the canine IgGB (SEQ ID NO:10) format using the variable domain described by Gearing D P et al. (2013, *BMC Veterinary Research*, 9:226). The canine IgGB DNAs were synthesized and subcloned into the pcDNA3.4 vector (ThermoFisher) and transfected into ExpiCHO-S cells using the ExpiCHO transfection method (ThermoFisher). Fourteen days after the cells were transfected, the conditioned media was purified using Monofinity A resin (GenScript). The binding of the antibodies to canine FcRn was measured at both pH 6.0 and pH 7.4 conditions using the Biacore 8K.

For the pH 6.0 binding conditions, the sensor chip surface of flow cells 1 and 2 were activated by freshly mixed 50 mmol/L N-Hydroxysuccinimide (NHS) and 200 mmol/L 1-ethyl-3-(3-dimethylaminopropyl) carbodiimide hydrochloride (EDC) for 100 s (10 µL/min). Antibodies were diluted in 10 mmol/L NaAC (pH 4.5) and injected into the flow cell 2 to achieve conjugation of about 100 Response Units, whereas flow cell 1 was set as a blank. After the amine coupling reaction, the remaining active coupling sites on chip surface were blocked with 100 s injection of 1 mol/L ethanolamine hydrochloride. The running buffer for the pH 6.0 binding experiment was HBS-EP (10 mM HEPES, 500 mM NaCl, 3 mM EDTA, 0.05% Tween 20, pH 6.0) and it was run at 25° C. Canine FcRn (UniProtKB-E2ROL6 [FcRn] and UniProtKB-E2RN10 [canine beta-2-microglobulin]) was injected for 120 sec and the dissociation was complete with running buffer for 120 sec. The flow rate was 30 µl per minute. The concentrations of canine FcRn flowed over the sensor chip were 200 nM, 400 nM, 800 nM, 1600 nM, and 3200 nM for the wild-type IgG and the A426H-N434R IgG variants. The concentrations of canine FcRn flowed over for the remaining variants was 50 nM, 100 nM, 200 nM, 400 nM and 800 nM. All of the data were processed using the Biacore 8K evaluation software version 1.1.

Flow cell 1 and injection of buffer alone in each cycle was use as the reference for response unit subtraction. Table 18 below sets out the kinetic data for the pH 6.0 binding experiments. Previously it has been demonstrated that the amine-coupling of IgGs to a Biacore CM5 biosensor chip reduces the affinity to FcRn by 2-3 fold compared to affinity determined by solution-based methods or directly coupling to a Biacore C1 chip (Abdiche et al., 2015. mAbs, 7:331). Therefore the true affinity of these IgGs to FcRn at pH 6.0 is likely at least 2-fold higher. This method is however valid to compare the relative FcRn binding affinities of the different IgG Fc variants. The Biacore sensorgrams are shown in FIGS. 20-23.

TABLE 18

| | Binding at pH 6.0 | | |
|---|---|---|---|
| Antibody | ka (1/Ms) | kd (1/s) | KD (M) |
| Wild-Type | 1.14E+05 | 3.85E−01 | 3.37E−06 |
| A426Y | 1.19E+05 | 1.34E−01 | 1.13E−06 |
| A426Y + T286L | 1.71E+05 | 5.59E−02 | 3.27E−07 |
| A426Y + D312P | 1.37E+05 | 5.77E−02 | 4.21E−07 |
| A426Y + N434R | 2.06E+05 | 5.91E−02 | 2.88E−07 |
| A426Y + Y436H | 1.53E+05 | 7.77E−02 | 5.07E−07 |
| A426H | 1.19E+05 | 1.24E−01 | 1.04E−06 |
| A426H + T286L | 1.49E+05 | 6.90E−02 | 4.64E−07 |
| A426H + T286Y | 1.60E+05 | 4.09E−02 | 2.55E−07 |
| A426H + D312P | 1.45E+05 | 5.47E−02 | 3.76E−07 |
| A426H + N434R | 1.07E+05 | 2.64E−01 | 2.48E−06 |
| A426H + Y436H | 8.87E+04 | 2.02E−01 | 2.27E−06 |
| N434R | 2.16E+05 | 1.07E−01 | 4.97E−07 |
| N434R + T286L | 1.80E+05 | 3.10E−02 | 1.73E−07 |
| N434R + T286Y | 2.36E+05 | 2.21E−02 | 9.37E−08 |
| N434R + D312P | 2.44E+05 | 4.80E−02 | 1.97E−07 |
| N434R + Y436H | 2.62E+05 | 8.38E−02 | 3.20E−07 |
| N434Y | 2.55E+05 | 1.81E−02 | 7.08E−08 |

For the pH 7.4 binding conditions, the sensor chip surface of flow cells 1 and 2 were activated by freshly mixed 50 mmol/L N-Hydroxysuccinimide (NHS) and 200 mmol/L 1-ethyl-3-(3-dimethylaminopropyl) carbodiimide hydrochloride (EDC) for 420 s (10 µL/min). Afterwards, canine FcRn diluted in 10 mmol/L NaAC (pH 4.5) was injected into the flow cell 2 to achieve conjugation of 2000 response units, while flow cell 1 was set as blank. After the amine coupling reaction, the remaining active coupling sites on chip surface were blocked with 420 s injection of 1 mol/L ethanolamine hydrochloride. The running buffer for the pH 7.4 binding experiment was HBS-EP (10 mM HEPES, 500 mM NaCl, 3 mM EDTA, 0.05% Tween 20, pH 7.4) and it was run at 25° C.] The different antibodies were injected at 400 nM for 120 sec and the dissociation was complete with running buffer for 120 sec. The flow rate was 30 µl per minute. Table 19 below sets out the kinetic data for the pH 7.4 binding experiments. The Biacore sensorgrams are shown in FIGS. 24-27.

TABLE 19

| | Binding at pH 7.4-High Density Canine FcRn | | |
|---|---|---|---|
| Antibody | ka (1/Ms) | kd (1/s) | KD (M) |
| Wild-Type | — | — | No binding |
| A426Y | — | — | Low binding |
| A426Y + T286L | 8.23E+04 | 9.20E−02 | 1.12E−06 |
| A426Y + D312P | 5.89E+04 | 1.71E−01 | 2.90E−06 |
| A426Y + N434R | 1.35E+09 | 1.74E+02 | 1.29E−07 |
| A426Y + Y436H | — | — | No binding |
| A426H | — | — | No binding |
| A426H + T286L | 8.12E+04 | 1.30E−01 | 1.60E−06 |
| A426H + T286Y | 1.36E+05 | 1.28E−01 | 9.40E−07 |
| A426H + D312P | 2.17E+05 | 1.56E−01 | 7.22E−07 |
| A426H + N434R | — | — | No binding |
| A426H + Y436H | — | — | No binding |
| N434R | 8.25E+08 | 1.93E+02 | 2.34E−07 |
| N434R + T286L | 2.22E+09 | 2.98E+02 | 1.34E−07 |
| N434R + T286Y | 3.40E+08 | 2.76E+01 | 8.12E−08 |
| N434R + D312P | 4.95E+08 | 5.14E+01 | 1.04E−07 |
| N434R + Y436H | 6.66E+05 | 2.55E−01 | 3.82E−07 |
| N434Y | 2.87E+06 | 2.30E−01 | 8.02E−08 |

The affinity of the interaction of canine IgG Fc with canine FcRn at pH 7.4 is very weak and difficult to measure by SPR using most methods. In order to compare the pH 7.4 affinities of the various canine Fc variants to canine FcRn, the sensor chip was coated with a high concentration of canine FcRn and the variant IgG Fc were flowed over the chip to measure the interaction. In this format there are avidity effects so the binding affinities measured are not accurate measurements of the individual canine IgG Fc variant-canine FcRn interaction but can be used for comparing the relative binding of variant IgGs at pH 7.4. They should not be used to make direct comparisons to the binding affinities at pH 6.0.

Example 8: In Vivo Screening for Canine IgGB Fc Variants with Increased FcRn Binding Compared to Wild-Type Canine IgGB Fc A pharmacokinetic (PK) study was undertaken with sixteen male and female beagles. Canine IgGB Fc variants carrying a single amino acid substitution or a combination of amino acid substitutions were prepared by incorporating the amino acid substitution(s) into canine IgGB (SEQ ID NO:10) using the anti-NGF variable domain described by Gearing D P et al. (2013, *BMC Veterinary Research*, 9:226; the content of which is incorporated herein by reference in its entirety). The animals were randomized into eight groups with a male and female in each group. The average age of the beagles was >6 months and their weight was from 8-10 kg. Each animal was administered with a single intravenous dose of 2 mg/kg of antibody. Approximately 1.5 ml of whole blood was collected at the following time points: 0 (pre-dose), 4 hours, and 1, 2, 4, 6, 101418, 22, 30, 34, 38, 42 days post injection. Serum was separated from the whole blood and assayed for the presence of the antibody variant by an ELISA that is specific for anti-NGF antibodies.

Figure 29:
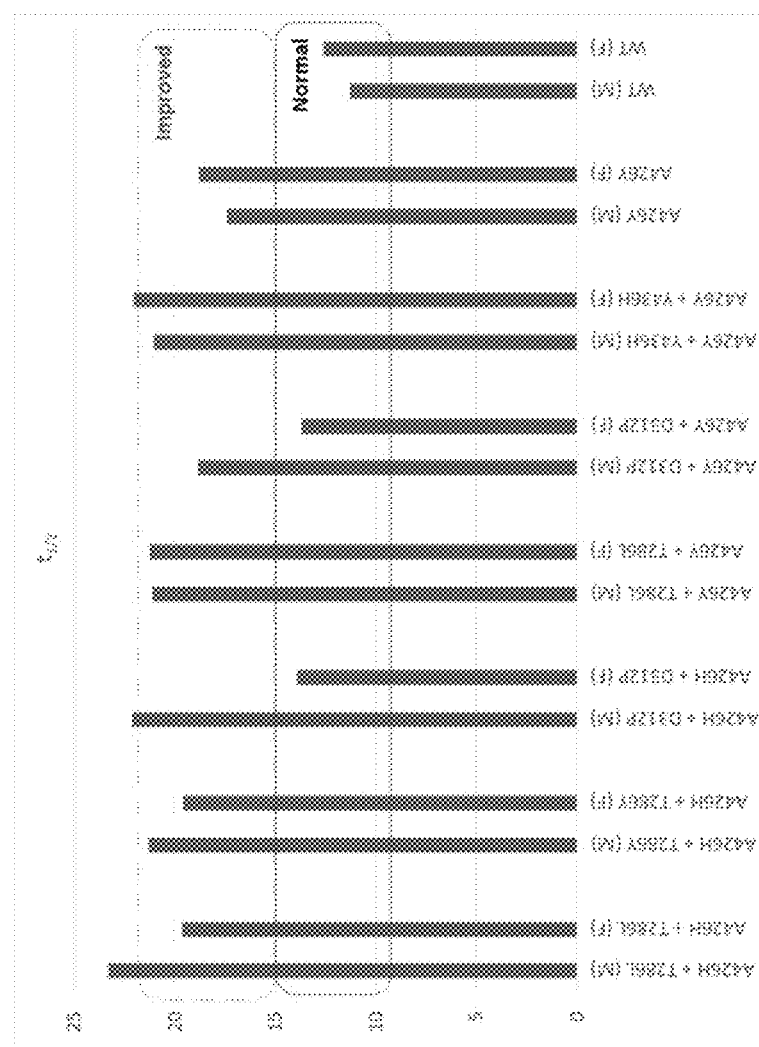
FIG. 29 shows the terminal half-life (Days; Y-axis) of canine anti-nerve growth factor (NGF) IgGB Fc variants carrying a single amino acid substitution or a combination of amino acid substitutions following intravenous administration into male (M) and female (F) beagles. The animals were randomized into eight groups with a male and female in each group. Each animal was administered with a single intravenous dose of 2 mg/kg of antibody and approximately 1.5 ml of whole blood was collected at the following time points: 0 (pre-dose), 4 hours, and 1, 2, 4, 6, 101418, 22, 30, 34, 38, 42 days post injection. Serum was separated from the whole blood and assayed for the presence of the anti-NGF antibody by ELISA. A non-compartmental PK analysis (NCA) was performed of each individual serum antibody measurement using *PKSolver* (Yong Zhang et al., *Comput. Methods Programs Biomed.;* 2010 September; 99(3):306-14. doi: 10.1016/j.cmpb.2010.01.007).
Figure 30A:
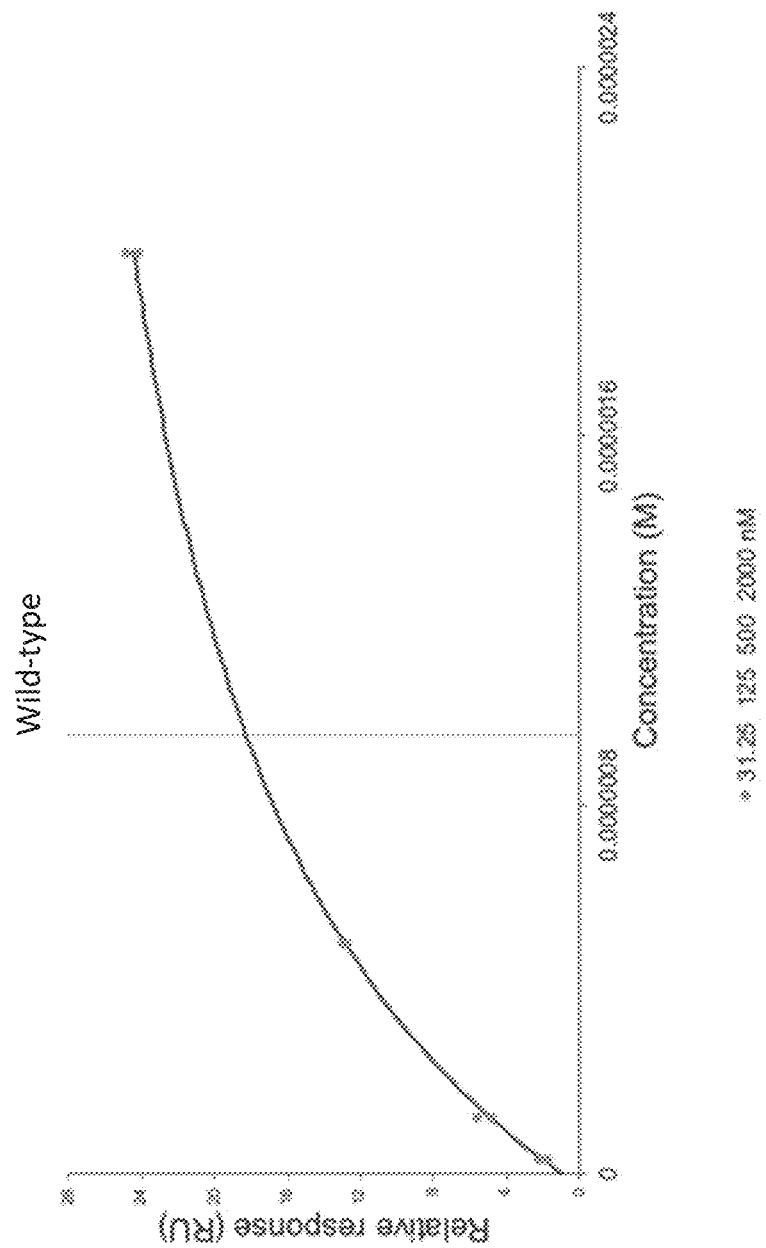
Figure 30B:
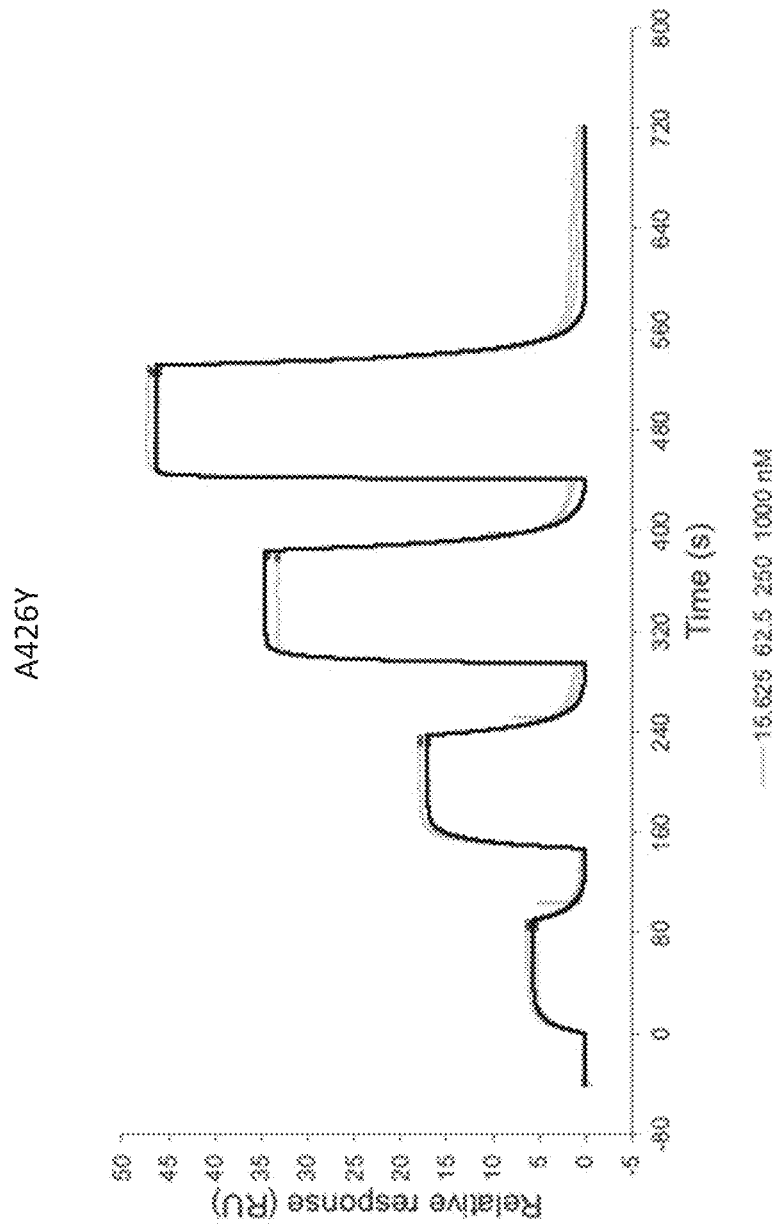
Figure 30C:
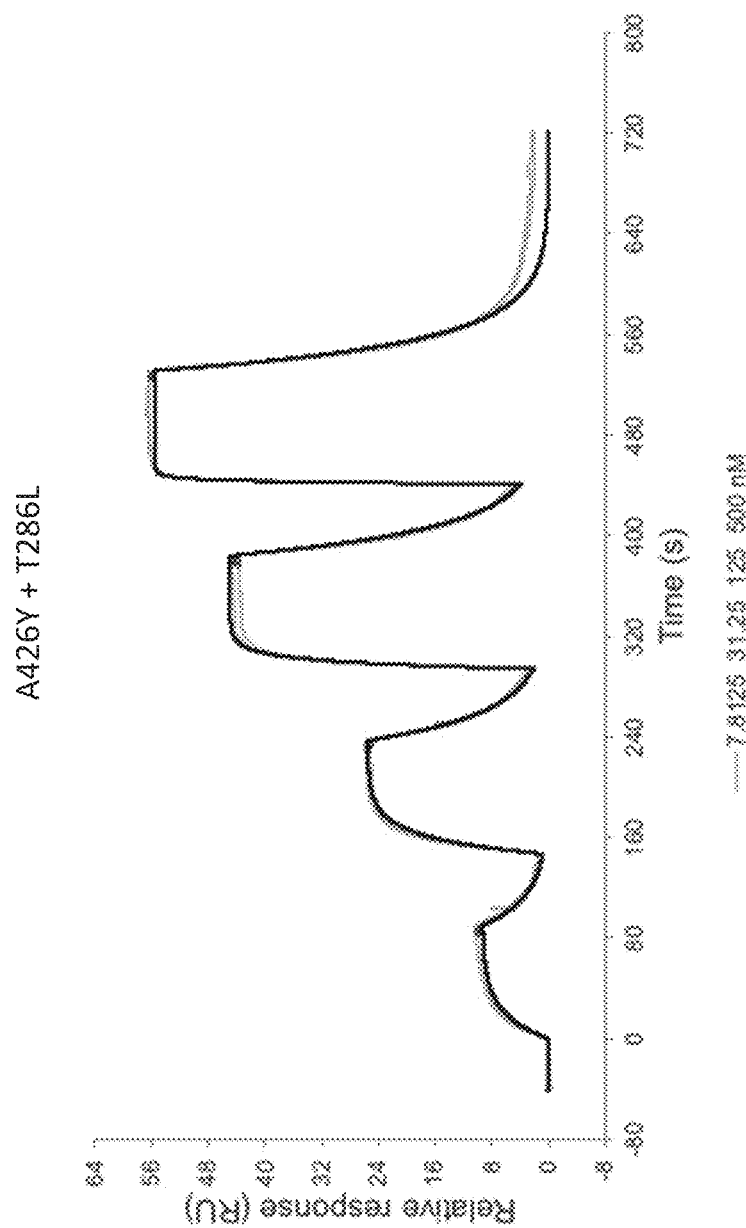
Figure 30D:
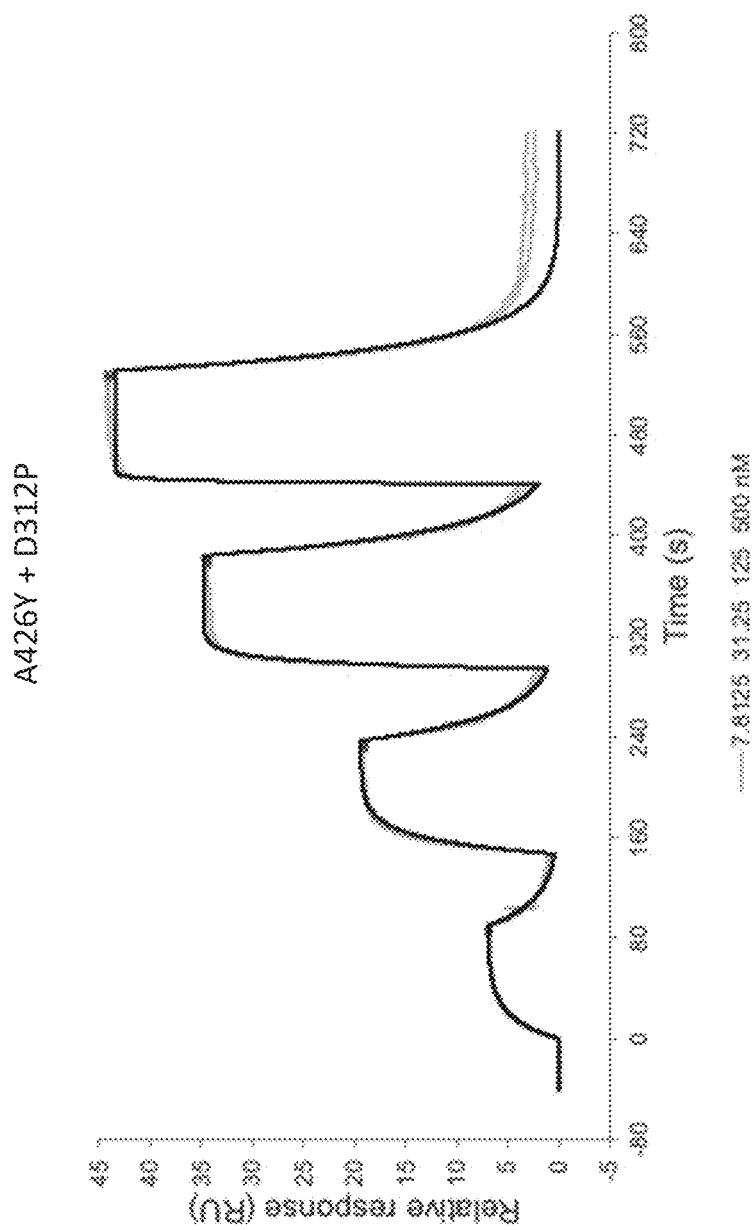
Figure 30F:
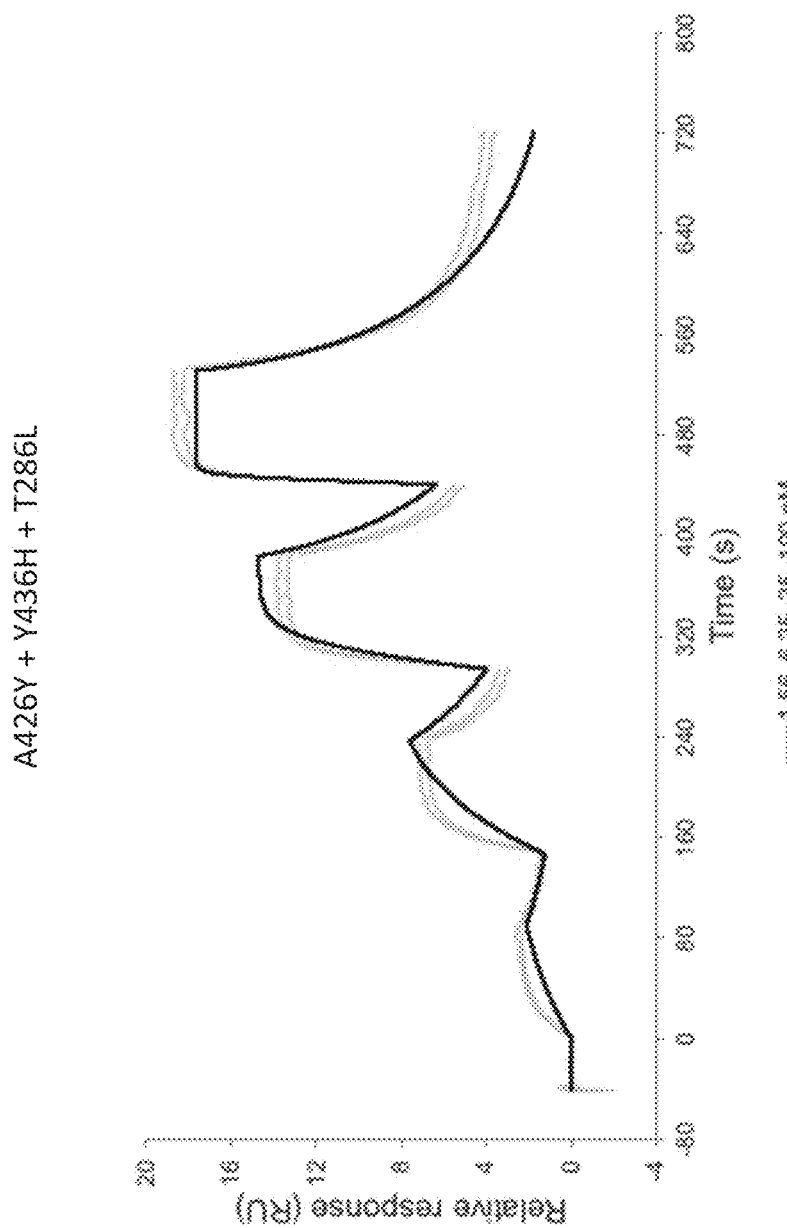
Figure 30G:
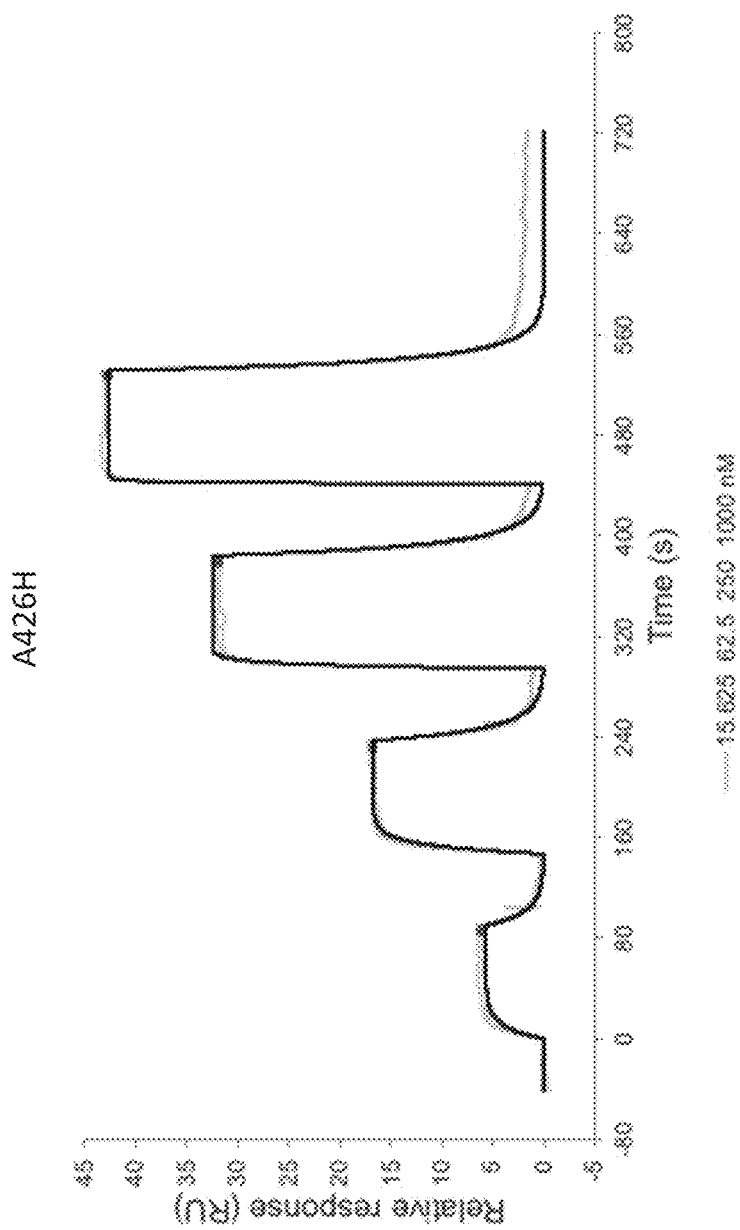
Figure 30I:
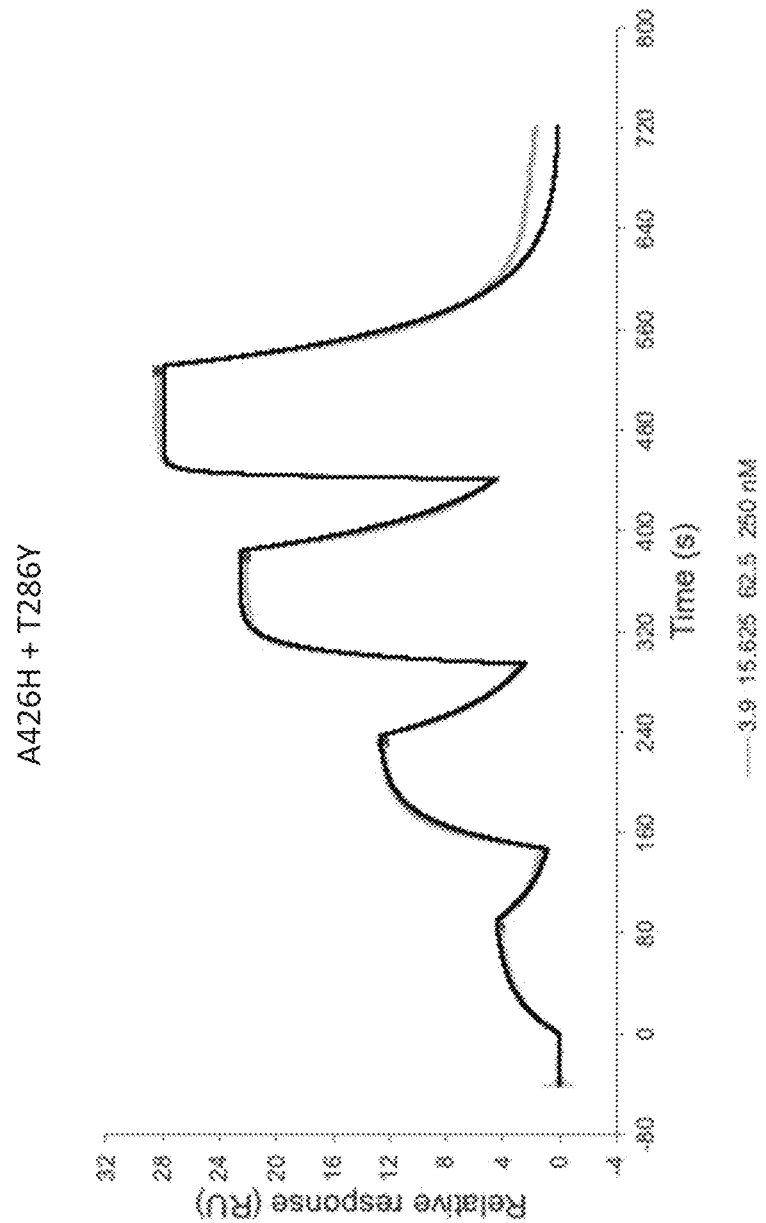
Figure 30J:
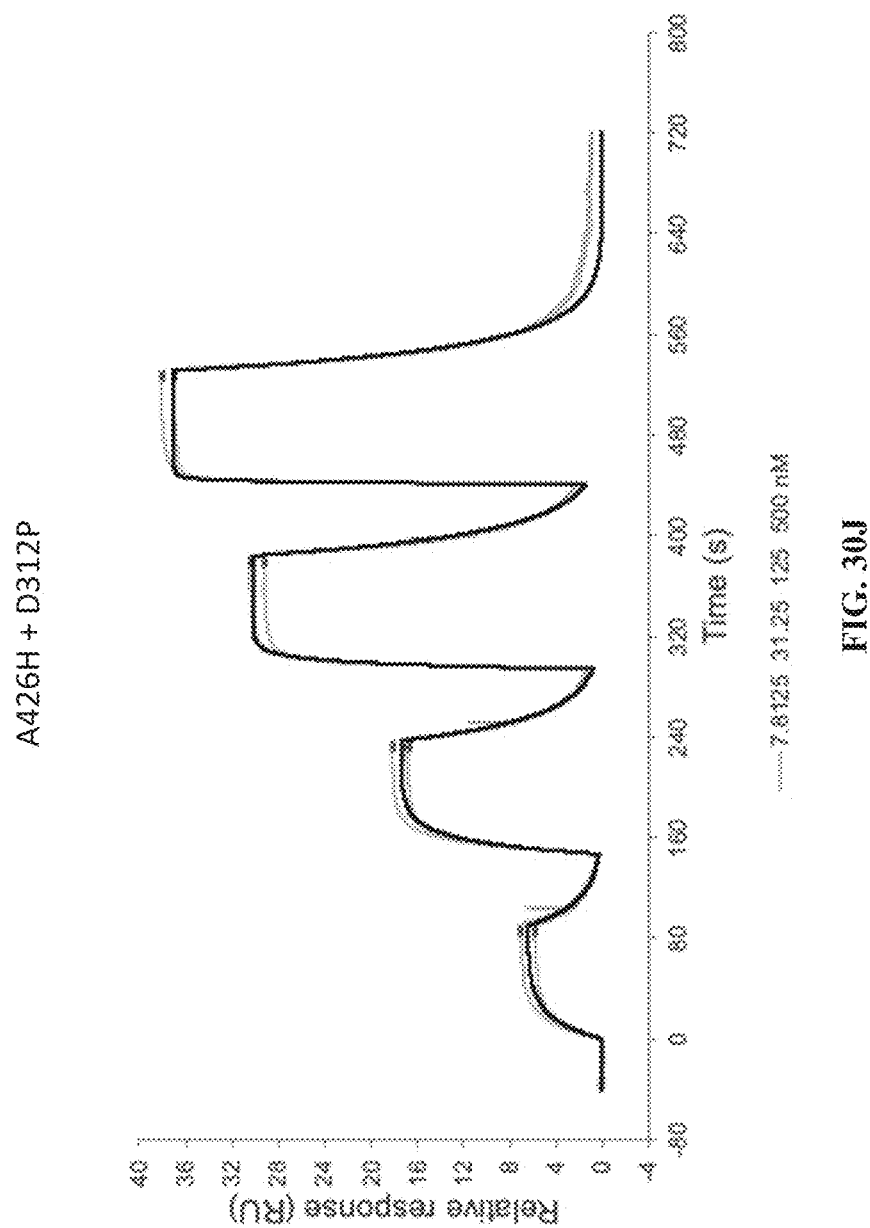
Figure 30K:
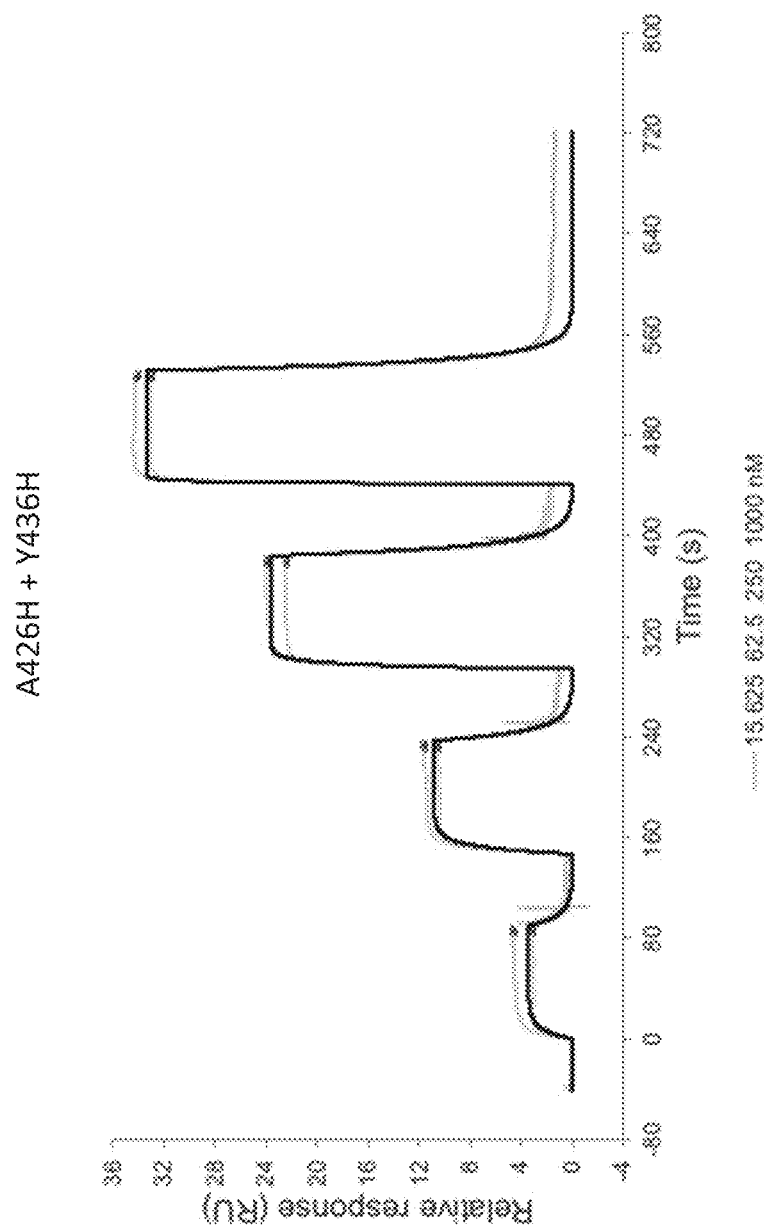

A non-compartmental PK analysis (NCA) was performed of each individual serum antibody measurement using a well-documented Excel plug-in software tool for pharmacokinetic analysis ("*PKSolver: An add-in program for pharmacokinetic and pharmacodynamic data analysis in Microsoft Excel*", Yong Zhang et al., *Comput. Methods Programs Biomed.*; 2010 September; 99(3):306-14. doi: 10.1016/j.cmpb.2010.01.007; the content of which is incorporated herein by reference in its entirety). PKSolver provides many options for the determination of PK parameters. NCA was identified as the method of choice for the simplicity of use, model-independence and the increased analyst to analyst consistency. For the specific analysis, the NCA IV Bolus in PKSolver was used to determine the terminal half-life (T½). Following an initial set of dose-finding experiments, measurements well above LLOQ could be measured as far out as 42 days after intravenous administration. Accordingly, terminal half-life was estimated on at least the last four weeks of antibody measurement to enable to robust estimation of slope. No data points were discarded or eliminated in any of the experiments. As shown in FIG. 29, the combination of amino acid substitutions in the IgG Fc region markedly improved the terminal half-life of the anti-NGF IgGB antibodies in canine in vivo, when compared to anti-NGF IgGB antibodies carrying (i) a wild-type canine IgGB Fc region or (ii) a canine IgGB Fc variant with only a single amino acid substitution.

Example 9: Binding Kinetics of Canine IgGB Variants to Canine FcRn Using C1 Biosensors Several canine IgGB variants (A426Y, A426Y+T286L, A426Y+D312P, A426Y+Y436H, A426Y+T286L+Y436H, A426H, A426H+T286L, A426H+T286Y, A426H+D312P, A426H+Y436H, and wild-type) were evaluated for binding kinetics to canine FcRn (UniProtKB-E2ROL6 [canine large subunit FcRn] and UniProtKB-E2RN10 [canine beta-2-microglobulin]) at pH 5.9. EU numbering was used to identify the positions (FIG. 28). In this study, the canine Fc variants carrying single amino acid substitutions or a combination of amino acid substitutions were synthesized into the canine IgGB (GENBANK accession number AAL35302.1) format using the variable domain described by Gearing D P et al. (2013, *BMC Veterinary Research*, 9:226). The synthesized canine IgGB DNAs were subcloned into a mammalian expression vector and transiently transfected into CHO cells. The conditioned media were purified using protein A chromatography.

For the canine FcRn binding experiments, all assays were completed on a Biacore 8K+ system at 25° C. In the above examples (e.g. Examples 6 and 7), we measured the affinity of IgG variants to canine FcRn by amine-coupling of IgGs to a Biacore CM5 biosensor chip which has been demonstrated by Abdiche et al., 2015 (mAbs, 7:331) to underestimate the affinity of Fc variants to FcRn compared to when using a Series S C1 biosensor. In this set of experiments, to obtain a more accurate measurement of FcRn affinity, all antibodies were immobilized using standard amine coupling reagents to Series S C1 sensor chips. A mixture of 200 mmol/L 1-ethyl-3-(3-dimethylaminopropyl) carbodiimide hydrochloride (EDC) and 50 mmol/L N-Hydroxysuccinimide (NETS) was injected for 420 seconds to activate the surface. Then, antibodies were injected at a concentration of 0.5 to 2 µg/ml in 10 mM sodium acetate pH 5.0 for 120 seconds. Finally, 1M ethanolamine was injected for 420 seconds. The running buffer was 1×PBS-P+(Cytiva, Cat #28995084) adjusted to pH 5.9.

To evaluate the binding affinity of the canine IgGB variants to canine FcRn at pH 5.9, a range of concentrations from 1.56-2000 nM of canine FcRn were chosen and injected in single cycle mode. The concentrations of canine FcRn tested for each variant are shown below in Table 20.

TABLE 20

Concentrations of canine FcRn used for each IgGB variant

| Variant | Concentrations of FcRn [nM] |
|---|---|
| Wild-type | 31.25, 125, 500, 2000 |
| A426Y | 15.625, 62.5, 250, 1000 |
| A426Y + T286L | 7.8125, 31.25, 125, 500 |
| A426Y + D312P | 7.8125, 31.25, 125, 500 |
| A426Y + Y436H | 7.8125, 31.25, 125, 500 |
| A426Y + T286L + Y436H | 1.56, 6.25, 25, 100 |
| A426H | 15.625, 62.5, 250, 1000 |
| A426H + T286L | 3.9, 15.625, 62.5, 250 |
| A426H + T286Y | 3.9, 15.625, 62.5, 250 |
| A426H + D312P | 7.8125, 31.25, 125, 500 |
| A426H + Y436H | 15.625, 62.5, 250, 1000 |

Four concentrations per antibody were injected at 5 µl/min for 90 seconds, followed by 180 seconds dissociation. Each concentration series was injected three times in this format, with at least three buffer-only cycles for proper reference subtraction. The surface was regenerated with two injections of 1×PBS-P+, pH 7.4 for 30 seconds, followed by a 60 second wait command. Three startup cycles were included to stabilize the surface prior to analysis.

Data were evaluated using Insight Evaluation Software by fitting to a 1:1 kinetic interaction model, or by fitting to steady state affinity. Quality metrics including the U-value and T-value were used to select the accepted parameters. A U-value of less than 15 was considered acceptable for kinetic rate constants, while a T-value of greater than 100 was considered acceptable for kinetic rate constants. Where these values are outside the range, the steady state affinity parameters are considered acceptable.

The kinetic data for the ten variants are shown below in Table 21 and the sensorgrams are shown in FIGS. 30A-30K.

TABLE 21

Canine IgGB variants and canine FcRn binding kinetics

| Variant | ka | kd | KD | Method for fitting data |
|---|---|---|---|---|
| Wild-type | | | 9.51E−07 | Steady state affinity |
| A426Y | 8.78E+05 | 1.13E−01 | 1.29E−07 | 1:1 kinetic interaction model |
| A426Y + T286L | 1.03E+06 | 4.36E−02 | 4.23E−08 | 1:1 kinetic interaction model |
| A426Y + D312P | 1.10E+06 | 4.97E−02 | 4.51E−08 | 1:1 kinetic interaction model |
| A426Y + Y436H | 1.06E+06 | 6.08E−02 | 5.77E−08 | 1:1 kinetic interaction model |
| A426Y + T286L + Y436H | 5.67E+06 | 4.12E−02 | 7.26E−09 | 1:1 kinetic interaction model |

TABLE 21-continued

Canine IgGB variants and canine FcRn binding kinetics

| Variant | ka | kd | KD | Method for fitting data |
|---|---|---|---|---|
| A426H | 1.24E+06 | 1.42E-01 | 1.15E-07 | 1:1 kinetic interaction model |
| A426H + T286L | 1.16E+06 | 4.17E-02 | 3.58E-08 | 1:1 kinetic interaction model |
| A426H + T286Y | 1.34E+06 | 2.86E-02 | 2.13E-08 | 1:1 kinetic interaction model |
| A426H + D312P | 1.31E+06 | 5.32E-02 | 4.05E-08 | 1:1 kinetic interaction model |
| A426H + Y436H | 8.08E+05 | 1.30E-01 | 1.61E-07 | 1:1 kinetic interaction model |

Example 10: Pharmacokinetic Studies of Canine IgGB Variants with Increased FcRn Binding and Wild-Type Canine IgGB Three pharmacokinetic (PK) studies were completed with male and female beagles. Canine Fc variants carrying single amino acid substitutions or a combination of amino acid substitutions were synthesized into the canine IgGB (SEQ ID NO:10) format using the anti-NGF variable domain described by Gearing D P et al. (2013, *BMC Veterinary Research*, 9:226). For each study the animals were randomized so each group contains an equal number of males and females. The IgGB variants evaluated in each study and the number of males (M) and females (F) in each group are shown below (Table 22).

TABLE 22

Description of IgGB variants tested in each PK study

| Variant | Study 1 | Study 2 | Study 3 |
|---|---|---|---|
| Wild-type | 1M + 1F | 1M + 1F | 1M + 1 F |
| A426Y | 1M + 1F | 1M + 1F | 1M + 1 F |
| A426Y + Y436H | | 1M + 1F | 1M + 1F |
| A426Y + Y436H + T286L | | | 2M + 2F |
| N434R | 1M + 1F | | |
| N434Y | 1M + 1F | | |
| YTE (L252Y + A254T + T256E) | 1M + 1F | 1M + 1F | |

The average age of the dogs was >6 months and the weight was between 8-10 kg. Each animal was injected with a single intravenous dose of 1 mg/kg (Study 1) or 2 mg/kg (Study 2 and 3) of antibody. Approximately 1.5 ml of whole blood was collected at the following time points: 0 (pre-dose), 4 hours, and 1, 2, 4, 6, 101418, 22, 30, 34, 38, 42 days post injection. Serum was extracted from the blood and assayed for the antibody variant by an ELISA specific for NGF antibodies.

Figure 31:
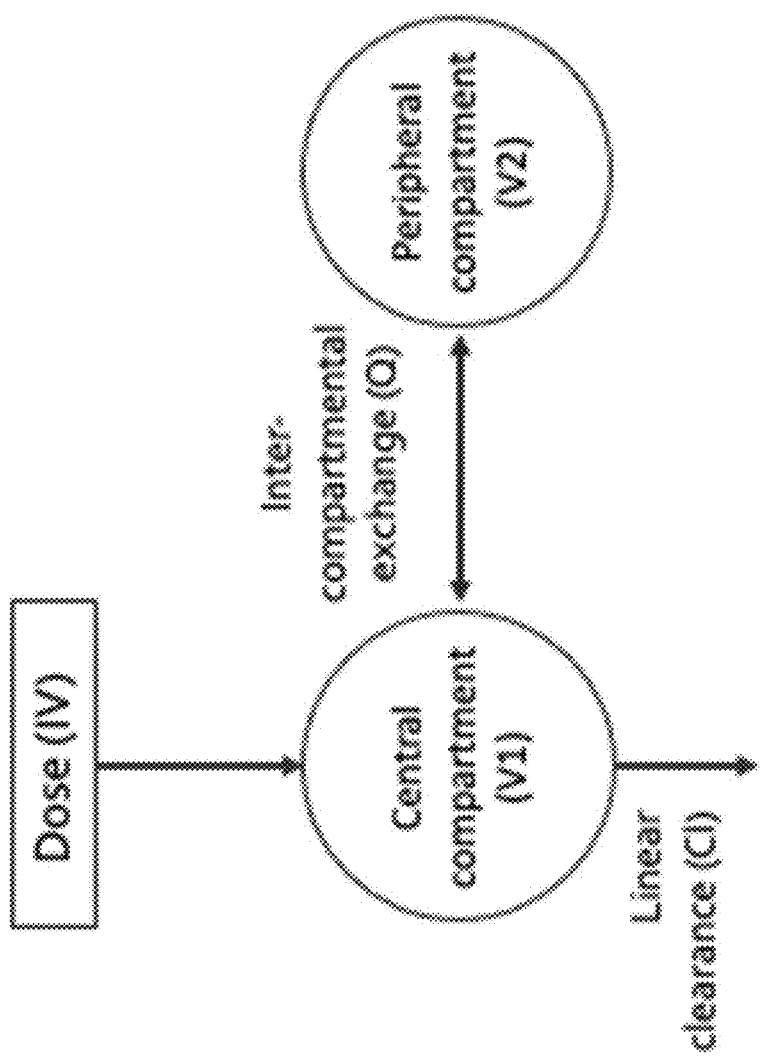
FIG. 31 is a schematic illustration of a two-compartmental pharmacokinetic (PK) model with linear clearance using non-linear mixed effects modelling.

Serum concentrations were described with a two-compartmental pharmacokinetic (PK) model with linear clearance using non-linear mixed effects modelling (FIG. 31). Population PK parameters were estimated using the stochastic approximation of expectation-maximization (SAEM) algorithm implemented in Monolix Suite 2019R1 (Monolix version 2019R1. Antony, France: Lixoft SAS, 2019). Individual parameters were modeled as random variables with log-normal distributions. Population parameters were estimated from the pooled data that included all variants and studies. Study was a categorical covariate on clearance. mAb variants were discriminated by using a categorical covariate on clearance, central and peripheral volume of distribution. The categorial study and variant covariates were described by:

$$\varphi_i = \varphi_{pop} e^{(\beta \Omega_i)} e^{\eta}$$

where $\Omega_i=1$ if the individual covariate was in the category and $\Omega_i=0$ otherwise. The wild type IgGB variant was used as a reference.

The terminal half-life for wild-type, A426Y and A426Y+ Y436H variants observed in Study 2 are shown in FIG. 29.

Data from all three studies was used to generate the estimated PK parameters for each of the variants (Table 23).

TABLE 23

PK parameter estimates for a dog with 10 kg body weight

| Variant | Cl (mL/day) | V1 (mL) | Q (mL/day) | V2 (mL) | α-$T_{1/2}$ (hour) | β-$T_{1/2}$ (day) |
|---|---|---|---|---|---|---|
| Wild-type | 46.83 | 383.5 | 281.7 | 303.8 | 9.683 | 10.52 |
| A426Y | 26.48 | 415.5 | 281.7 | 234.2 | 8.736 | 17.22 |
| A426Y + Y436H | 23.96 | 468.4 | 281.7 | 246.2 | 9.434 | 20.88 |
| A426Y + Y436H + T286L | 23.02 | 517.7 | 281.7 | 231.9 | 9.383 | 22.75 |
| N434R | 35.75 | 454.6 | 281.7 | 188.0 | 7.767 | 12.6 |
| N434Y | 50.73 | 487.5 | 281.7 | 251.2 | 9.583 | 10.31 |
| YTE | 27.29 | 468.4 | 281.7 | 222.8 | 8.826 | 17.74 |

Figures 32A, 32B:
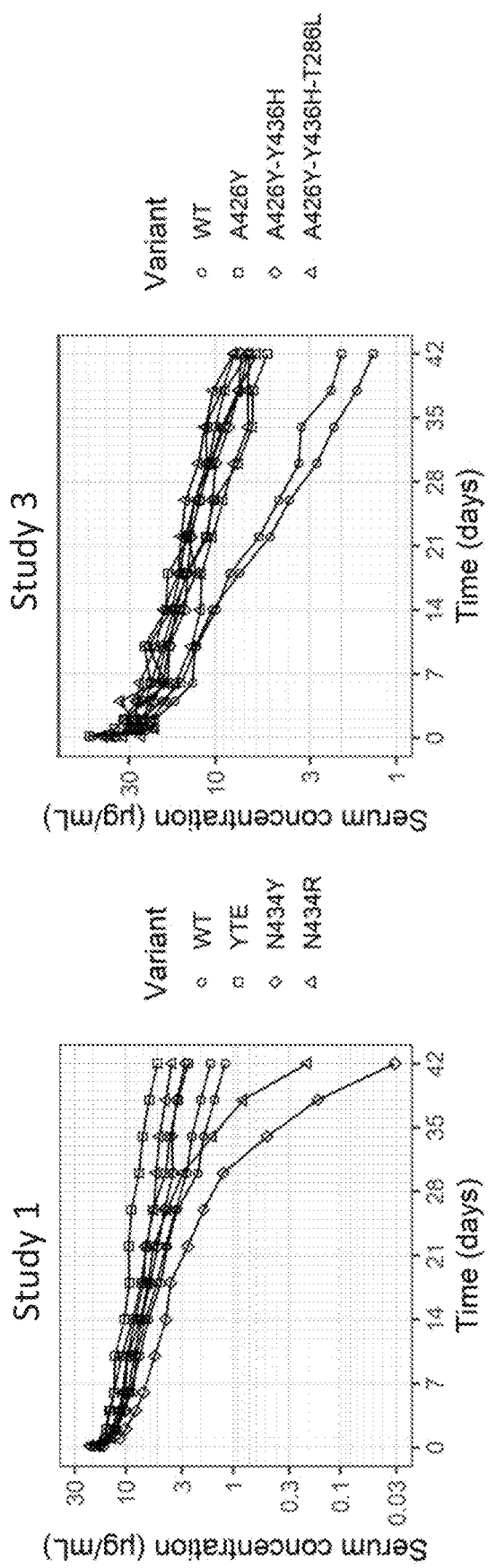
FIGS. 32A-32B show serum concentrations of different variants of IgGB overtime.

The individual observed serum concentrations of wild-type, A426Y, A426Y+Y436H, and A426Y+Y436H+T286L from Experiment 3 are shown in FIG. 32B. The individual observed serum concentration of wild-type, YTE, N434Y and N434R from Experiment 1 are also shown in FIG. 32A.

Figure 33:
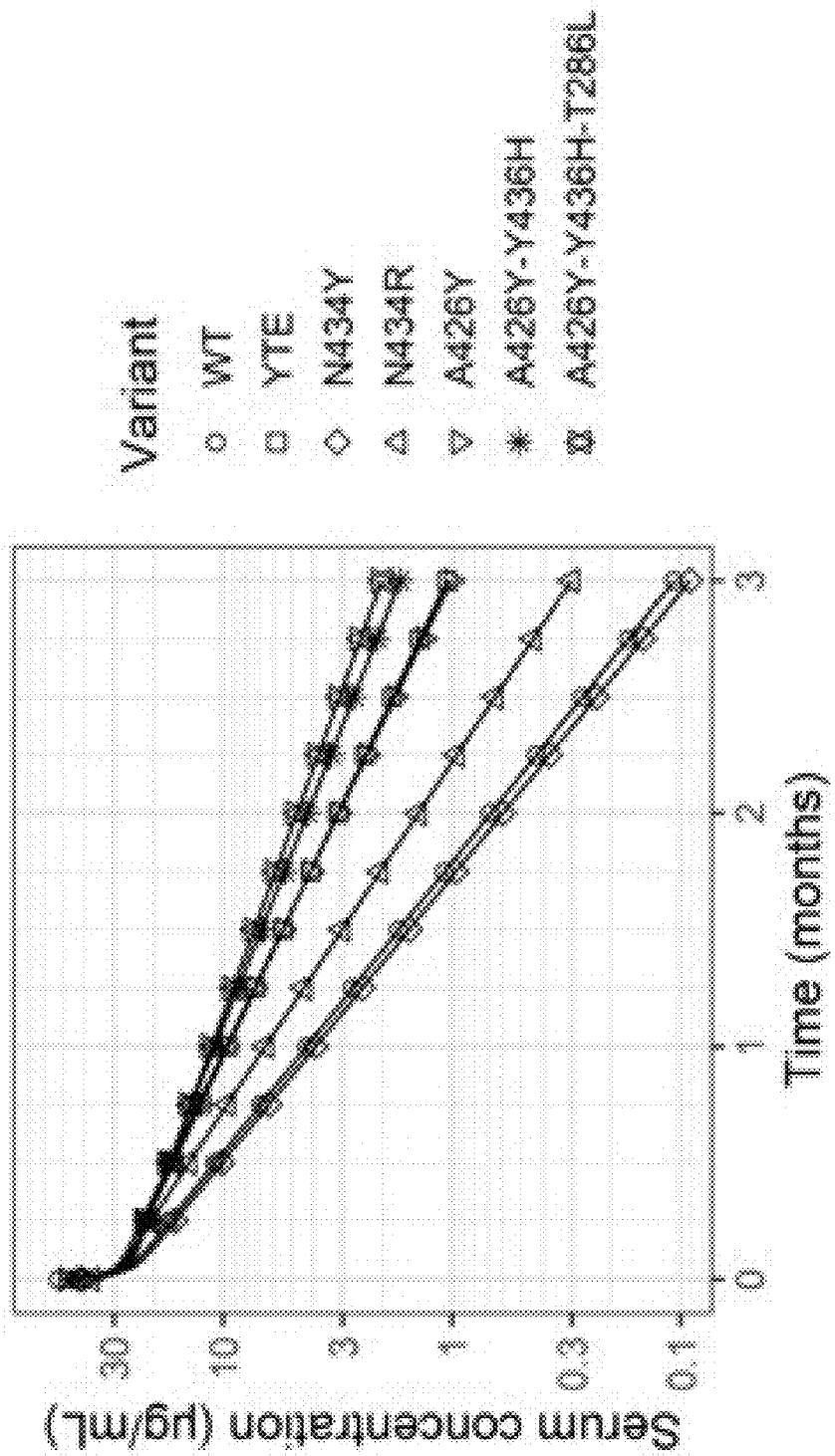
FIG. 33 shows the predicted serum concentration profiles of the antibodies carrying the wild-type IgGB Fc or the IgGB variants A426Y, A426Y+Y436H, A426Y+Y436H+T286L, N434R, N434Y, and YTE.

A simulation was determined for the predicted serum concentration profiles over a three month period of the anti-NGF antibodies carrying the wild-type IgGB Fc or the IgGB variants A426Y, A426Y+Y436H, A426Y+Y436H+ T286L, N434R, N434Y, and YTE and is shown in FIG. 33. For this simulation a 10 kg dog was used with a single 2 mg/kg intravenous dose.

Example 11: Modeling of Canine IgGB Fc Variants Binding to Canine FcRn

In order to provide insights on the molecular mechanisms of the canine IgGB Fc variants binding to canine FcRn, a structural model of canine IgGB Fc in complex with canine FcRn was created using MOE software (Molecular Operating Environment (MOE), 2020.09; Chemical Computing Group ULC, 1010 Sherbrooke St. West, Suite #910, Montreal, QC, Canada, H3A 2R7, 2020) based on the co-crystal structure of human FcRn in complex with the YTE-Fc domain (PDB ID:4NOU). Mutations were incorporated into the modeled structure in MOE and energy minimized with the Amber14:EHT forcefield. The Canine Fc-FcRn interaction distances were measured using Pymol software (The PyMOL Molecular Graphics System, Version 1.2r3pre, Schrödinger, LLC).

Figure 34:
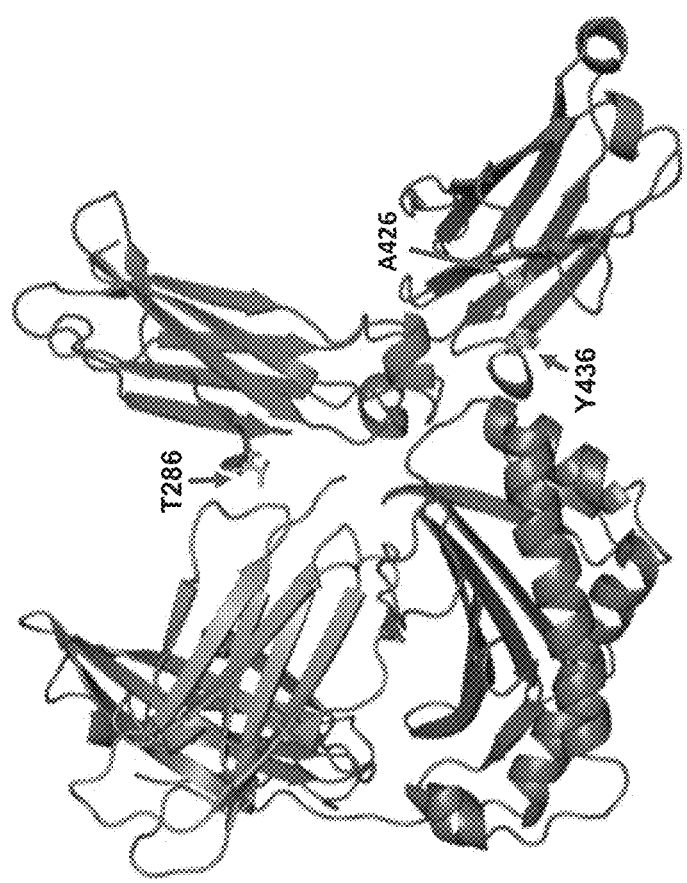
FIG. 34 shows the structural model of the canine Fc positions of 286, 426 and 436.

The canine Fc positions of 286, 426 and 436 which have variants that increase the affinity to canine FcRn at low pH are shown in FIG. 34.

Figure 35:
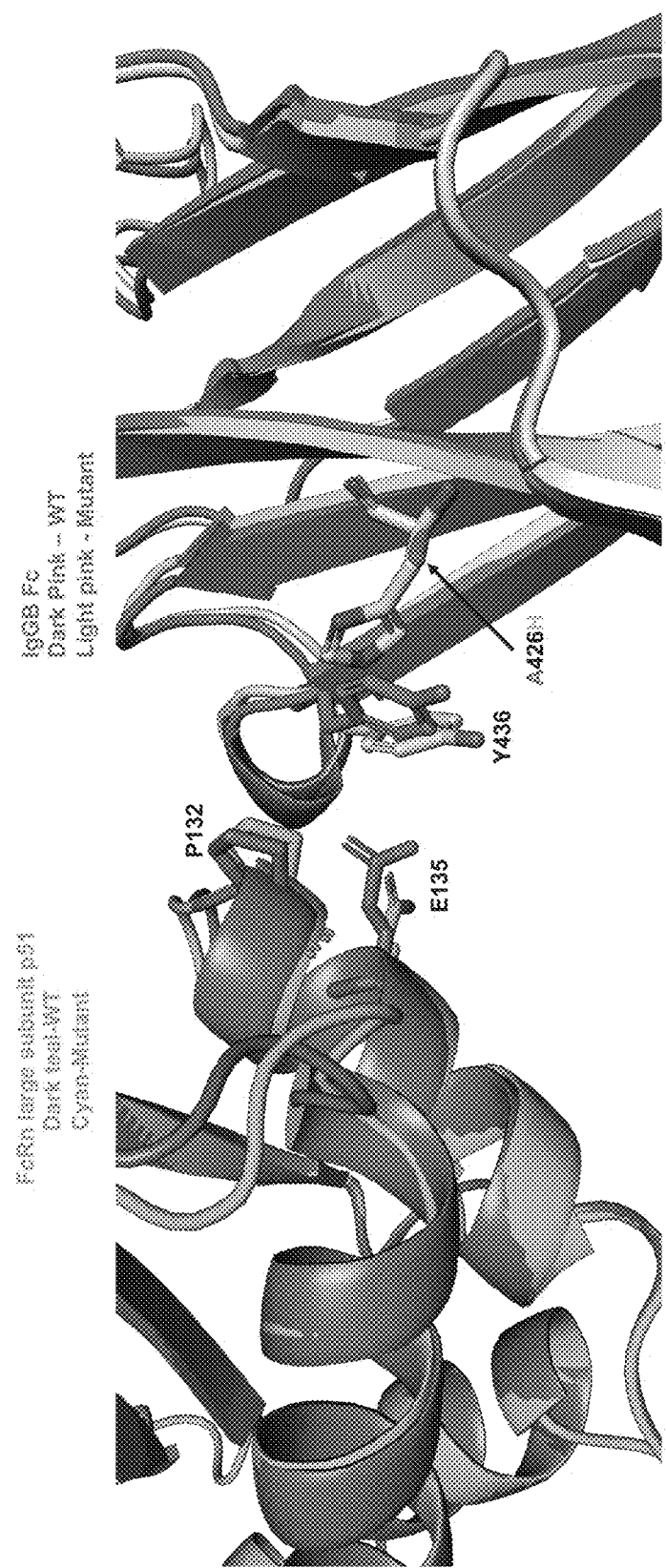
FIG. 35 shows the structural model of the canine Fc position of A426H. Left structures are FcRn large subunit p51. Right structures are IgGB Fc.
Figure 36:
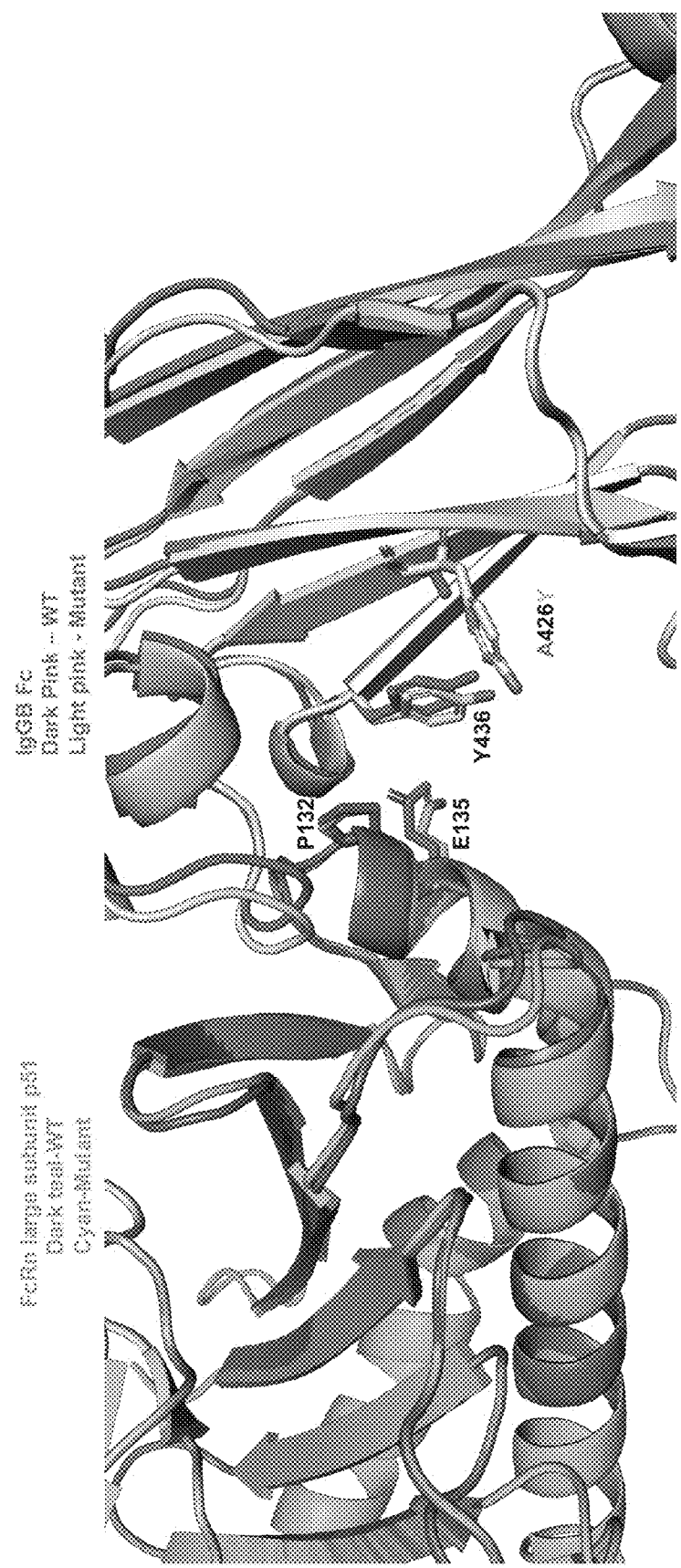
FIG. 36 shows the structural model of the canine Fc position of A426Y. Left structures are FcRn large subunit p51. Right structures are IgGB Fc.

The canine IgGB A426H variant is shown in FIG. 35 and position 426 is too distant to directly interact with FcRn. The model predicts that A426H causes a steric clash with Y436 which displaces it into a more favorable conformation for binding FcRn. The canine A426Y is shown in FIG. 36 and similar to A426H, it is too distant to directly interact with FcRn and shifts Y436 into a more favorable conformation for binding to FcRn.

Figure 37:
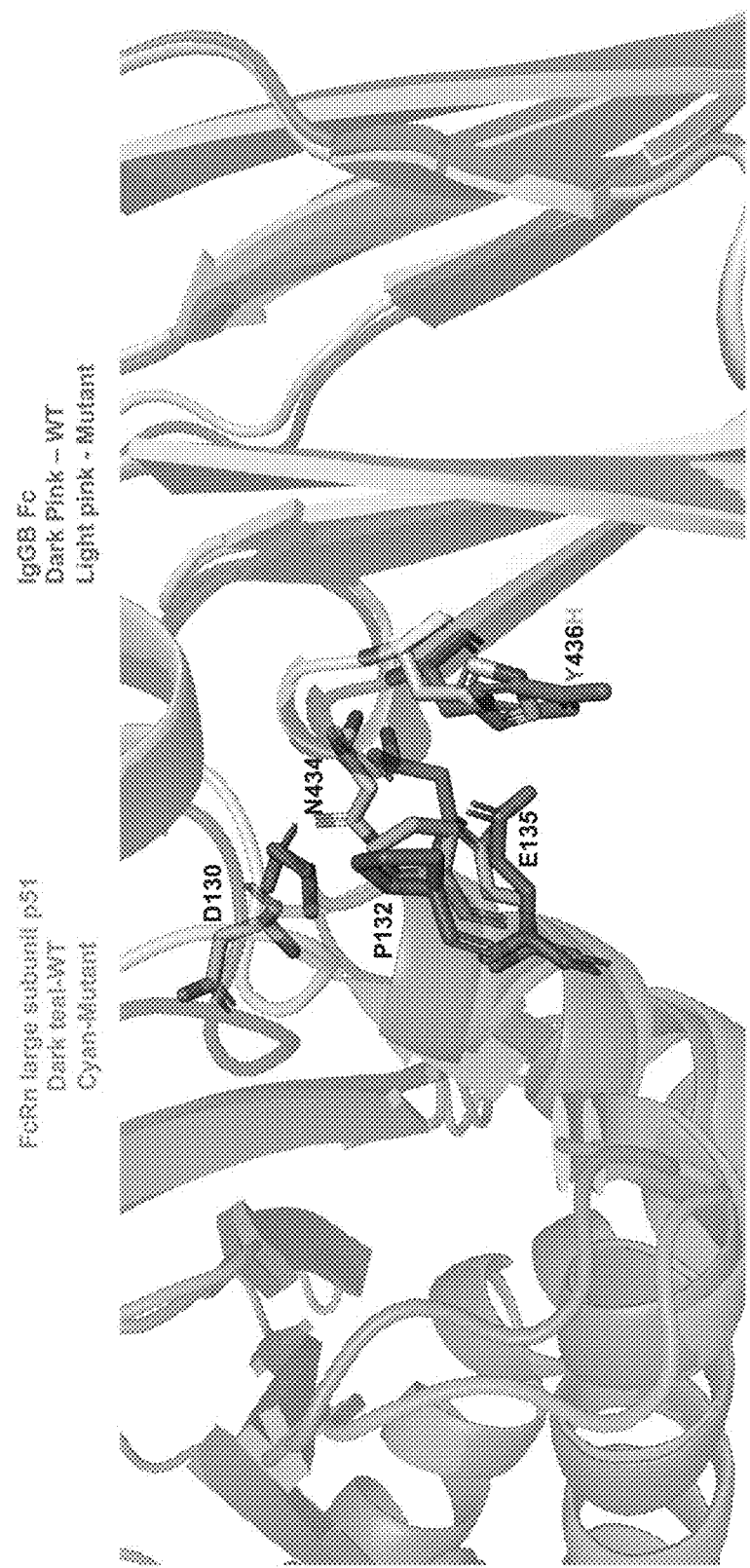
FIG. 37 shows the structural model of the canine Fc position of Y436H. Left structures are FcRn large subunit p51. Right structures are IgGB Fc.

The canine IgGB Y436H variant is shown in FIG. 37. Changing position 436 residue to a His has slight predicted changes to adjacent residues. The difference in charge is likely what is driving the tighter binding. The lack of charge on H436 at neutral pH similar to the hydrophobic/aromatic Y436 is predicted to drive adjacent residues to remain in an unfavorable environment for binding. However, the more hydrophilic/positively charge nature of protonated His436 provides a more attractive interface for residues such as E135 in FcRn large subunit.

Figure 38:
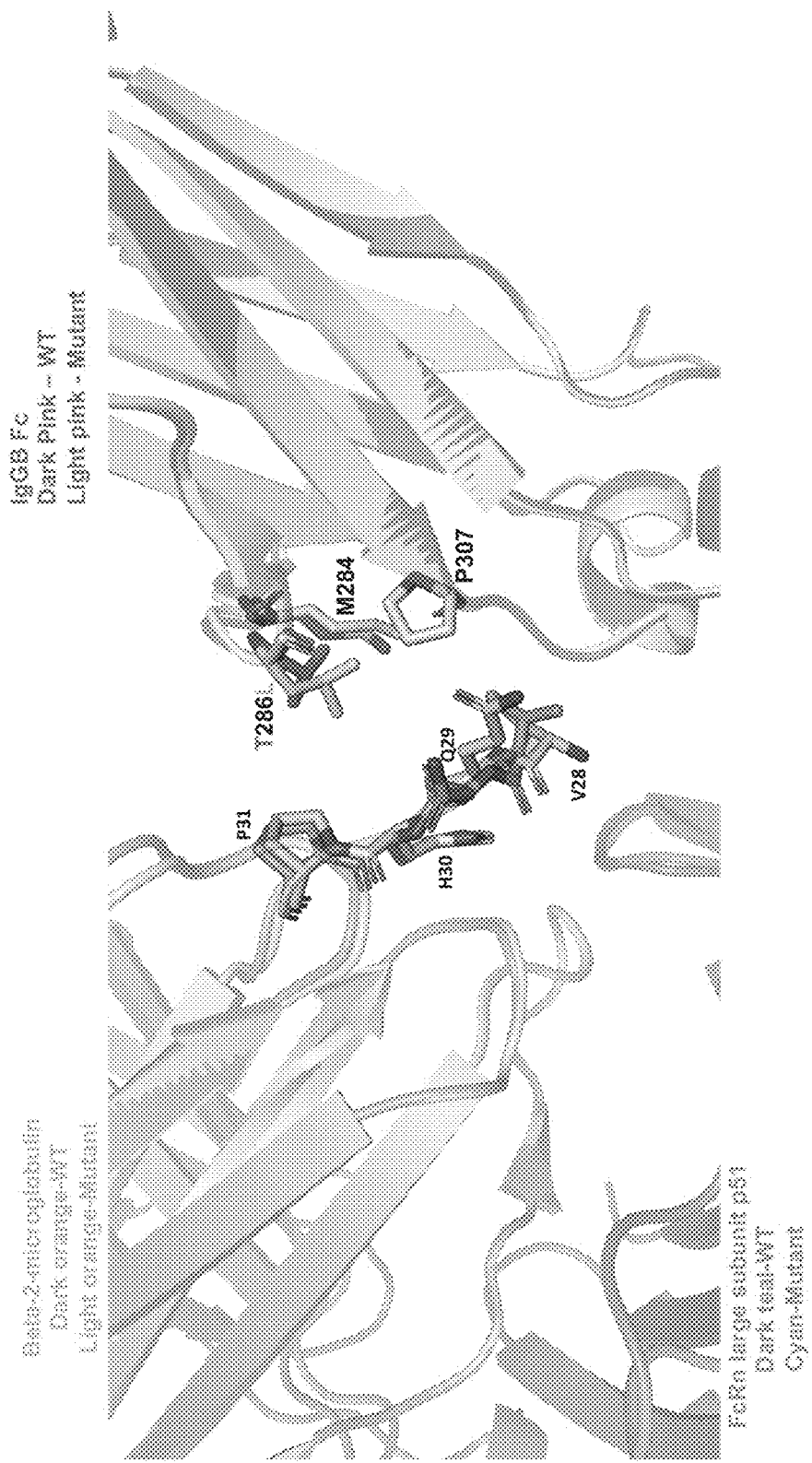
FIG. 38 shows the structural model of the canine Fc position of T286L. Left structures are beta-2-microglobulin and FcRn large subunit p51. Right structures are IgGB Fc.

The canine IgGB T286L variant is shown in FIG. 38 and is not directly interacting with canine beta-2-microglobulin in FcRn. However, any hydrophobic interactions present would be strengthened by changing a threonine to leucine. The observation is consistent with the increased affinities of T286Y, T286F, and T286W variants to canine FcRn at low pH, as shown in Examples 4 and 5.

Figure 39:
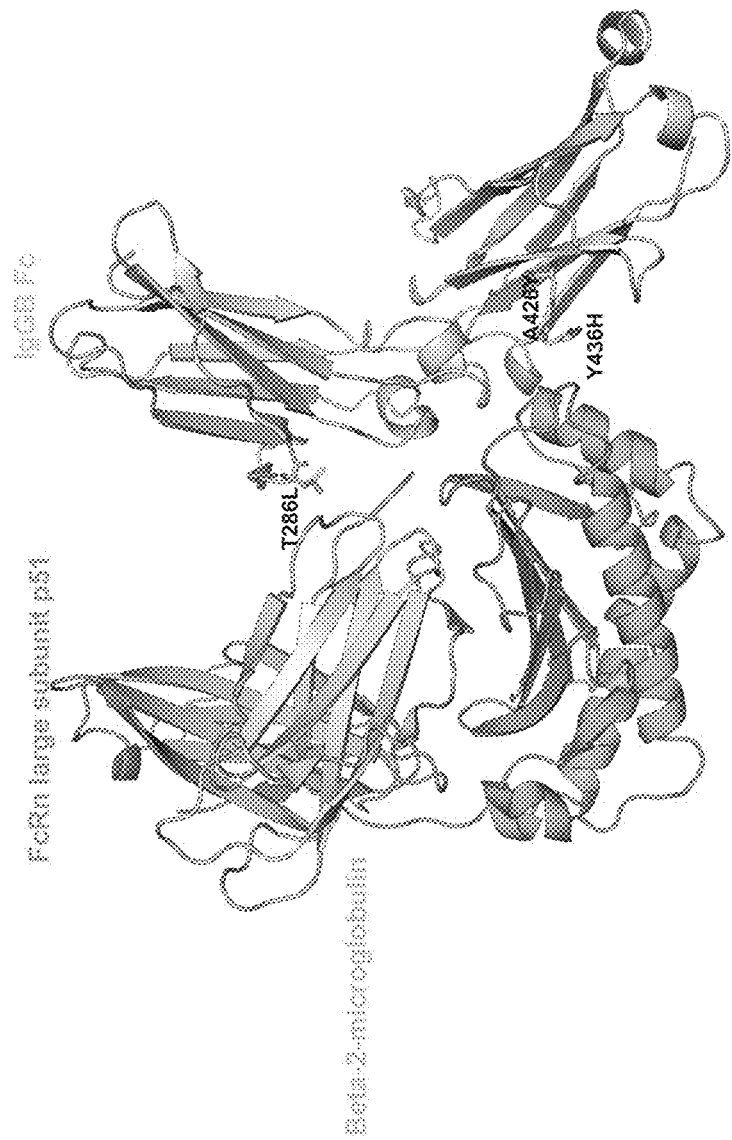
FIG. 39 shows the structural model of the canine Fc positions of T286L, A426Y, and Y436H. Left structures are beta-2-microglobulin and FcRn large subunit p51. Right structure is IgGB Fc.

The combination of A426Y, Y436H and T286L variants on the canine IgGB Fc has been modeled (FIG. 39). The steric clash between A426Y and Y436H variants is predicted to cause 436 to move into a position more favorable for binding. This is may be additive with the effect of pH dependence of the His. T286L is too far away to appear be directly influenced by 426 and 436 mutations. The in vitro binding data of the triple variant (A426Y, Y436H and T286L) to canine FcRn at low pH in Example 9 is consistent with the model that the combination of the three variants increases the FcRn affinity in an additive manner.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

In some aspects, the disclosure provides a polypeptide comprising a canine IgG Fc region variant, or a canine FcRn-binding region thereof, wherein the polypeptide comprises at least one amino acid substitution at a position selected from the group consisting of:
a position that corresponds to amino acid position 286 of a wild type canine IgG;
a position that corresponds to amino acid position 312 of a wild type canine IgG;
a position that corresponds to amino acid position 426 of a wild type canine IgG; and
a position that corresponds to amino acid position 436 of a wild type canine IgG,
wherein the amino acid substitution at the position that corresponds to amino acid position 286 of the wild type canine IgG is selected from the group consisting of Tyr, Phe, Leu and Trp,
wherein the amino acid positions are based on EU numbering, and wherein the polypeptide has increased binding affinity to canine FcRn when compared to an Fc domain of the wild type canine IgG.

In some embodiments, the at least one amino acid substitution comprises an amino acid substitution at the position that corresponds to amino acid position 312 of a wild type canine IgG.

In some embodiments, the polypeptide comprises Pro at the amino acid position that corresponds to amino acid position 312 of the wild type canine IgG.

In some embodiments, the at least one amino acid substitution comprises an amino acid substitution at the position that corresponds to amino acid position 426 of a wild type canine IgG. In some embodiments, the polypeptide comprises Tyr, His or Phe at the amino acid position that corresponds to amino acid position 426 of the wild type canine IgG. In some embodiments, the polypeptide comprises Tyr at the amino acid position that corresponds to amino acid position 426 of the wild type canine IgG. In some embodiments, the polypeptide comprises His at the amino acid position that corresponds to amino acid position 426 of the wild type canine IgG. In some embodiments, the polypeptide comprises Phe at the amino acid position that corresponds to amino acid position 426 of the wild type canine IgG.

In some embodiments, the at least one amino acid substitution comprises an amino acid substitution at the position that corresponds to amino acid position 436 of a wild type canine IgG. In some embodiments, the polypeptide comprises His at the amino acid position that corresponds to amino acid position 436 of the wild type canine IgG.

In some embodiments, the polypeptide comprises an amino acid sequence that is at least 80%, 90%, 95%, 98%, 99%, or 100% identical to an amino acid sequence selected from the group consisting of SEQ ID NOs: 9 to 12.

In some embodiments, the polypeptide comprises at least one additional amino acid substitution at a position selected from the group consisting of:
an amino acid position that corresponds to amino acid position 250 of the wild type canine IgG,
an amino acid position that corresponds to amino acid position 251 of the wild type canine IgG,
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG,
an amino acid position that corresponds to amino acid position 285 of the wild type canine IgG,
an amino acid position that corresponds to amino acid position 286 of the wild type canine IgG,
an amino acid position that corresponds to amino acid position 307 of the wild type canine IgG,
an amino acid position that corresponds to amino acid position 308 of the wild type canine IgG,
an amino acid position that corresponds to amino acid position 309 of the wild type canine IgG,
an amino acid position that corresponds to amino acid position 311 of the wild type canine IgG,
an amino acid position that corresponds to amino acid position 315 of the wild type canine IgG,
an amino acid position that corresponds to amino acid position 378 of the wild type canine IgG,
an amino acid position that corresponds to amino acid position 380 of the wild type canine IgG,
an amino acid position that corresponds to amino acid position 428 of the wild type canine IgG,
an amino acid position that corresponds to amino acid position 430 of the wild type canine IgG, an amino acid position that corresponds to amino acid position 433 of the wild type canine IgG,
an amino acid position that corresponds to amino acid position 434 of the wild type canine IgG, and
an amino acid position that corresponds to amino acid position 435 of the wild type canine IgG.

In some embodiments, the polypeptide comprises:
Glu or Gln at the amino acid position that corresponds to amino acid position 250 of the wild type canine IgG,
Asp or Glu at the amino acid position that corresponds to amino acid position 251 of the wild type canine IgG,
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG,
Asn or Asp at the amino acid position that corresponds to amino acid position 285 of the wild type canine IgG,
Asp, Tyr, Phe, Leu or Trp at the amino acid position that corresponds to amino acid position 286 of the wild type canine IgG,
Arg, Gln or Ala at the amino acid position that corresponds to amino acid position 307 of the wild type canine IgG,
Pro at the amino acid position that corresponds to amino acid position 308 of the wild type canine IgG,
Pro at the amino acid position that corresponds to amino acid position 309 of the wild type canine IgG,
Val at the amino acid position that corresponds to amino acid position 311 of the wild type canine IgG,
Asp at the amino acid position that corresponds to amino acid position 315 of the wild type canine IgG,
Val at the amino acid position that corresponds to amino acid position 378 of the wild type canine IgG,
Ala at the amino acid position that corresponds to amino acid position 380 of the wild type canine IgG,
Leu at the amino acid position that corresponds to amino acid position 428 of the wild type canine IgG,
Ala or Lys at the amino acid position that corresponds to amino acid position 430 of the wild type canine IgG,
Lys at the amino acid position that corresponds to amino acid position 433 of the wild type canine IgG,
Trp, Tyr, Arg, His, Ser, Ala or Phe at the amino acid position that corresponds to amino acid position 434 of the wild type canine IgG, and/or
Tyr at the amino acid position that corresponds to amino acid position 435 of the wild type canine IgG.

In some embodiments, the at least one amino acid substitution comprises an amino acid substitution at the position that corresponds to amino acid position 286 of the wild type canine IgG. In some embodiments, the polypeptide comprises Tyr at the amino acid position that corresponds to amino acid position 286 of the wild type canine IgG. In some embodiments, the polypeptide comprises Phe at the amino acid position that corresponds to amino acid position 286 of the wild type canine IgG. In some embodiments, the polypeptide comprises Leu at the amino acid position that corresponds to amino acid position 286 of the wild type canine IgG. In some embodiments, the polypeptide comprises Trp at the amino acid position that corresponds to amino acid position 286 of the wild type canine IgG.

In some embodiments, the polypeptide comprises at least one additional amino acid substitution at a position selected from the group consisting of:
an amino acid position that corresponds to amino acid position 250 of the wild type canine IgG,
an amino acid position that corresponds to amino acid position 251 of the wild type canine IgG,
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG, an amino acid position that corresponds to amino acid position 285 of the wild type canine IgG,
an amino acid position that corresponds to amino acid position 307 of the wild type canine IgG,
an amino acid position that corresponds to amino acid position 308 of the wild type canine IgG,
an amino acid position that corresponds to amino acid position 309 of the wild type canine IgG,
an amino acid position that corresponds to amino acid position 311 of the wild type canine IgG,
an amino acid position that corresponds to amino acid position 315 of the wild type canine IgG,
an amino acid position that corresponds to amino acid position 378 of the wild type canine IgG,
an amino acid position that corresponds to amino acid position 380 of the wild type canine IgG,
an amino acid position that corresponds to amino acid position 428 of the wild type canine IgG,
an amino acid position that corresponds to amino acid position 430 of the wild type canine IgG,
an amino acid position that corresponds to amino acid position 433 of the wild type canine IgG,
an amino acid position that corresponds to amino acid position 434 of the wild type canine IgG, and
an amino acid position that corresponds to amino acid position 435 of the wild type canine IgG.

In some embodiments, the polypeptide comprises:
Glu or Gln at the amino acid position that corresponds to amino acid position 250 of the wild type canine IgG,
Asp or Glu at the amino acid position that corresponds to amino acid position 251 of the wild type canine IgG,
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG,
Asn or Asp at the amino acid position that corresponds to amino acid position 285 of the wild type canine IgG,
Arg, Gln or Ala at the amino acid position that corresponds to amino acid position 307 of the wild type canine IgG,
Pro at the amino acid position that corresponds to amino acid position 308 of the wild type canine IgG,
Pro at the amino acid position that corresponds to amino acid position 309 of the wild type canine IgG,
Val at the amino acid position that corresponds to amino acid position 311 of the wild type canine IgG,
Asp at the amino acid position that corresponds to amino acid position 315 of the wild type canine IgG,
Val at the amino acid position that corresponds to amino acid position 378 of the wild type canine IgG,
Ala at the amino acid position that corresponds to amino acid position 380 of the wild type canine IgG,
Leu at the amino acid position that corresponds to amino acid position 428 of the wild type canine IgG,
Ala or Lys at the amino acid position that corresponds to amino acid position 430 of the wild type canine IgG,
Lys at the amino acid position that corresponds to amino acid position 433 of the wild type canine IgG, Trp, Tyr, Arg, His, Ser, Ala or Phe at the amino acid position that corresponds to amino acid position 434 of the wild type canine IgG, and/or Tyr at the amino acid position that corresponds to amino acid position 435 of the wild type canine IgG.

In some embodiments, the at least one additional amino acid substitution is at a position selected from the group consisting of:

an amino acid position that corresponds to amino acid position 250 of the wild type canine IgG,
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG,
an amino acid position that corresponds to amino acid position 285 of the wild type canine IgG,
an amino acid position that corresponds to amino acid position 307 of the wild type canine IgG,
an amino acid position that corresponds to amino acid position 309 of the wild type canine IgG,
an amino acid position that corresponds to amino acid position 311 of the wild type canine IgG,
an amino acid position that corresponds to amino acid position 315 of the wild type canine IgG,
an amino acid position that corresponds to amino acid position 433 of the wild type canine IgG, and
an amino acid position that corresponds to amino acid position 434 of the wild type canine IgG.

In some embodiments, the polypeptide comprises:
Glu or Gln at the amino acid position that corresponds to amino acid position 250 of the wild type canine IgG,
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG,
Asn or Asp at the amino acid position that corresponds to amino acid position 285 of the wild type canine IgG,
Arg, Gln or Ala at the amino acid position that corresponds to amino acid position 307 of the wild type canine IgG,
Pro at the amino acid position that corresponds to amino acid position 309 of the wild type canine IgG,
Val at the amino acid position that corresponds to amino acid position 311 of the wild type canine IgG,
Asp at the amino acid position that corresponds to amino acid position 315 of the wild type canine IgG,
Lys at the amino acid position that corresponds to amino acid position 433 of the wild type canine IgG, and
Trp, Tyr, Arg, His, Ser, Ala or Phe at the amino acid position that corresponds to amino acid position 434 of the wild type canine IgG.

In some embodiments, the at least one additional amino acid substitution is at a position selected from the group consisting of:
an amino acid position that corresponds to amino acid position 252 of the wild type canine IgG,
an amino acid position that corresponds to amino acid position 254 of the wild type canine IgG,
an amino acid position that corresponds to amino acid position 256 of the wild type canine IgG, and
an amino acid position that corresponds to amino acid position 434 of the wild type canine IgG.

In some embodiments, the polypeptide comprises:
Tyr or Met at the amino acid position that corresponds to amino acid position 252 of the wild type canine IgG,
Thr or Ser at the amino acid position that corresponds to amino acid position 254 of the wild type canine IgG,
Asp, Glu or Phe at the amino acid position that corresponds to amino acid position 256 of the wild type canine IgG, and/or
Trp, Tyr, Arg, His, Ser, Ala or Phe at the amino acid position that corresponds to amino acid position 434 of the wild type canine IgG.

In some embodiments, the polypeptide comprises:
Tyr at the amino acid position that corresponds to amino acid position 252 of the wild type canine IgG,
Thr at the amino acid position that corresponds to amino acid position 254 of the wild type canine IgG,
Glu at the amino acid position that corresponds to amino acid position 256 of the wild type canine IgG, and/or
Trp, Tyr, Arg or His at the amino acid position that corresponds to amino acid position 434 of the wild type canine IgG.

In some embodiments, the polypeptide further comprises at least one of the following:
Tyr at amino acid position 252, Thr at amino acid position 254, and Glu at amino acid position 256;
Leu at amino acid position 428 and Ser at amino acid position 434;
Asp at amino acid position 256, Arg at amino acid position 307, and Val at amino acid position 311;
Asp at amino acid position 256, Asp at amino acid position 315, and Val at amino acid position 378;
Asp at amino acid position 256, Asp, Tyr, Phe, Leu or Trp at amino acid position 286, Arg at amino acid position 307, and Val at amino acid position 311;
Asn at amino acid position 285, Gln at amino acid position 307, and Asp at amino acid position 315;
Asp at amino acid position 256, Arg at amino acid position 307, Val at amino acid position 311, and Val at amino acid position 378;
Asp at amino acid position 285, Val at amino acid position 311, and Val at amino acid position 378;
Asp at amino acid position 256, Asp at amino acid position 285, and Val at amino acid position 378;
Asp at amino acid position 256, Val at amino acid position 311, and Val at amino acid position 378;
Asp at amino acid position 256, Asp at amino acid position 285, Asp, Tyr, Phe, Leu or Trp at amino acid position 286, Arg at amino acid position 307, and Val at amino acid position 378;
Asp at amino acid position 256, Asp, Tyr, Phe, Leu or Trp at amino acid position 286, Arg at amino acid position 307, Val at amino acid position 311, and Val at position 378;
Gln at amino acid position 307, Val at amino acid position 311, and Val at amino acid position 378;
Asp at amino acid position 285, Gln at amino acid position 307, and Val at amino acid position 378;
Asp at amino acid position 256, Asp at amino acid position 285, Arg at amino acid position 307,
Val at amino acid position 311, and Val at amino acid position 378;
Gln at amino acid position 307, Ala at amino acid position 380, Ser or Ala at amino acid position 434;
Leu at amino acid position 428, and Ser or Ala at amino acid position 434; or
Gln at amino acid position 250 and Leu at amino acid position 428.

In some aspects, the disclosure provides a polypeptide comprising a canine IgG Fc region variant, or a canine FcRn-binding region thereof, wherein the polypeptide comprises amino acid substitutions at two or more positions selected from the group consisting of:

a position that corresponds to amino acid position 286 of a wild type canine IgG;

a position that corresponds to amino acid position 312 of a wild type canine IgG;

a position that corresponds to amino acid position 426 of a wild type canine IgG;

a position that corresponds to amino acid position 434 of a wild type canine IgG; and a position that corresponds to amino acid position 436 of a wild type canine IgG, wherein the amino acid positions are based on EU numbering, and wherein the polypeptide has increased binding affinity to canine FcRn when compared to an Fc domain of the wild type canine IgG.

In some embodiments, the amino acid substitution at the position that corresponds to amino acid position 286 of a wild type canine IgG is selected from the group consisting of T286L, T286Y and conservative amino acid substitutions of any of the foregoing.

In some embodiments, the polypeptide of claim 1, wherein the amino acid substitution at the position that corresponds to amino acid position 312 of a wild type canine IgG is D312P or a conservative amino acid substitution thereof.

In some embodiments, the amino acid substitution at the position that corresponds to amino acid position 426 of a wild type canine IgG is selected from the group consisting of A426Y, A426H and conservative amino acid substitutions of any of foregoing.

In some embodiments, the amino acid substitution at the position that corresponds to amino acid position 434 of a wild type canine IgG is N434R or a conservative amino acid substitution thereof.

In some embodiments, the amino acid substitution at the position that corresponds to amino acid position 436 of a wild type canine IgG is Y436H or a conservative amino acid substitution thereof.

In some embodiments, the polypeptide comprises an amino acid substitution at the position that corresponds to amino acid position 426 of a wild type canine IgG.

In some embodiments, the polypeptide comprises amino acid substitutions at the two or more positions selected from the group consisting of:

positions that correspond to amino acid positions 426 and 286 of a wild type canine IgG;

positions that correspond to amino acid position 426 and 312 of a wild type canine IgG;

positions that correspond to amino acid position 426 and 434 of a wild type canine IgG;

positions that correspond to amino acid position 426 and 436 of a wild type canine IgG; and positions that correspond to amino acid position 286, 426 and 436 of a wild type canine IgG.

In some embodiments, the polypeptide comprises amino acid substitutions selected from the group consisting of:

(i) A426Y and T286L;
(ii) A426Y and D312P;
(iii) A426Y and Y436H;
(iv) A426H and T286L;
(v) A426H and T286Y;
(vi) A426H and D312P; and
(vii) T286L, A426Y, and Y436H.

In some embodiments, the two or more amino acid substitutions are selected from the group consisting of:

A426Y in combination with one or more of T286L, D312P, N434R and Y436H;

A426H in combination with one or more of T286L, T286Y, D312P, N434R and Y436H; and N434R in combination with one or more of T286L, T286Y, D312P and Y436H.

In some embodiments, the wild type canine IgG is a canine IgGA comprising an Fc domain having an amino acid sequence that is at least 80%, at least 85%, at least 90%, or at least 95% identical to SEQ ID NO: 9, a canine IgGB comprising an Fc domain having an amino acid sequence that is at least 80%, at least 85%, at least 90%, or at least 95% identical to SEQ ID NO: 10, a canine IgGC comprising an Fc domain having an amino acid sequence that is at least 80%, at least 85%, at least 90%, or at least 95% identical to SEQ ID NO: 11, or a canine IgGD comprising an Fc domain having amino acid sequence that is at least 80%, at least 85%, at least 90%, or at least 95% identical to SEQ ID NO: 12.

In some embodiments, the wild type canine IgG is a canine IgGA, and the canine IgG Fc region variant or the canine FcRn-binding region thereof comprises an amino acid sequence that is at least 80%, at least 85%, at least 90%, or at least 95% identical to SEQ ID NO: 9. In some embodiments, the wild type canine IgG is a canine IgGB, and the canine IgG Fc region variant or the canine FcRn-binding region thereof comprises an amino acid sequence that is at least 80%, at least 85%, at least 90%, or at least 95% identical to SEQ ID NO: 10. In some embodiments, the wild type canine IgG is a canine IgGC, and the canine IgG Fc region variant or the canine FcRn-binding region thereof comprises an amino acid sequence that is at least 80%, at least 85%, at least 90%, or at least 95% identical to SEQ ID NO: 11. In some embodiments, the wild type canine IgG is a canine IgGD, and the canine IgG Fc region variant or the canine FcRn-binding region thereof comprises an amino acid sequence that is at least 80%, at least 85%, at least 90%, or at least 95% identical to SEQ ID NO: 12.

In some embodiments, the wild type canine IgG is a canine IgGA, and the canine IgG Fc region variant or the canine FcRn-binding region thereof comprises an amino acid sequence that is at least 80%, at least 85%, at least 90%, or at least 95% identical to SEQ ID NO: 9.

In some embodiments, the wild type canine IgG is a canine IgGB, and the canine IgG Fc region variant or the canine FcRn-binding region thereof comprises an amino acid sequence that is at least 80%, at least 85%, at least 90%, or at least 95% identical to SEQ ID NO: 10.

In some embodiments, the wild type canine IgG is a canine IgGC, and the canine IgG Fc region variant or the canine FcRn-binding region thereof comprises an amino acid sequence that is at least 80%, at least 85%, at least 90%, or at least 95% identical to SEQ ID NO: 11.

In some embodiments, the wild type canine IgG is a canine IgGD, and the canine IgG Fc region variant or the canine FcRn-binding region thereof comprises an amino acid sequence that is at least 80%, at least 85%, at least 90%, or at least 95% identical to SEQ ID NO: 12.

In some embodiments, the polypeptide further comprises a binding domain.

In some embodiments, the binding domain comprises (i) six complementarity determining regions (CDRs) of an immunoglobulin molecule; (ii) a ligand binding domain of a canine receptor protein, (iii) a nanobody, or (iv) an extracellular domain of a canine receptor protein.

In some embodiments, the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

In some embodiments, the polypeptide further comprises a protein selected from the group consisting of EPO, CTLA4, LFA3, VEGFR1/VEGFR3, IL-1R, IL-4R, GLP-1 receptor agonist, and Thrombopoietin binding peptide.

In some embodiments, the polypeptide binds to a canine FcRn at a higher level at an acidic pH than at a neutral pH in a binding assay. In some embodiments, the polypeptide binds to a canine FcRn at a higher level at pH 5.5 than at pH 7.4 in a binding assay. In some embodiments, the polypeptide binds to a canine FcRn at a higher level at pH 6.0 than at pH 7.4 in a binding assay.

In some embodiments, the polypeptide has: (1) increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant; and/or (2) increased binding to canine FcRn than the control polypeptides; and wherein the amino acid positions are based on EU numbering.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:9.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:10.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:11.

In some embodiments, the polypeptide comprises an amino acid sequence that is at least 80%, at least 85%, at least 90%, at least 95%, at least 96%, at least 97%, at least 98%, at least 99%, or 100% identical to SEQ ID NO:12.

In some aspects, the disclosure provides a pharmaceutical composition comprising (i) the polypeptide described herein, and (ii) a pharmaceutically acceptable excipient.

In some aspects, the disclosure provides a nucleic acid or nucleic acids encoding the polypeptide described herein.

In some aspects, the disclosure provides an expression vector or expression vectors comprising the nucleic acid or nucleic acids described herein.

In some aspects, the disclosure provides a host cell comprising the nucleic acid or nucleic acids described herein or the expression vector or expression vectors described herein.

In some aspects, the disclosure provides a method of making a polypeptide or polypeptides, the method comprising:
(a) providing a nucleic acid or nucleic acids described herein;
(b) expressing the nucleic acid or nucleic acids in a host cell culture, thereby producing the polypeptide; and
(c) collecting the polypeptide produced in (b) from the host cell culture.

In some embodiments, the method further comprises formulating the polypeptide as a pharmaceutical formulation.

In some aspects, the disclosure provides a method of treating a canine disease or disorder in a dog in need thereof, the method comprising administering an effective amount of a composition comprising the pharmaceutical composition described herein to the dog.

In some aspects, the disclosure provides a method of preventing a canine disease or disorder in a dog in need thereof, the method comprising administering an effective amount of a composition comprising the pharmaceutical composition described herein to the dog.

In some aspects, the disclosure provides a pharmaceutical composition described herein for use in a method of treating a canine disease or disorder in a dog in need thereof.

In some aspects, the disclosure provides a pharmaceutical composition described herein for use in a method of preventing a canine disease or disorder in a dog in need thereof.

In some aspects, the disclosure provides use of the polypeptide described herein in the manufacture of a medicament for treating a canine disease or disorder in a dog in need thereof.

In some aspects, the disclosure provides use of the polypeptide described herein in the manufacture of a medicament for preventing a canine disease or disorder in a dog in need thereof.

In some embodiments, the disease or disorder is an allergic disease, a chronic pain, an acute pain, an inflammatory disease, an autoimmune disease, an endocrine disease, a gastrointestinal disease, a cardiovascular disease, a renal disease, a fertility related disorder, an infectious disease or a cancer.

In some embodiments, the disease or disorder is atopic dermatitis, allergic dermatitis, osteoarthritic pain, arthritis, anemia, or obesity.

What is claimed is:

1. A polypeptide comprising a canine IgG Fc region variant, or a canine FcRn-binding region thereof, wherein the canine IgG Fc region variant, or the canine FcRn-binding region thereof, comprises amino acid substitutions at positions selected from the group consisting of:
   (i) positions that correspond to amino acid positions 426 and 286 of a wild type canine IgG;
   (ii) positions that correspond to amino acid position 426 and 312 of a wild type canine IgG;
   (iii) positions that correspond to amino acid position 426 and 434 of a wild type canine IgG;
   (iv) positions that correspond to amino acid position 426 and 436 of a wild type canine IgG; and
   (v) positions that correspond to amino acid position 286, 426 and 436 of a wild type canine IgG
   wherein the amino acid positions are based on EU numbering, wherein the polypeptide has increased binding affinity to canine FcRn when compared to an Fc domain of the wild type canine IgG, and wherein the wild type canine IgG is a canine IgG.B comprising an Fc domain having the amino acid sequence of SEQ ID NO: 10.

2. The polypeptide of claim 1, wherein the amino acid substitution at the position that corresponds to amino acid position 286 of a wild type canine IgG is T286L or T286Y.

3. The polypeptide of claim 1, wherein the amino acid substitution at the position that corresponds to amino acid position 312 of a wild type canine IgG is D312P.

4. The polypeptide of claim 1, wherein the amino acid substitution at the position that corresponds to amino acid position 426 of a wild type canine IgG is A426Y or A426H.

5. The polypeptide of claim 1, wherein the amino acid substitution at the position that corresponds to amino acid position 434 of a wild type canine IgG is N434R.

6. The polypeptide of claim 1, wherein the amino acid substitution at the position that corresponds to amino acid position 436 of a wild type canine IgG is Y436H.

7. The polypeptide of claim 1, wherein the canine IgG Fc region variant, or the canine FcRn-binding region thereof, comprises amino acid substitutions selected from the group consisting of:
   (i) A426Y and T286L;
   (ii) A426Y and D312P;
   (iii) A426Y and Y436H;
   (iv) A426H and T286L;
   (v) A426H and T286Y;
   (vi) A426H and D312P; and
   (vii) T286L, A426Y, and Y436H.

8. The polypeptide of claim 1, wherein the polypeptide binds to a canine FcRn at a higher level at an acidic pH than at a neutral pH in a binding assay.

9. The polypeptide of claim 1, further comprising a binding domain comprising (i) six complementarity determining regions (CDRs) of an immunoglobulin molecule; (ii) a ligand binding domain of a canine receptor protein, (iii) a nanobody, or (iv) an extracellular domain of a canine receptor protein.

10. A fusion molecule comprising the polypeptide of claim 1 and a polypeptide selected from the group consisting of EPO, CTLA4, LFA3, VEGFR1/VEGFR3, IL-1R, IL-4R, GLP-1 receptor agonist, and Thrombopoietin binding peptide.

11. A pharmaceutical composition comprising (i) the polypeptide of claim 1, and (ii) a pharmaceutically acceptable excipient.

12. A polypeptide comprising a canine IgG Fc region variant, or a canine FcRn-binding region thereof, wherein the canine IgG Fc region variant, or the canine FcRn-binding region thereof, comprises amino acid substitutions at positions selected from the group consisting of:
   (i) A426Y in combination with one or more of T286L, D312P, N434R and Y436H;
   (ii) A426H in combination with one or more of T286L, T286Y, D312P, N434R and Y436H; and
   (iii) N434R in combination with one or more of T286L, T286Y, D312P and Y436H;
   wherein the amino acid positions are based on EU numbering, wherein the polypeptide has increased binding affinity to canine FcRn when compared to an Fc domain of a wild type canine IgG, and wherein the wild type canine IgG is a canine IgG.B comprising an Fc domain having the amino acid sequence of SEQ ID NO: 10.

13. A polypeptide comprising a canine IgG Fc region variant, or a canine FcRn-binding region thereof, wherein the canine IgG Fc region variant, or the canine FcRn-binding region thereof, comprises amino acid substitutions A426Y and T286L;
   wherein the amino acid positions are based on EU numbering, wherein the polypeptide has increased binding affinity to canine FcRn when compared to an Fc domain of a wild type canine IgG, and wherein the wild type canine IgG is a canine IgG.B comprising an Fc domain having the amino acid sequence of SEQ ID NO: 10.

* * * * *

SEQUENCE LISTING

```
<160> NUMBER OF SEQ ID NOS: 31

<210> SEQ ID NO 1
<211> LENGTH: 104
<212> TYPE: PRT
<213> ORGANISM: Canine

<400> SEQUENCE: 1

Gly Pro Ser Val Leu Ile Phe Pro Pro Lys Pro Lys Asp Ile Leu Arg
1               5                   10                  15

Ile Thr Arg Thr Pro Glu Val Thr Cys Val Val Leu Asp Leu Gly Arg
            20                  25                  30

Glu Asp Pro Glu Val Gln Ile Ser Trp Phe Val Asp Gly Lys Glu Val
```

```
            35                  40                  45
His Thr Ala Lys Thr Gln Ser Arg Glu Gln Gln Phe Asn Gly Thr Tyr
 50                  55                  60

Arg Val Val Ser Val Leu Pro Ile Glu His Gln Asp Trp Leu Thr Gly
 65                  70                  75                  80

Lys Glu Phe Lys Cys Arg Val Asn His Ile Asp Leu Pro Ser Pro Ile
                 85                  90                  95

Glu Arg Thr Ile Ser Lys Ala Arg
                100

<210> SEQ ID NO 2
<211> LENGTH: 104
<212> TYPE: PRT
<213> ORGANISM: Canine

<400> SEQUENCE: 2

Gly Pro Ser Val Phe Ile Phe Pro Pro Lys Pro Lys Asp Thr Leu Leu
 1               5                  10                  15

Ile Ala Arg Thr Pro Glu Val Thr Cys Val Val Val Asp Leu Asp Pro
                 20                  25                  30

Glu Asp Pro Glu Val Gln Ile Ser Trp Phe Val Asp Gly Lys Gln Met
             35                  40                  45

Gln Thr Ala Lys Thr Gln Pro Arg Glu Glu Gln Phe Asn Gly Thr Tyr
 50                  55                  60

Arg Val Val Ser Val Leu Pro Ile Gly His Gln Asp Trp Leu Lys Gly
 65                  70                  75                  80

Lys Gln Phe Thr Cys Lys Val Asn Asn Lys Ala Leu Pro Ser Pro Ile
                 85                  90                  95

Glu Arg Thr Ile Ser Lys Ala Arg
                100

<210> SEQ ID NO 3
<211> LENGTH: 104
<212> TYPE: PRT
<213> ORGANISM: Canine

<400> SEQUENCE: 3

Gly Pro Ser Val Phe Ile Phe Pro Pro Lys Pro Lys Asp Ile Leu Val
 1               5                  10                  15

Thr Ala Arg Thr Pro Thr Val Thr Cys Val Val Val Asp Leu Asp Pro
                 20                  25                  30

Glu Asn Pro Glu Val Gln Ile Ser Trp Phe Val Asp Ser Lys Gln Val
             35                  40                  45

Gln Thr Ala Asn Thr Gln Pro Arg Glu Glu Gln Ser Asn Gly Thr Tyr
 50                  55                  60

Arg Val Val Ser Val Leu Pro Ile Gly His Gln Asp Trp Leu Ser Gly
 65                  70                  75                  80

Lys Gln Phe Lys Cys Lys Val Asn Asn Lys Ala Leu Pro Ser Pro Ile
                 85                  90                  95

Glu Glu Ile Ile Ser Lys Thr Pro
                100

<210> SEQ ID NO 4
<211> LENGTH: 104
<212> TYPE: PRT
<213> ORGANISM: Canine

<400> SEQUENCE: 4
```

```
Gly Pro Ser Val Phe Ile Phe Pro Lys Pro Lys Asp Ile Leu Arg
1               5                   10                  15

Ile Thr Arg Thr Pro Glu Ile Thr Cys Val Val Leu Asp Leu Gly Arg
                20                  25                  30

Glu Asp Pro Glu Val Gln Ile Ser Trp Phe Val Asp Gly Lys Glu Val
            35                  40                  45

His Thr Ala Lys Thr Gln Pro Arg Glu Gln Gln Phe Asn Ser Thr Tyr
50                  55                  60

Arg Val Val Ser Val Leu Pro Ile Glu His Gln Asp Trp Leu Thr Gly
65                  70                  75                  80

Lys Glu Phe Lys Cys Arg Val Asn His Ile Gly Leu Pro Ser Pro Ile
                85                  90                  95

Glu Arg Thr Ile Ser Lys Ala Arg
                100
```

<210> SEQ ID NO 5
<211> LENGTH: 106
<212> TYPE: PRT
<213> ORGANISM: Canine

<400> SEQUENCE: 5

```
Lys Pro Ser Val Tyr Val Leu Pro Pro Ser Lys Glu Leu Ser Ser
1               5                   10                  15

Ser Asp Thr Val Ser Ile Thr Cys Leu Ile Lys Asp Phe Tyr Pro Pro
                20                  25                  30

Asp Ile Asp Val Glu Trp Gln Ser Asn Gly Gln Gln Glu Pro Glu Arg
            35                  40                  45

Lys His Arg Met Thr Pro Pro Gln Leu Asp Glu Asp Gly Ser Tyr Phe
50                  55                  60

Leu Tyr Ser Lys Leu Ser Val Asp Lys Ser Arg Trp Gln Gln Gly Asp
65                  70                  75                  80

Pro Phe Thr Cys Ala Val Met His Glu Thr Leu Gln Asn His Tyr Thr
                85                  90                  95

Asp Leu Ser Leu Ser His Ser Pro Gly Lys
                100                 105
```

<210> SEQ ID NO 6
<211> LENGTH: 105
<212> TYPE: PRT
<213> ORGANISM: Canine

<400> SEQUENCE: 6

```
Gln Pro Ser Val Tyr Val Leu Pro Pro Ser Arg Glu Glu Leu Ser Lys
1               5                   10                  15

Asn Thr Val Ser Leu Thr Cys Leu Ile Lys Asp Phe Phe Pro Pro Asp
                20                  25                  30

Ile Asp Val Glu Trp Gln Ser Asn Gly Gln Gln Glu Pro Glu Ser Lys
            35                  40                  45

Tyr Arg Thr Thr Pro Pro Gln Leu Asp Glu Asp Gly Ser Tyr Phe Leu
50                  55                  60

Tyr Ser Lys Leu Ser Val Asp Lys Ser Arg Trp Gln Arg Gly Asp Thr
65                  70                  75                  80

Phe Ile Cys Ala Val Met His Glu Ala Leu His Asn His Tyr Thr Gln
                85                  90                  95

Glu Ser Leu Ser His Ser Pro Gly Lys
                100                 105
```

```
<210> SEQ ID NO 7
<211> LENGTH: 105
<212> TYPE: PRT
<213> ORGANISM: Canine

<400> SEQUENCE: 7

Gln Pro Asn Val Tyr Val Leu Pro Pro Ser Arg Asp Glu Met Ser Lys
1               5                   10                  15

Asn Thr Val Thr Leu Thr Cys Leu Val Lys Asp Phe Phe Pro Pro Glu
            20                  25                  30

Ile Asp Val Glu Trp Gln Ser Asn Gly Gln Gln Glu Pro Glu Ser Lys
        35                  40                  45

Tyr Arg Met Thr Pro Pro Gln Leu Asp Glu Asp Gly Ser Tyr Phe Leu
    50                  55                  60

Tyr Ser Lys Leu Ser Val Asp Lys Ser Arg Trp Gln Arg Gly Asp Thr
65                  70                  75                  80

Phe Ile Cys Ala Val Met His Glu Ala Leu His Asn His Tyr Thr Gln
                85                  90                  95

Ile Ser Leu Ser His Ser Pro Gly Lys
            100                 105

<210> SEQ ID NO 8
<211> LENGTH: 106
<212> TYPE: PRT
<213> ORGANISM: Canine

<400> SEQUENCE: 8

Gln Pro Ser Val Tyr Val Leu Pro Pro Ser Pro Lys Glu Leu Ser Ser
1               5                   10                  15

Ser Asp Thr Val Thr Leu Thr Cys Leu Ile Lys Asp Phe Phe Pro Pro
            20                  25                  30

Glu Ile Asp Val Glu Trp Gln Ser Asn Gly Gln Pro Glu Pro Glu Ser
        35                  40                  45

Lys Tyr His Thr Thr Ala Pro Gln Leu Asp Glu Asp Gly Ser Tyr Phe
    50                  55                  60

Leu Tyr Ser Lys Leu Ser Val Asp Lys Ser Arg Trp Gln Gln Gly Asp
65                  70                  75                  80

Thr Phe Thr Cys Ala Val Met His Glu Ala Leu Gln Asn His Tyr Thr
                85                  90                  95

Asp Leu Ser Leu Ser His Ser Pro Gly Lys
            100                 105

<210> SEQ ID NO 9
<211> LENGTH: 220
<212> TYPE: PRT
<213> ORGANISM: Canine

<400> SEQUENCE: 9

Val Pro Glu Pro Leu Gly Gly Pro Ser Val Leu Ile Phe Pro Pro Lys
1               5                   10                  15

Pro Lys Asp Ile Leu Arg Ile Thr Arg Thr Pro Glu Val Thr Cys Val
            20                  25                  30

Val Leu Asp Leu Gly Arg Glu Asp Pro Glu Val Gln Ile Ser Trp Phe
        35                  40                  45

Val Asp Gly Lys Glu Val His Thr Ala Lys Thr Gln Ser Arg Glu Gln
    50                  55                  60
```

```
Gln Phe Asn Gly Thr Tyr Arg Val Val Ser Val Leu Pro Ile Glu His
 65                  70                  75                  80

Gln Asp Trp Leu Thr Gly Lys Glu Phe Lys Cys Arg Val Asn His Ile
                 85                  90                  95

Asp Leu Pro Ser Pro Ile Glu Arg Thr Ile Ser Lys Ala Arg Gly Arg
            100                 105                 110

Ala His Lys Pro Ser Val Tyr Val Leu Pro Pro Ser Pro Lys Glu Leu
        115                 120                 125

Ser Ser Ser Asp Thr Val Ser Ile Thr Cys Leu Ile Lys Asp Phe Tyr
    130                 135                 140

Pro Pro Asp Ile Asp Val Glu Trp Gln Ser Asn Gly Gln Gln Glu Pro
145                 150                 155                 160

Glu Arg Lys His Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Gln
            180                 185                 190

Gly Asp Pro Phe Thr Cys Ala Val Met His Glu Thr Leu Gln Asn His
        195                 200                 205

Tyr Thr Asp Leu Ser Leu Ser His Ser Pro Gly Lys
    210                 215                 220

<210> SEQ ID NO 10
<211> LENGTH: 219
<212> TYPE: PRT
<213> ORGANISM: Canine

<400> SEQUENCE: 10

Ala Pro Glu Met Leu Gly Gly Pro Ser Val Phe Ile Phe Pro Pro Lys
  1               5                  10                  15

Pro Lys Asp Thr Leu Leu Ile Ala Arg Thr Pro Glu Val Thr Cys Val
                 20                  25                  30

Val Val Asp Leu Asp Pro Glu Asp Pro Glu Val Gln Ile Ser Trp Phe
             35                  40                  45

Val Asp Gly Lys Gln Met Gln Thr Ala Lys Thr Gln Pro Arg Glu Glu
 50                  55                  60

Gln Phe Asn Gly Thr Tyr Arg Val Val Ser Val Leu Pro Ile Gly His
 65                  70                  75                  80

Gln Asp Trp Leu Lys Gly Lys Gln Phe Thr Cys Lys Val Asn Asn Lys
                 85                  90                  95

Ala Leu Pro Ser Pro Ile Glu Arg Thr Ile Ser Lys Ala Arg Gly Gln
            100                 105                 110

Ala His Gln Pro Ser Val Tyr Val Leu Pro Pro Ser Arg Glu Glu Leu
        115                 120                 125

Ser Lys Asn Thr Val Ser Leu Thr Cys Leu Ile Lys Asp Phe Phe Pro
    130                 135                 140

Pro Asp Ile Asp Val Glu Trp Gln Ser Asn Gly Gln Gln Glu Pro Glu
145                 150                 155                 160

Ser Lys Tyr Arg Thr Thr Pro Pro Gln Leu Asp Glu Asp Gly Ser Tyr
                165                 170                 175

Phe Leu Tyr Ser Lys Leu Ser Val Asp Lys Ser Arg Trp Gln Arg Gly
            180                 185                 190

Asp Thr Phe Ile Cys Ala Val Met His Glu Ala Leu His Asn His Tyr
        195                 200                 205

Thr Gln Glu Ser Leu Ser His Ser Pro Gly Lys
    210                 215
```

```
<210> SEQ ID NO 11
<211> LENGTH: 219
<212> TYPE: PRT
<213> ORGANISM: Canine

<400> SEQUENCE: 11

Gly Cys Gly Leu Leu Gly Gly Pro Ser Val Phe Ile Phe Pro Pro Lys
1               5                   10                  15

Pro Lys Asp Ile Leu Val Thr Ala Arg Thr Pro Thr Val Thr Cys Val
                20                  25                  30

Val Val Asp Leu Asp Pro Glu Asn Pro Glu Val Gln Ile Ser Trp Phe
            35                  40                  45

Val Asp Ser Lys Gln Val Gln Thr Ala Asn Thr Gln Pro Arg Glu Glu
        50                  55                  60

Gln Ser Asn Gly Thr Tyr Arg Val Val Ser Val Leu Pro Ile Gly His
65                  70                  75                  80

Gln Asp Trp Leu Ser Gly Lys Gln Phe Lys Cys Lys Val Asn Asn Lys
                85                  90                  95

Ala Leu Pro Ser Pro Ile Glu Glu Ile Ile Ser Lys Thr Pro Gly Gln
            100                 105                 110

Ala His Gln Pro Asn Val Tyr Val Leu Pro Pro Ser Arg Asp Glu Met
        115                 120                 125

Ser Lys Asn Thr Val Thr Leu Thr Cys Leu Val Lys Asp Phe Phe Pro
    130                 135                 140

Pro Glu Ile Asp Val Glu Trp Gln Ser Asn Gly Gln Gln Glu Pro Glu
145                 150                 155                 160

Ser Lys Tyr Arg Met Thr Pro Pro Gln Leu Asp Glu Asp Gly Ser Tyr
                165                 170                 175

Phe Leu Tyr Ser Lys Leu Ser Val Asp Lys Ser Arg Trp Gln Arg Gly
            180                 185                 190

Asp Thr Phe Ile Cys Ala Val Met His Glu Ala Leu His Asn His Tyr
        195                 200                 205

Thr Gln Ile Ser Leu Ser His Ser Pro Gly Lys
    210                 215

<210> SEQ ID NO 12
<211> LENGTH: 220
<212> TYPE: PRT
<213> ORGANISM: Canine

<400> SEQUENCE: 12

Val Pro Glu Ser Leu Gly Gly Pro Ser Val Phe Ile Phe Pro Pro Lys
1               5                   10                  15

Pro Lys Asp Ile Leu Arg Ile Thr Arg Thr Pro Glu Ile Thr Cys Val
                20                  25                  30

Val Leu Asp Leu Gly Arg Glu Asp Pro Glu Val Gln Ile Ser Trp Phe
            35                  40                  45

Val Asp Gly Lys Glu Val His Thr Ala Lys Thr Gln Pro Arg Glu Gln
        50                  55                  60

Gln Phe Asn Ser Thr Tyr Arg Val Val Ser Val Leu Pro Ile Glu His
65                  70                  75                  80

Gln Asp Trp Leu Thr Gly Lys Glu Phe Lys Cys Arg Val Asn His Ile
                85                  90                  95

Gly Leu Pro Ser Pro Ile Glu Arg Thr Ile Ser Lys Ala Arg Gly Gln
            100                 105                 110
```

```
Ala His Gln Pro Ser Val Tyr Val Leu Pro Ser Pro Lys Glu Leu
        115                 120                 125

Ser Ser Ser Asp Thr Val Thr Leu Thr Cys Leu Ile Lys Asp Phe Phe
130                 135                 140

Pro Pro Glu Ile Asp Val Glu Trp Gln Ser Asn Gly Gln Pro Glu Pro
145                 150                 155                 160

Glu Ser Lys Tyr His Thr Thr Ala Pro Gln Leu Asp Glu Asp Gly Ser
                165                 170                 175

Tyr Phe Leu Tyr Ser Lys Leu Ser Val Asp Lys Ser Arg Trp Gln Gln
            180                 185                 190

Gly Asp Thr Phe Thr Cys Ala Val Met His Glu Ala Leu Gln Asn His
                195                 200                 205

Tyr Thr Asp Leu Ser Leu Ser His Ser Pro Gly Lys
        210                 215                 220

<210> SEQ ID NO 13
<211> LENGTH: 468
<212> TYPE: PRT
<213> ORGANISM: Canine

<400> SEQUENCE: 13

Met Glu Ser Val Phe Cys Trp Val Phe Leu Val Val Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Ser Tyr Tyr Met His Trp Ile Arg Gln Ala Pro Gly Lys Gly Leu
    50                  55                  60

Gln Arg Val Ala His Ile Arg Gly Asp Gly Arg Thr Thr His Tyr Ala
65                  70                  75                  80

Asp Ala Met Lys Gly Arg Phe Thr Ile Ser Arg Asp Asn Ala Lys Asn
                85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
        115                 120                 125

Gln Gly Thr Leu Val Thr Val Ser Ser Ala Ser Thr Thr Ala Pro Ser
    130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

Ser Trp Asn Ser Gly Ser Leu Thr Ser Gly Val His Thr Phe Pro Ser
            180                 185                 190

Val Leu Gln Ser Ser Gly Leu His Ser Leu Ser Ser Met Val Thr Val
        195                 200                 205

Pro Ser Ser Arg Trp Pro Ser Glu Thr Phe Thr Cys Asn Val Val His
    210                 215                 220

Pro Ala Ser Asn Thr Lys Val Asp Lys Pro Val Phe Asn Glu Cys Arg
225                 230                 235                 240

Cys Thr Asp Thr Pro Cys Pro Val Pro Glu Pro Leu Gly Gly Pro
                245                 250                 255

Ser Val Leu Ile Phe Pro Pro Lys Pro Lys Asp Ile Leu Arg Ile Thr
```

```
                    260                 265                 270
Arg Thr Pro Glu Val Thr Cys Val Leu Asp Leu Gly Arg Glu Asp
                275                 280                 285
Pro Glu Val Gln Ile Ser Trp Phe Val Asp Gly Lys Glu Val His Thr
            290                 295                 300
Ala Lys Thr Gln Ser Arg Glu Gln Gln Phe Asn Gly Thr Tyr Arg Val
305                 310                 315                 320
Val Ser Val Leu Pro Ile Glu His Gln Asp Trp Leu Thr Gly Lys Glu
                325                 330                 335
Phe Lys Cys Arg Val Asn His Ile Asp Leu Pro Ser Pro Ile Glu Arg
                340                 345                 350
Thr Ile Ser Lys Ala Arg Gly Arg Ala His Lys Pro Ser Val Tyr Val
                355                 360                 365
Leu Pro Pro Ser Pro Lys Glu Leu Ser Ser Ser Asp Thr Val Ser Ile
                370                 375                 380
Thr Cys Leu Ile Lys Asp Phe Tyr Pro Pro Asp Ile Asp Val Glu Trp
385                 390                 395                 400
Gln Ser Asn Gly Gln Gln Glu Pro Glu Arg Lys His Arg Met Thr Pro
                405                 410                 415
Pro Gln Leu Asp Glu Asp Gly Ser Tyr Phe Leu Tyr Ser Lys Leu Ser
                420                 425                 430
Val Asp Lys Ser Arg Trp Gln Gln Gly Asp Pro Phe Thr Cys Ala Val
                435                 440                 445
Met His Glu Thr Leu Gln Asn His Tyr Thr Asp Leu Ser Leu Ser His
                450                 455                 460
Ser Pro Gly Lys
465

<210> SEQ ID NO 14
<211> LENGTH: 96
<212> TYPE: PRT
<213> ORGANISM: Canine

<400> SEQUENCE: 14

Leu Phe Thr Arg Thr Lys Arg Arg Ser Asp Val Ser Trp Gly Asn Thr
1               5                   10                  15
Gly Ser Ser Gln Thr Val Ile Arg Ala Ser Val Ala Ser Trp Ser Arg
            20                  25                  30
Asn Gly Asp Leu Tyr Ala Pro Lys Pro Lys Arg Glu Asn Gly Arg Val
        35                  40                  45
Pro Arg Pro Pro Asp Cys Lys Ala Met Phe Thr Leu Leu Ala Val Asp
    50                  55                  60
Pro Gln Met Gln Pro Glu Gly Lys Gln Thr Lys Asn Lys Ala Gln Gln
65                  70                  75                  80
Arg Glu Lys Asn Leu Phe Ser Tyr Thr Arg Thr Ile Ala His Gln Glu
                85                  90                  95

<210> SEQ ID NO 15
<211> LENGTH: 105
<212> TYPE: PRT
<213> ORGANISM: Canine

<400> SEQUENCE: 15

Leu Tyr Ala Asp Cys Ala Ser Val Ser Pro Trp Thr Tyr Ser Asp Ile
1               5                   10                  15
Tyr Ser Val Arg Ala Val Ala Ala Pro Tyr Asp Ser His Tyr Met Pro
```

```
                    20                  25                  30

Ser Leu Phe Gln Ile Val Tyr Ala Thr Ala Lys Glu Lys Cys Asn Cys
            35                  40                  45

Asn Asn Cys Gly Cys Gly Leu Phe Val Thr Ala Thr Val Asp Pro Asn
        50                  55                  60

Ser Gln Gln Asn Pro Glu Ser Gly Ser Gln Lys Asn Lys Ala Glu Ile
65                  70                  75                  80

Thr Pro Gln Gln Asn Arg Asp Met Lys Asn Thr Leu Val Phe Glu Ser
                85                  90                  95

Tyr Met Arg Thr Ile Ala His Gln Ile
            100                 105

<210> SEQ ID NO 16
<211> LENGTH: 66
<212> TYPE: PRT
<213> ORGANISM: Canine

<400> SEQUENCE: 16

Leu Ser Asp Gly Ser Val Ser Trp Ala Val Ser Asn Arg Asp Tyr Ser
1               5                   10                  15

Lys Ala Ile His Val Thr Gly Val Trp Pro Arg His Met His Asn Ser
            20                  25                  30

Leu Phe Tyr Thr Pro Lys Ser Thr Lys Cys Ile Ser Pro Glu Ser Phe
        35                  40                  45

Ile Pro Ser Gly Gln Gln Thr Leu Phe Glu Pro Ser Tyr His Thr Ala
    50                  55                  60

Thr Ala
65

<210> SEQ ID NO 17
<211> LENGTH: 17
<212> TYPE: PRT
<213> ORGANISM: Canine

<400> SEQUENCE: 17

Phe Asn Glu Cys Arg Cys Thr Asp Thr Pro Pro Cys Pro Val Pro Glu
1               5                   10                  15

Pro

<210> SEQ ID NO 18
<211> LENGTH: 22
<212> TYPE: PRT
<213> ORGANISM: Canine

<400> SEQUENCE: 18

Pro Lys Arg Glu Asn Gly Arg Val Pro Arg Pro Asp Cys Pro Lys
1               5                   10                  15

Cys Pro Ala Pro Glu Met
            20

<210> SEQ ID NO 19
<211> LENGTH: 20
<212> TYPE: PRT
<213> ORGANISM: Canine

<400> SEQUENCE: 19

Ala Lys Glu Cys Glu Cys Lys Cys Asn Cys Asn Asn Cys Pro Cys Pro
1               5                   10                  15

Gly Cys Gly Leu
```

```
<210> SEQ ID NO 20
<211> LENGTH: 17
<212> TYPE: PRT
<213> ORGANISM: Canine

<400> SEQUENCE: 20

Pro Lys Glu Ser Thr Cys Lys Cys Ile Ser Pro Cys Pro Val Pro Glu
1               5                   10                  15

Ser

<210> SEQ ID NO 21
<211> LENGTH: 17
<212> TYPE: PRT
<213> ORGANISM: Canine

<400> SEQUENCE: 21

Pro Lys Glu Ser Thr Cys Lys Cys Ile Pro Pro Cys Pro Val Pro Glu
1               5                   10                  15

Ser

<210> SEQ ID NO 22
<211> LENGTH: 12
<212> TYPE: PRT
<213> ORGANISM: Artificial
<220> FEATURE:
<223> OTHER INFORMATION: synthetic polypeptide

<400> SEQUENCE: 22

Gly Leu Tyr Gly Leu Tyr Gly Leu Tyr Ser Glu Arg
1               5                   10

<210> SEQ ID NO 23
<211> LENGTH: 12
<212> TYPE: PRT
<213> ORGANISM: Artificial
<220> FEATURE:
<223> OTHER INFORMATION: synthetic polypeptide

<400> SEQUENCE: 23

Ser Glu Arg Gly Leu Tyr Gly Leu Tyr Gly Leu Tyr
1               5                   10

<210> SEQ ID NO 24
<211> LENGTH: 15
<212> TYPE: PRT
<213> ORGANISM: Artificial
<220> FEATURE:
<223> OTHER INFORMATION: synthetic polypeptide

<400> SEQUENCE: 24

Gly Leu Tyr Gly Leu Tyr Gly Leu Tyr Gly Leu Tyr Ser Glu Arg
1               5                   10                  15

<210> SEQ ID NO 25
<211> LENGTH: 15
<212> TYPE: PRT
<213> ORGANISM: Artificial
<220> FEATURE:
<223> OTHER INFORMATION: synthetic polypeptide

<400> SEQUENCE: 25

Ser Glu Arg Gly Leu Tyr Gly Leu Tyr Gly Leu Tyr Gly Leu Tyr
1               5                   10                  15
```

<210> SEQ ID NO 26
<211> LENGTH: 18
<212> TYPE: PRT
<213> ORGANISM: Artificial
<220> FEATURE:
<223> OTHER INFORMATION: synthetic polypeptide

<400> SEQUENCE: 26

Gly Leu Tyr Gly Leu Tyr Gly Leu Tyr Gly Leu Tyr Gly Leu Tyr Ser
1               5                   10                  15

Glu Arg

<210> SEQ ID NO 27
<211> LENGTH: 18
<212> TYPE: PRT
<213> ORGANISM: Artificial
<220> FEATURE:
<223> OTHER INFORMATION: synthetic polypeptide

<400> SEQUENCE: 27

Ser Glu Arg Gly Leu Tyr Gly Leu Tyr Gly Leu Tyr Gly Leu Tyr Gly
1               5                   10                  15

Leu Tyr

<210> SEQ ID NO 28
<211> LENGTH: 21
<212> TYPE: PRT
<213> ORGANISM: Artificial
<220> FEATURE:
<223> OTHER INFORMATION: synthetic polypeptide

<400> SEQUENCE: 28

Gly Leu Tyr Gly Leu Tyr Gly Leu Tyr Gly Leu Tyr Gly Leu Tyr Gly
1               5                   10                  15

Leu Tyr Ser Glu Arg
            20

<210> SEQ ID NO 29
<211> LENGTH: 21
<212> TYPE: PRT
<213> ORGANISM: Artificial
<220> FEATURE:
<223> OTHER INFORMATION: synthetic polypeptide

<400> SEQUENCE: 29

Ser Glu Arg Gly Leu Tyr Gly Leu Tyr Gly Leu Tyr Gly Leu Tyr Gly
1               5                   10                  15

Leu Tyr Gly Leu Tyr
            20

<210> SEQ ID NO 30
<211> LENGTH: 202
<212> TYPE: PRT
<213> ORGANISM: Canine

<400> SEQUENCE: 30

Val Phe Ile Phe Pro Pro Lys Pro Lys Asp Thr Leu Leu Ile Ala Arg
1               5                   10                  15

Thr Pro Glu Val Thr Cys Val Val Asp Leu Asp Pro Glu Asp Pro
            20                  25                  30

Glu Val Gln Ile Ser Trp Phe Val Asp Gly Lys Gln Met Gln Thr Ala
                35                  40                  45

```
Lys Thr Gln Pro Arg Glu Glu Gln Phe Asn Gly Thr Tyr Arg Val Val
 50                  55                  60

Ser Val Leu Pro Ile Gly His Gln Asp Trp Leu Lys Gly Lys Gln Phe
 65                  70                  75                  80

Thr Cys Lys Val Asn Asn Lys Ala Leu Pro Ser Pro Ile Glu Arg Thr
                 85                  90                  95

Ile Ser Lys Ala Arg Gly Gln Ala His Gln Pro Ser Val Tyr Val Leu
                100                 105                 110

Pro Pro Ser Arg Glu Glu Leu Ser Lys Asn Thr Val Ser Leu Thr Cys
                115                 120                 125

Leu Ile Lys Asp Phe Phe Pro Pro Asp Ile Asp Val Glu Trp Gln Ser
130                 135                 140

Asn Gly Gln Gln Glu Pro Glu Ser Lys Tyr Arg Thr Thr Pro Pro Gln
145                 150                 155                 160

Leu Asp Glu Asp Gly Ser Tyr Phe Leu Tyr Ser Lys Leu Ser Val Asp
                165                 170                 175

Lys Ser Arg Trp Gln Arg Gly Asp Thr Phe Ile Cys Ala Val Met His
                180                 185                 190

Glu Ala Leu His Asn His Tyr Thr Gln Glu
                195                 200

<210> SEQ ID NO 31
<211> LENGTH: 200
<212> TYPE: PRT
<213> ORGANISM: human

<400> SEQUENCE: 31

Val Phe Leu Phe Pro Pro Lys Pro Lys Asp Thr Leu Met Ile Ser Arg
 1               5                  10                  15

Thr Pro Glu Val Thr Cys Val Val Asp Val Ser His Glu Asp Pro
                 20                  25                  30

Glu Val Lys Phe Asn Trp Tyr Val Asp Gly Val Glu Val His Asn Ala
                 35                  40                  45

Lys Thr Lys Pro Arg Glu Glu Gln Tyr Asn Ser Thr Tyr Arg Val Val
 50                  55                  60

Ser Val Leu Thr Val Leu His Gln Asp Trp Leu Asn Gly Lys Glu Tyr
 65                  70                  75                  80

Lys Cys Lys Val Ser Asn Lys Ala Leu Pro Ala Pro Ile Glu Lys Thr
                 85                  90                  95

Ile Ser Lys Ala Lys Gly Gln Pro Arg Glu Pro Gln Val Tyr Thr Leu
                100                 105                 110

Pro Pro Ser Arg Glu Glu Met Thr Lys Asn Gln Val Ser Leu Thr Cys
                115                 120                 125

Leu Val Lys Gly Phe Tyr Pro Ser Asp Ile Ala Val Glu Trp Glu Ser
130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
                180                 185                 190

Leu His Asn His Tyr Thr Gln Lys
                195                 200
```